(12) United States Patent
Mathews et al.

(10) Patent No.: US 8,895,474 B2
(45) Date of Patent: Nov. 25, 2014

(54) HERBICIDALLY ACTIVE CYCLOPENTANEDIONES AND DERIVATIVES THEREOF, AND THEIR USE IN CONTROLLING WEEDS

(75) Inventors: Christopher John Mathews, Bracknell (GB); John Finney, Bracknell (GB); James Nicholas Scutt, Bracknell (GB); Louisa Robinson, Bracknell (GB); John Stephen Delaney, Bracknell (GB)

(73) Assignee: Syngenta Limited, Guildford, Surrey (GB)

( * ) Notice: Subject to any disclaimer, the term of this patent is extended or adjusted under 35 U.S.C. 154(b) by 31 days.

(21) Appl. No.: 13/145,915

(22) PCT Filed: Jan. 18, 2010

(86) PCT No.: PCT/EP2010/050491
§ 371 (c)(1),
(2), (4) Date: Oct. 17, 2011

(87) PCT Pub. No.: WO2010/102848
PCT Pub. Date: Sep. 16, 2010

(65) Prior Publication Data
US 2012/0021912 A1 Jan. 26, 2012

(30) Foreign Application Priority Data
Jan. 22, 2009 (GB) .................................... 0901086

(51) Int. Cl.
| | |
|---|---|
| *A01N 35/06* | (2006.01) |
| *A01N 37/34* | (2006.01) |
| *A01N 43/40* | (2006.01) |
| *A01N 43/42* | (2006.01) |
| *A01N 43/54* | (2006.01) |
| *C07D 307/12* | (2006.01) |
| *C07D 241/44* | (2006.01) |
| *C07D 307/93* | (2006.01) |
| *A01N 43/90* | (2006.01) |
| *A01N 43/60* | (2006.01) |
| *C07D 311/96* | (2006.01) |
| *C07D 309/04* | (2006.01) |
| *C07D 277/68* | (2006.01) |
| *C07C 49/753* | (2006.01) |
| *C07D 239/34* | (2006.01) |
| *A01N 43/78* | (2006.01) |
| *C07D 213/64* | (2006.01) |

(52) U.S. Cl.
CPC ............ *C07D 213/64* (2013.01); *C07D 307/12* (2013.01); *A01N 43/40* (2013.01); *C07D 241/44* (2013.01); *A01N 43/42* (2013.01); *A01N 37/34* (2013.01); *C07D 307/93* (2013.01); *A01N 43/90* (2013.01); *A01N 43/60* (2013.01); *A01N 35/06* (2013.01); *C07D 311/96* (2013.01); *C07D 309/04* (2013.01); *C07D 277/68* (2013.01); *C07C 49/753* (2013.01); *C07D 239/34* (2013.01); *A01N 43/78* (2013.01); *A01N 43/54* (2013.01)

USPC ............ 504/210; 504/326; 504/349; 504/351; 504/353; 504/354; 504/355; 504/356; 504/358; 504/235; 504/242; 504/247; 504/256; 504/267

(58) Field of Classification Search
CPC ......... A01N 35/06; A01N 7/34; A01N 43/40; A01N 43/42; A01N 43/54
USPC ......... 504/210, 326, 349, 351, 353, 354, 355, 504/356, 358, 235, 242, 247, 256, 267
See application file for complete search history.

(56) References Cited

U.S. PATENT DOCUMENTS

| | | |
|---|---|---|
| 4,175,135 A | 11/1979 | Haines et al. |
| 4,209,532 A | 6/1980 | Wheeler et al. |
| 4,409,153 A | 10/1983 | Hodakowski et al. |
| 4,489,012 A | 12/1984 | Hodakowski |
| 4,526,723 A | 7/1985 | Wheeler et al. |
| 4,659,372 A | 4/1987 | Wheeler et al. |
| 5,801,120 A | 9/1998 | Lee et al. |
| 5,808,135 A | 9/1998 | Fischer et al. |

(Continued)

FOREIGN PATENT DOCUMENTS

| | | |
|---|---|---|
| CA | 2322158 | 8/2000 |
| CA | 2325526 | 9/2000 |

(Continued)

OTHER PUBLICATIONS

Muehlebach, M., et al., "Discovery and SAR of pinoxaden: a new broad spectrum, postemergence cereal herbicide," in Pesticide Chemistry, Crop Protection, Public Health, Environmental Safety, ed. H. Ohkawa et al., Jun. 2007, pp. 101-110.

(Continued)

*Primary Examiner* — Richard Schnizer
*Assistant Examiner* — Alma Pipic
(74) *Attorney, Agent, or Firm* — R. Kody Jones

(57) ABSTRACT

Compounds of Formula (I), wherein the substituents are as defined in claim 1, are suitable for use as herbicides.

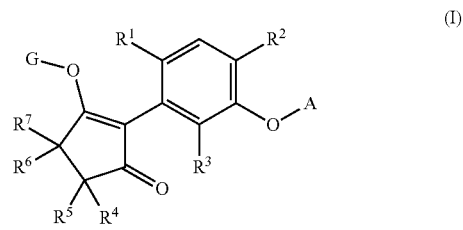

19 Claims, No Drawings

(56) References Cited

U.S. PATENT DOCUMENTS

| | | |
|---|---|---|
| 5,840,661 A | 11/1998 | Fischer et al. |
| 6,251,833 B1 | 6/2001 | Erdelen et al. |
| 6,458,965 B1 | 10/2002 | Lieb et al. |
| 6,642,180 B1 | 11/2003 | Fischer et al. |
| 6,894,005 B1 | 5/2005 | Maetzke et al. |
| 8,058,210 B2 | 11/2011 | Lieb et al. |
| 8,084,649 B2 | 12/2011 | Muehlebach et al. |
| 2003/0216260 A1 | 11/2003 | Ruther et al. |
| 2005/0164883 A1 | 7/2005 | Maetzke et al. |
| 2006/0166829 A1 | 7/2006 | Fischer et al. |
| 2010/0113270 A1 | 5/2010 | Mathews et al. |
| 2010/0210466 A1 | 8/2010 | Muehlebach et al. |
| 2010/0216638 A1 | 8/2010 | Mathews et al. |
| 2010/0279868 A1 | 11/2010 | Jeanmart et al. |
| 2010/0298140 A1 | 11/2010 | Jeansmart et al. |
| 2012/0021907 A1 | 1/2012 | Mathews et al. |
| 2012/0021909 A1 | 1/2012 | Mathews et al. |
| 2012/0028800 A1 | 2/2012 | Mathews et al. |
| 2012/0040826 A1 | 2/2012 | Jeanmart et al. |
| 2012/0094832 A1 | 4/2012 | Tyte et al. |
| 2012/0142529 A1 | 6/2012 | Tyte et al. |

FOREIGN PATENT DOCUMENTS

| | | |
|---|---|---|
| CA | 2382432 | 2/2002 |
| CA | 2382435 | 2/2002 |
| CA | 2456776 | 2/2004 |
| WO | 9216510 A1 | 10/1992 |
| WO | 9601798 A1 | 1/1996 |
| WO | 9603366 A1 | 2/1996 |
| WO | 9611574 A1 | 4/1996 |
| WO | 9621652 A1 | 7/1996 |
| WO | 9839281 A1 | 9/1998 |
| WO | 99/43649 | 9/1999 |
| WO | 99/47525 | 9/1999 |
| WO | 99/48869 | 9/1999 |
| WO | 00/37437 | 6/2000 |
| WO | 0109092 A1 | 2/2001 |
| WO | 01/17972 | 3/2001 |
| WO | 01/17973 | 3/2001 |
| WO | 01/74770 | 10/2001 |
| WO | 03/013249 | 2/2003 |
| WO | 2004111042 | 12/2004 |
| WO | 2005/123667 | 12/2005 |
| WO | 2006034315 | 3/2006 |
| WO | 2006034446 | 3/2006 |
| WO | 2008/071405 | 6/2008 |
| WO | 2009015877 | 7/2008 |
| WO | 2008/110307 | 9/2008 |
| WO | 2008/110308 | 9/2008 |
| WO | 2008145336 | 12/2008 |
| WO | 2009000533 | 12/2008 |
| WO | 2009074314 | 12/2008 |
| WO | 2009019015 | 2/2009 |
| WO | 2009030450 | 3/2009 |
| WO | 2010001755 | 1/2010 |
| WO | 2010089210 | 8/2010 |
| WO | 2010089211 | 8/2010 |

OTHER PUBLICATIONS

Wenger, J., and Nidermann, T., "Chapter 9: Acetyl-CoA Carboxylase Inhibitors", in Modern Crop Protection Compounds, ed. W. Kraemer et al., Wiley-VCH Verlag, Weinheim, 2007, pp. 335-357.

Wenger, et al.: "Chapter 11: Acetyl-CoA Carboxylase Inhibitors", in Modern Crop Protection Compounds, Second Edition, Jan. 2012, pp. 447-477.

HERBICIDALLY ACTIVE CYCLOPENTANEDIONES AND DERIVATIVES THEREOF, AND THEIR USE IN CONTROLLING WEEDS

This application is a 371 of International Application No. PCT/EP2010/050491 filed Jan. 18, 2010, which claims priority to GB 0901086.9 filed Jan. 22, 2009, the contents of which are incorporated herein by reference.

The present invention relates to novel, herbicidally active cyclopentanediones, and derivatives thereof, to processes for their preparation, to compositions comprising those compounds, and to their use in controlling weeds, especially in crops of useful plants, or in inhibiting undesired plant growth.

Cyclopentanediones having herbicidal action are described, for example, in WO 01/74770, WO 96/03366 and U.S. Pat. No. 4,283,348.

Novel cyclopentanediones, and derivatives thereof, having herbicidal and growth-inhibiting properties have now been found.

The present invention accordingly relates to compounds of formula I

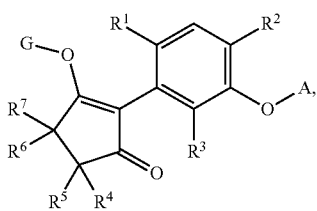

I wherein
A is a mono- or bicyclic aryl or heteroaryl which contains a heteroatom selected from nitrogen, oxygen and sulfur, and which is unsubstituted or substituted,
$R^1$ is methyl, ethyl, n-propyl, isopropyl, cyclopropyl, halomethyl, haloethyl, vinyl, propenyl, ethynyl, propynyl, halogen, methoxy, ethoxy, halomethoxy or haloethoxy,
$R^2$ and $R^3$ are independently of each other hydrogen, methyl, ethyl, n-propyl, isopropyl, cyclopropyl, halomethyl, haloethyl, vinyl, propenyl, ethynyl, propynyl, halogen, methoxy, ethoxy, halomethoxy or haloethoxy,
$R^4$, $R^5$, $R^6$, and $R^7$ are independently of each other hydrogen, halogen, optionally substituted $C_1$-$C_6$alkyl, optionally substituted $C_3$-$C_7$cycloalkyl, optionally substituted $C_2$-$C_6$ alkenyl, optionally substituted $C_5$-$C_7$cycloalkenyl, optionally substituted $C_2$-$C_6$alkynyl, optionally substituted $C_1$-$C_6$ alkoxy, optionally substituted $C_3$-$C_7$cycloalkyloxy, optionally substituted $C_1$-$C_6$alkylthio, optionally substituted $C_1$-$C_6$alkylsulfinyl, optionally substituted $C_1$-$C_6$alkylsulfonyl, optionally substituted aryl, optionally substituted aryloxy, optionally substituted arylthio, optionally substituted arylsulfinyl, optionally substituted arylsulfonyl, optionally substituted heterocyclyl, optionally substituted heterocyclyloxy, optionally substituted heterocyclylthio, optionally substituted heterocyclylsulfinyl, optionally substituted heterocyclylsulfonyl, optionally substituted heteroaryl, optionally substituted heteroaryloxy, optionally substituted heteroarylthio, optionally substituted heteroarylsulfinyl, optionally substituted heteroarylsulfonyl, cyano or optionally substituted amino, or $R^4$ and $R^5$, or $R^6$ and $R^7$ together with the atoms to which they are bonded form an optionally substituted saturated or unsaturated carbocyclyl or heterocyclyl which contains one or two heteroatoms selected from nitrogen, oxygen or sulfur, or $R^5$ and $R^6$, together with the atoms to which they are bonded form an optionally substituted saturated or unsaturated carbocyclyl or heterocyclyl which contains one or two heteroatoms selected from nitrogen, oxygen or sulfur, and which carbocyclyl may further be bridged by optionally substituted $C_1$-$C_2$ alkyldiyl or by oxygen, and
G is hydrogen or an agriculturally acceptable metal, sulfonium, ammonium or latentiating group.

In the substituent definitions of the compounds of the formula I, each alkyl moiety either alone or as part of a larger group (such as alkoxy, alkylthio, alkoxycarbonyl, alkylcarbonyl, alkylaminocarbonyl, dialkylaminocarbonyl) is a straight or branched chain and is, for example, methyl, ethyl, n-propyl, n-butyl, n-pentyl, n-hexyl, isopropyl, n-butyl, sec-butyl, isobutyl, tert-butyl or neopentyl. The alkyl groups are suitably $C_1$-$C_3$alkyl groups, but are preferably $C_1$-$C_4$alkyl or $C_1$-$C_3$alkyl groups, and, more preferably, $C_1$-$C_2$alkyl groups.

When present, the optional substituents on an alkyl moiety (alone or as part of a larger group such as alkoxy, alkoxycarbonyl, alkylcarbonyl, alkylaminocarbonyl, dialkylaminocarbonyl) include one or more of halogen, nitro, cyano, $C_3$-$C_7$cycloalkyl (itself optionally substituted with $C_1$-$C_6$alkyl or halogen), $C_5$-$C_7$cycloalkenyl (itself optionally substituted with $C_1$-$C_4$alkyl or halogen), hydroxy, $C_1$-$C_{10}$alkoxy, $C_1$-$C_{10}$alkoxy($C_1$-$C_{10}$)alkoxy, tri($C_1$-$C_4$)alkylsilyl($C_1$-$C_6$)alkoxy, $C_1$-$C_6$alkoxycarbonyl($C_1$-$C_{10}$)alkoxy, $C_1$-$C_{10}$haloalkoxy, aryl($C_1$-$C_4$)alkoxy (where the aryl group is optionally substituted), $C_3$-$C_7$cycloalkyloxy (where the cycloalkyl group is optionally substituted with $C_1$-$C_6$alkyl or halogen), $C_3$-$C_{10}$alkenyloxy, $C_3$-$C_{10}$alkynyloxy, mercapto, $C_1$-$C_{10}$alkylthio, $C_1$-$C_{10}$haloalkylthio, aryl($C_1$-$C_4$)alkylthio (where the aryl group is optionally substituted), $C_3$-$C_7$cycloalkylthio (where the cycloalkyl group is optionally substituted with $C_1$-$C_6$alkyl or halogen), tri($C_1$-$C_4$)alkylsilyl($C_1$-$C_6$)alkylthio, arylthio (where the aryl group is optionally substituted), $C_1$-$C_6$alkylsulfonyl, $C_1$-$C_6$haloalkylsulfonyl, $C_1$-$C_6$alkylsulfinyl, $C_1$-$C_6$haloalkylsulfinyl, arylsulfonyl (where the aryl group is optionally substituted), tri($C_1$-$C_4$)alkylsilyl, aryldi($C_1$-$C_4$)alkylsilyl, ($C_1$-$C_4$)alkyldiarylsilyl, triarylsilyl, aryl($C_1$-$C_4$)alkylthio($C_1$-$C_4$)alkyl, aryloxy($C_1$-$C_4$)alkyl, formyl, $C_1$-$C_{10}$alkylcarbonyl, $HO_2C$, $C_1$-$C_{10}$alkoxycarbonyl, aminocarbonyl, $C_1$-$C_6$alkylaminocarbonyl, di($C_1$-$C_6$ alkyl)aminocarbonyl, N—($C_1$-$C_3$alkyl)-N—($C_1$-$C_3$ alkoxy)aminocarbonyl, $C_1$-$C_6$alkylcarbonyloxy, arylcarbonyloxy (where the aryl group is optionally substituted), di($C_1$-$C_6$)alkylaminocarbonyloxy, $C_1$-$C_6$alkyliminooxy, $C_3$-$C_6$alkenyloxyimino, aryloxyimino, aryl (itself optionally substituted), heteroaryl (itself optionally substituted), heterocyclyl (itself optionally substituted with $C_1$-$C_6$alkyl or halogen), aryloxy (where the aryl group is optionally substituted), heteroaryloxy, (where the heteroaryl group is optionally substituted), heterocyclyloxy (where the heterocyclyl group is optionally substituted with $C_1$-$C_6$alkyl or halogen), amino, $C_1$-$C_6$alkylamino, di($C_1$-$C_6$)alkylamino, $C_1$-$C_6$alkylcarbonylamino, N—($C_1$-$C_6$)alkylcarbonyl-N—($C_1$-$C_6$)alkylamino, $C_2$-$C_6$alkenylcarbonyl, $C_2$-$C_6$alkynylcarbonyl, $C_3$-$C_6$alkenyloxycarbonyl, $C_3$-$C_6$alkynyloxycarbonyl, aryloxycarbonyl (where the aryl group is optionally substituted) and arylcarbonyl (where the aryl group is optionally substituted).

Alkenyl and alkynyl moieties can be in the form of straight or branched chains, and the alkenyl moieties, where appropriate, can be of either the (E)- or (Z)-configuration. Examples are vinyl, allyl and propargyl. Alkenyl and alkynyl moieties can contain one or more double and/or triple bonds in any combination. It is understood, that allenyl and alkylinylalkenyl are included in these terms.

When present, the optional substituents on alkenyl or alkynyl include those optional substituents given above for an alkyl moiety.

Halogen is fluorine, chlorine, bromine or iodine.

Haloalkyl groups are alkyl groups which are substituted with one or more of the same or different halogen atoms and are, for example, $CF_3$, $CF_2Cl$, $CF_2H$, $CCl_2H$, $FCH_2$, $ClCH_2$, $BrCH_2$, $CH_3CHF$, $(CH_3)_2CF$, $CF_3CH_2$ or $CHF_2CH_2$.

In the context of the present specification the term "aryl" refers to ring systems which may be mono-, or bicyclic. Examples of such rings include phenyl and naphthyl. A preferred aryl group is phenyl.

The term "heteroaryl" preferably refers to an aromatic ring system containing at least one heteroatom and consisting either of a single ring or of two fused rings. Preferably, single rings will contain up to three and bicyclic systems up to four heteroatoms which will preferably be chosen from nitrogen, oxygen and sulphur. Examples of such groups include furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl.

The term "heterocyclyl" preferably refers to a non-aromatic preferably monocyclic or bicyclic ring systems containing up to 7 atoms including one or more (preferably one or two) heteroatoms selected from O, S and N. Examples of such rings include 1,3-dioxolane, oxetane, tetrahydrofuran, morpholine, thiomorpholin and piperazine. When present, the optional substituents on heterocyclyl include $C_1$-$C_6$alkyl and $C_1$-$C_6$haloalkyl as well as those optional substituents given above for an alkyl moiety.

Cycloalkyl includes preferably cyclopropyl, cyclobutyl, cyclopentyl and cyclohexyl. Cycloalkylalkyl is preferentially cyclopropylmethyl. Cycloalkenyl includes preferably cyclopentenyl and cyclohexenyl. When present, the optional substituents on cycloalkyl or cycloalkenyl include $C_1$-$C_3$alkyl as well as those optional substituents given above for an alkyl moiety.

Carbocyclic rings (carbocyclyl) include aryl, cycloalkyl or carbocyclic groups, and cycloalkenyl groups.

When present, the optional substituents on aryl, heteroaryl and carbocycles are preferably selected independently, from halogen, nitro, cyano, rhodano, isothiocyanato, $C_1$-$C_6$alkyl, $C_1$-$C_6$haloalkyl, $C_1$-$C_6$alkoxy($C_1$-$C_6$)alkyl, $C_2$-$C_6$alkenyl, $C_2$-$C_6$haloalkenyl, $C_2$-$C_6$alkynyl, $C_3$-$C_7$cycloalkyl (itself optionally substituted with $C_1$-$C_6$alkyl or halogen), $C_{5-7}$cycloalkenyl (itself optionally substituted with $C_1$-$C_6$alkyl or halogen), hydroxy, $C_1$-$C_{10}$alkoxy, $C_1$-$C_{10}$alkoxy($C_1$-$C_{10}$)alkoxy, tri($C_1$-$C_4$)alkylsilyl($C_1$-$C_6$)alkoxy, $C_1$-$C_6$alkoxycarbonyl($C_1$-$C_{10}$)alkoxy, $C_1$-$C_{10}$haloalkoxy, aryl($C_1$-$C_4$)alkoxy (where the aryl group is optionally substituted with halogen or $C_1$-$C_6$alkyl), $C_3$-$C_7$cycloalkyloxy (where the cycloalkyl group is optionally substituted with $C_1$-$C_6$alkyl or halogen), $C_3$-$C_{10}$alkenyloxy, $C_3$-$C_{10}$alkynyloxy, mercapto, $C_1$-$C_{10}$alkylthio, $C_1$-$C_{10}$haloalkylthio, aryl($C_1$-$C_4$)alkylthio, $C_3$-$C_7$cycloalkylthio (where the cycloalkyl group is optionally substituted with $C_1$-$C_6$alkyl or halogen), tri($C_1$-$C_4$)alkylsilyl($C_1$-$C_6$)alkylthio, arylthio, $C_1$-$C_6$alkylsulfonyl, $C_1$-$C_6$haloalkylsulfonyl, $C_1$-$C_6$alkylsulfinyl, $C_1$-$C_6$haloalkylsulfinyl, arylsulfonyl, tri($C_1$-$C_4$)alkylsilyl, aryldi($C_1$-$C_4$)alkylsilyl, $C_1$-$C_4$alkyldiarylsilyl, triarylsilyl, $C_1$-$C_{10}$alkylcarbonyl, $HO_2C$, $C_1$-$C_{10}$alkoxycarbonyl, aminocarbonyl, $C_1$-$C_6$alkylaminocarbonyl, di($C_1$-$C_6$alkyl)-aminocarbonyl, N—($C_1$-$C_3$ alkyl)-N—($C_1$-$C_3$alkoxy)aminocarbonyl, $C_1$-$C_6$alkylcarbonyloxy, arylcarbonyloxy, di($C_1$-$C_6$)alkylaminocarbonyloxy, aryl (itself optionally substituted with $C_1$-$C_6$alkyl or halogen), heteroaryl (itself optionally substituted with $C_1$-$C_6$alkyl or halogen), heterocyclyl (itself optionally substituted with $C_1$-$C_6$alkyl or halogen), aryloxy (where the aryl group is optionally substituted with $C_1$-$C_6$alkyl or halogen), heteroaryloxy (where the heteroaryl group is optionally substituted with $C_1$-$C_6$alkyl or halogen), heterocyclyloxy (where the heterocyclyl group is optionally substituted with $C_1$-$C_6$alkyl or halogen), amino, $C_1$-$C_6$alkylamino, di($C_1$-$C_6$)alkylamino, $C_1$-$C_6$alkylcarbonylamino, N—($C_1$-$C_6$)alkylcarbonyl-N—($C_1$-$C_6$)alkylamino, arylcarbonyl, (where the aryl group is itself optionally substituted with halogen or $C_1$-$C_6$alkyl) or two adjacent positions on an aryl or heteroaryl system may be cyclised to form a 5, 6 or 7 membered carbocyclic or heterocyclic ring, itself optionally substituted with halogen or $C_1$-$C_6$alkyl. Further substituents for aryl or heteroaryl include arylcarbonylamino (where the aryl group is substituted by $C_1$-$C_6$alkyl or halogen), ($C_1$-$C_6$)alkoxycarbonylamino, ($C_1$-$C_6$)alkoxycarbonyl-N—($C_1$-$C_6$)alkylamino, aryloxycarbonylamino (where the aryl group is substituted by $C_1$-$C_6$alkyl or halogen), aryloxycarbonyl-N—($C_1$-$C_6$)alkylamino, (where the aryl group is substituted by $C_1$-$C_6$alkyl or halogen), arylsulphonylamino (where the aryl group is substituted by $C_1$-$C_6$alkyl or halogen), arylsulphonyl-N—($C_1$-$C_6$)alkylamino (where the aryl group is substituted by $C_1$-$C_6$alkyl or halogen), aryl-N—($C_1$-$C_6$)alkylamino (where the aryl group is substituted by $C_1$-$C_6$alkyl or halogen), arylamino (where the aryl group is substituted by $C_1$-$C_6$alkyl or halogen), heteroarylamino (where the heteroaryl group is substituted by $C_1$-$C_6$alkyl or halogen), heterocyclylamino (where the heterocyclyl group is substituted by $C_1$-$C_6$alkyl or halogen), aminocarbonylamino, $C_1$-$C_6$alkylaminocarbonylamino, di($C_1$-$C_6$)alkylaminocarbonylamino, arylaminocarbonylamino where the aryl group is substituted by $C_1$-$C_6$alkyl or halogen), aryl-N—($C_1$-$C_6$)alkylaminocarbonylamino where the aryl group is substituted by $C_1$-$C_6$alkyl or halogen), $C_1$-$C_6$alkylaminocarbonyl-N—($C_1$-$C_6$)alkylamino, di($C_1$-$C_6$)alkylaminocarbonyl-N—($C_1$-$C_6$)alkylamino, arylaminocarbonyl-N—($C_1$-$C_6$)alkylamino where the aryl group is substituted by $C_1$-$C_6$alkyl or halogen) and aryl-N—($C_1$-$C_6$)alkylaminocarbonyl-N—($C_1$-$C_6$)alkylamino where the aryl group is substituted by $C_1$-$C_6$alkyl or halogen).

For substituted heterocyclyl groups it is preferred that one or more substituents are independently selected from halogen, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfinyl, $C_1$-$C_6$alkylsulfonyl, nitro and cyano. It is to be understood that dialkylamino substituents include those where the dialkyl groups together with the N atom to which they are attached form a five, six or seven-membered heterocyclic ring which may contain one or two further heteroatoms selected from O, N or S and which is optionally substituted by one or two independently selected $C_1$-$C_6$alkyl groups. When heterocyclic rings are formed by joining two groups on an N atom, the resulting rings are suitably pyrrolidine, piperidine, thiomorpholine and morpholine each of which may be substituted by one or two independently selected $C_1$-$C_6$alkyl groups.

The invention relates also to the agriculturally acceptable salts which the compounds of formula I are able to form with transition metal, alkali metal and alkaline earth metal bases, amines, quaternary ammonium bases or tertiary sulfonium bases.

Among the transition metal, alkali metal and alkaline earth metal salt formers, special mention should be made of the hydroxides of copper, iron, lithium, sodium, potassium, magnesium and calcium, and preferably the hydroxides, bicarbonates and carbonates of sodium and potassium.

Examples of amines suitable for ammonium salt formation include ammonia as well as primary, secondary and tertiary $C_1$-$C_{18}$alkylamines, $C_1$-$C_4$hydroxyalkylamines and $C_2$-$C_4$alkoxyalkyl-amines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, di-isopropylamine, di-n-butylamine, di-n-amylamine, di-isoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, tri-isopropylamine, tri-n-butylamine, tri-isobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, isopropylamine and di-isopropylamine.

Preferred quaternary ammonium bases suitable for salt formation correspond, for example, to the formula $[N(R_a R_b R_c R_d)]OH$, wherein $R_a$, $R_b$, $R_c$ and $R_d$ are each independently of the others hydrogen, $C_1$-$C_4$alkyl. Further suitable tetraalkylammonium bases with other anions can be obtained, for example, by anion exchange reactions.

Preferred tertiary sulfonium bases suitable for salt formation correspond, for example, to the formula $[SR_e R_f R_g]OH$, wherein $R_e$, $R_f$ and $R_g$ are each independently of the others $C_1$-$C_4$ alkyl. Trimethylsulfonium hydroxide is especially preferred. Suitable sulfonium bases may be obtained from the reaction of thioethers, in particular dialkylsulfides, with alkylhalides, followed by conversion to a suitable base, for example a hydroxide, by anion exchange reactions.

It should be understood that in those compounds of formula I, where G is a metal, ammonium or sulfonium as mentioned above and as such represents a cation, the corresponding negative charge is largely delocalised across the O—C=C—C=O unit.

The compounds of formula I according to the invention also include hydrates which may be formed during the salt formation.

The latentiating groups G are selected to allow its removal by one or a combination of biochemical, chemical or physical processes to afford compounds of formula I where G is H before, during or following application to the treated area or plants. Examples of these processes include enzymatic cleavage, chemical hydrolysis and photolysis. Compounds bearing such groups G may offer certain advantages, such as improved penetration of the cuticula of the plants treated, increased tolerance of crops, improved compatibility or stability in formulated mixtures containing other herbicides, herbicide safeners, plant growth regulators, fungicides or insecticides, or reduced leaching in soils.

The latentiating group G is preferably selected from the groups $C_1$-$C_8$alkyl, $C_2$-$C_8$haloalkyl, phenyl$C_1$-$C_8$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), heteroaryl$C_1$-$C_8$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_8$alkenyl, $C_3$-$C_8$haloalkenyl, $C_3$-$C_8$alkynyl, $C(X^a)$—$R^a$, $C(X^b)$—$X^c$—$R^b$, $C(X^d)$—N$(R^c)$—$R^d$, —$SO_2$—$R^e$, —$P(X^e)(R^f)$—$R^g$ or $CH_2$—$X^f$—$R^{11}$ wherein $X^a$, $X^b$, $X^c$, $X^d$, $X^e$ and $X^f$ are independently of each other oxygen or sulfur;

$R^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$) alkyl, $C_1$-$C_5$alkoxy($C_1$-$C_5$)alkyl, $C_3$-$C_5$alkenyloxy($C_1$-$C_5$) alkyl, $C_3$—($C_1$-$C_5$)oxyalkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$) alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkyl-carbonyl-N—($C_1$-$C_5$)alkylamino($C_1$-$C_5$)alkyl, $C_3$-$C_8$-trialkylsilyl($C_1$-$C_5$)alkyl, phenyl($C_1$-$C_5$)alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, $R^b$ is $C_1$-$C_{18}$alkyl, $C_3$-$C_{18}$alkenyl, $C_3$-$C_{18}$alkynyl, $C_2$-$C_{18}$haloalkyl, $C_1$-$C_{10}$cyanoalkyl, $C_1$-$C_{10}$nitroalkyl, $C_2$-$C_{18}$-aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$) alkyl, $C_1$-$C_5$alkoxy($C_1$-$C_5$)alkyl, $C_3$-$C_5$alkenyloxy($C_1$-$C_5$) alkyl, $C_3$-$C_5$alkynyloxy($C_1$-$C_5$)alkyl, $C_1$-$C_5$alkylthio($C_1$-$C_5$) alkyl, $C_1$-$C_5$alkylsulfinyl($C_1$-$C_5$)alkyl, $C_1$-$C_5$alkylsulfonyl ($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkyl-carbonyl-N—($C_1$-$C_5$)alkylamino($C_1$-$C_5$)alkyl, $C_3$-$C_6$-trialkylsilyl($C_1$-$C_5$)alkyl, phenyl($C_1$-$C_5$)alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkyl-thio, $C_1$-$C_3$alkylsulfinyl, $C_1$-$C_3$alkylsulfonyl, halogen, cyano, or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$haloalkyl, $C_1$-$C_{10}$cyanoalkyl, $C_1$-$C_{10}$-nitroalkyl, $C_1$-$C_{10}$-aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$-trialkylsilyl($C_1$-$C_5$)alkyl, phenyl($C_1$-$C_5$)alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro or $C_3$-$C_7$cycloalkylamino, di-$C_3$-$C_7$cycloalkylamino or $C_3$-$C_7$cycloalkoxy or $R^c$ and $R^d$ may join together to form a 3-7 membered ring, optionally containing one heteroatom selected from O or S, $R^e$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$-trialkylsilyl($C_1$-$C_5$)alkyl, phenyl($C_1$-$C_5$)alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$alkoxy, $C_1$-$C_{10}$haloalkoxy, $C_1$-$C_5$alkylamino or $C_2$-$C_8$dialkylamino, $R^f$ and $R^g$ are are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$haloalkyl, $C_1$-$C_{10}$cyanoalkyl, $C_1$-$C_{10}$-nitroalkyl, $C_1$-$C_{10}$-aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$-trialkylsilyl($C_1$-$C_5$)alkyl, phenyl($C_1$-$C_5$)alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$haloalkoxy, $C_1$-$C_5$alkylamino or $C_2$-$C_8$dialkylamino, benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro, and $R^h$ is $C_1$-$C_{10}$alkyl, $C_3$-$C_{10}$alkenyl, $C_3$-$C_{10}$alkynyl, $C_1$-$C_{10}$haloalkyl, $C_1$-$C_{10}$cyanoalkyl, $C_1$-$C_{10}$nitroalkyl, $C_2$-$C_8$-aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_8$-trialkylsilyl($C_1$-$C_5$)alkyl, phenyl($C_1$-$C_5$)alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl($C_1$-$C_5$)alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), phenoxy($C_1$-$C_5$)alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryloxy($C_1$-$C_5$)alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro, or heteroaryl, or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro.

In particular, the latentiating group G is a group —C($X^a$)—$R^a$ or —C($X^b$)—$X^c$—$R^b$, and the meanings of $X^a$, $R^a$, $X^b$, $X^c$ and $R^b$ are as defined above.

It is preferred that G is hydrogen, an alkali metal or alkaline earth metal, where hydrogen is especially preferred.

Depending on the nature of the substituents, compounds of formula I may exist in different isomeric forms. For example, when G is hydrogen and $R^4$ and $R^5$ are different from $R^6$ and $R^7$, compounds of formula I may exist in different tautomeric forms:

Preferably, in the compounds of formula I, A is phenyl, naphthyl, a 5- or a 6-membered heteroaryl or a bicyclic 8- to 10-membered heteroaryl, Preferably, in the compounds of formula I, A is substituted by halogen, $C_1$-$C_4$alkyl, $C_1$-$C_4$haloalkyl, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, nitro, cyano, $C_3$-$C_6$cycloalkyl, $C_1$-$C_3$alkylcarbonyl, $C_1$-$C_4$alkoxycarbonyl, aminocarbonyl, $C_1$-$C_3$alkylaminocarbonyl, di-$C_1$-$C_3$alkylaminocarbonyl, $C_1$-$C_3$alkylaminocarbonyloxy, di-$C_1$-$C_3$alkylaminocarbonyloxy, aminothiocarbonyl, $C_1$-$C_3$alkylaminothiocarbonyl, di$C_1$-$C_3$alkylaminothiocarbonyl, $C_1$-$C_4$alkylcarbonylamino, $C_3$-$C_6$cycloalkylcarbonylamino, $C_1$-$C_4$alkoxycarbonylamino, $C_1$-$C_4$alkylthiocarbonylamino, $C_1$-$C_3$alkoxy$C_1$-$C_3$alkyl, $C_1$-$C_6$alkylthio$C_1$-$C_6$alkyl, $C_1$-$C_6$alkylsulfinyl$C_1$-$C_6$alkyl, $C_1$-$C_6$alkylsulfonyl$C_1$-$C_6$alkyl, $C_1$-$C_3$alkylsulfonyloxy, $C_1$-$C_3$haloalkylsulfonyloxy or di$C_1$-$C_6$alkylaminosulfonyl, or 2 substituents on adjacent carbon atoms of A together form a $C_3$-$C_4$alkylene, wherein 1 or 2 methylene groups are optionally substituted by halogen, or wherein 1 or 2 of these methylene groups are replaced by oxygen.

More preferably, A is phenyl, naphthyl, pyridyl, pyrazinyl, pyrimidinyl, pyridazinyl, benzothiazolyl, benzoxazolyl, cinnolinyl, quinolinyl, quinazolinyl, quinoxalinyl or benzotriazinyl in each case substituted by halogen, methyl, ethyl, trifluoromethyl, methoxy, difluoromethoxy, trifluoromethoxy, nitro or cyano.

$R^1$ is preferably methyl, ethyl, n-propyl, cyclopropyl, halogen, halomethoxy or haloethoxy, especially ethyl.

Preferably, $R^2$ and $R^3$ are independently of each other hydrogen, methyl or halogen, especially hydrogen.

Preferably, $R^4$, $R^5$, $R^6$ and $R^7$ are independently of each other hydrogen, $C_1$-$C_6$alkyl, $C_1$-$C_4$haloalkyl, $C_1$-$C_4$alkoxy$C_1$-$C_4$alkyl, optionally substituted five- or six-membered heterocyclyl, or optionally substituted five- or six-membered heterocyclyl$C_1$-$C_2$alkyl, or $R^4$ and $R^5$, or $R^6$ and $R^7$, together with the atoms to which they are bonded form an optionally substituted saturated or unsaturated five- or six-membered carbocyclyl or heterocyclyl which contains one or two oxygen atoms, or $R^5$ and $R^6$, with the atoms to which they are bonded form an optionally substituted five- or six-membered saturated or unsaturated carbocyclyl which is optionally bridged by $C_1$-$C_2$ alkyldiyl or by oxygen.

More preferably, $R^4$ and $R^7$ are hydrogen and $R^5$ and $R^6$, with the atoms to which they are bonded form a six-mem-

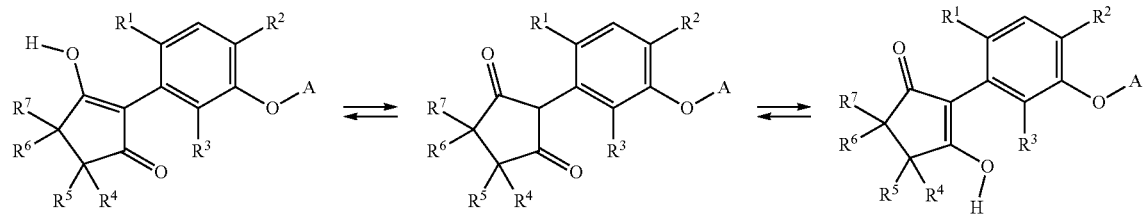

bered saturated or unsaturated carbocyclyl which is bridged by $C_1$-$C_2$ alkyldiyl or by oxygen.

Particularly preferred compounds of the formula (I) are those wherein $R^1$ is ethyl or cyclopropyl, $R^2$ and $R^3$ are hydrogen, $R^4$, $R^7$, $R^5$ and $R^6$ are hydrogen, or $R^4$ and $R^7$ are hydro- This invention covers all such isomers and tautomers and mixtures thereof in all proportions. Also, when substituents contain double bonds, cis- and trans-isomers can exist. These isomers, too, are within the scope of the claimed compounds of the formula I.

gen and $R^5$ and $R^6$, with the atoms to which they are bonded, form a six-membered saturated carbocyclyl which is bridged by $C_1$-$C_2$ alkyldiyl or by oxygen, A is phenyl substituted by fluoro, chloro, bromo, methyl, trifluoromethyl, methoxy, trifluoromethoxy, cyano or nitro, or A is pyridyl, pyrimidinyl, pyrazinyl, benzothiazolyl, quinolinyl or quinoxalinyl in each case substituted by fluoro, chloro, bromo, trifluoromethyl, methoxy, or nitro, and G is hydrogen.

A compound of formula I wherein G is $C_1$-$C_8$alkyl, $C_2$-$C_8$haloalkyl, phenyl$C_1$-$C_8$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsufinyl, $C_1$-$C_3$alkylsulfonyl, halogen, cyano or by nitro), heteroaryl$C_1$-$C_8$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsufinyl, $C_1$-$C_3$alkylsulfonyl, halogen, cyano or by nitro), $C_3$-$C_8$alkenyl, $C_3$-$C_8$haloalkenyl, $C_3$-$C_8$alkynyl, $C(X^a)$—$R^a$, $C(X)$—$X^c$—$R^b$, $C(X^d)$—$N(R^c)$—$R^d$, —$SO_2$—$R^e$, —$P(X^e)(R^f)$—$R^g$ or $CH_2$—$X^f$—$R^h$ where $X^a$, $X^b$, $X^c$, $X^d$, $X^e$, $X^f$, $R^a$, $R^b$, $R^c$, $R^d$, $R^e$, $R^f$, $R^g$ and $R^h$ are as defined above may be prepared by treating a compound of formula (A), which is a compound of formula (I) wherein G is H, with a reagent G-Z, wherein G-Z is an alkylating agent such as an alkyl halide (the definition of alkyl halides includes simple $C_1$-$C_8$ alkyl halides such as methyl iodide and ethyl iodide, substituted alkyl halides such as chloromethyl alkyl ethers, Cl—$CH_2$—$X^f$—$R^h$, wherein $X^f$ is oxygen, and chloromethyl alkyl sulfides Cl—$CH_2$—$X^f$—$R^h$, wherein $X^f$ is sulfur), a $C_1$-$C_8$alkyl sulfonate, or a di($C_1$-$C_8$alkyl) sulfate, or with a $C_3$-$C_8$alkenyl halide, or with a $C_3$-$C_8$alkynyl halide, or with an acylating agent such as a carboxylic acid, HO—$C(X^a)R^a$, wherein $X^a$ is oxygen, an acid chloride, Cl—$C(X^a)R^a$, wherein $X^a$ is oxygen, or acid anhydride, $[R^aC(X^a)]_2O$, wherein $X^a$ is oxygen, or an isocyanate, $R^cN$=$C$=$O$, or a carbamoyl chloride, Cl—$C(X^d)$—$N(R^c)$—$R^d$ (wherein $X^d$ is oxygen and with the proviso that neither $R^c$ or $R^d$ is hydrogen), or a thiocarbamoyl chloride Cl—$(X^d)$—$N(R^c)$—$R^d$ (wherein $X^d$ is sulfur and with the proviso that neither $R^c$ or $R^d$ is hydrogen) or a chloroformate, Cl—$C(X^h)$—$X^c$—$R^h$, (wherein $X^b$ and $X^c$ are oxygen), or a chlorothioformate Cl—$C(X^h)$—$X^c$—$R^h$ (wherein $X^b$ is oxygen and $X^c$ is sulfur), or a chlorodithioformate Cl—$C(X^h)$—$X^c$—$R^h$, (wherein $X^b$ and $X^c$ are sulfur), or an isothiocyanate, $R^cN$=$C$=$S$, or by sequential treatment with carbon disulfide and an alkylating agent, or with a phosphorylating agent such as a phosphoryl chloride, Cl—$P(X^e)(R^f)$—$R^9$ or with a sulfonylating agent such as a sulfonyl chloride Cl—$SO_2$—$R^e$, preferably in the presence of at least one equivalent of base.

Where substituents $R^4$ and $R^5$ are not equal to substituents $R^6$ and $R^7$, these reactions may produce, in addition to a compound of formula (I), a second compound of formula ($I_A$).

This invention covers both a compound of formula (I) and a compound of formula ($I_A$), together with mixtures of these compounds in any ratio.

The O-alkylation of cyclic 1,3-diones is known; suitable methods are described, for example, by T. Wheeler, U.S. Pat. No. 4,436,666. Alternative procedures have been reported by M. Pizzorno and S. Albonico, Chem. Ind. (London), (1972), 425-426; H. Born et al., J. Chem. Soc., (1953), 1779-1782; M. G. Constantino et al., Synth. Commun., (1992), 22 (19), 2859-2864; Y. Tian et al., Synth. Commun., (1997), 27 (9), 1577-1582; S. Chandra Roy et al., Chem. Letters, (2006), 35 (1), 16-17; P. K. Zubaidha et al., Tetrahedron Lett., (2004), 45, 7187-7188.

The O-acylation of cyclic 1,3-diones may be effected by procedures similar to those described, for example, by R. Haines, U.S. Pat. No. 4,175,135, and by T. Wheeler, U.S. Pat. No. 4,422,870, U.S. Pat. No. 4,659,372 and U.S. Pat. No. 4,436,666. Typically diones of formula (A) may be treated with an acylating agent preferably in the presence of at least one equivalent of a suitable base, and optionally in the presence of a suitable solvent. The base may be inorganic, such as an alkali metal carbonate or hydroxide, or a metal hydride, or an organic base such as a tertiary amine or metal alkoxide. Examples of suitable inorganic bases include sodium carbonate, sodium or potassium hydroxide, sodium hydride, and suitable organic bases include trialkylamines, such as trimethylamine and triethylamine, pyridines or other amine bases such as 1,4-diazobicyclo[2.2.2]-octane and 1,8-diazabicyclo [5.4.0]undec-7-ene. Preferred bases include triethylamine and pyridine. Suitable solvents for this reaction are selected to be compatible with the reagents and include ethers such as tetrahydrofuran and 1,2-dimethoxyethane and halogenated solvents such as dichloromethane and chloroform. Certain bases, such as pyridine and triethylamine, may be employed successfully as both base and solvent. For cases where the acylating agent is a carboxylic acid, acylation is preferably effected in the presence of a known coupling agent such as 2-chloro-1-methylpyridinium iodide, N,N'-dicyclohexylcarbodiimide, 1-(3-dimethylaminopropyl)-3-ethylcarbodiimide and N,N'-carbodiimidazole, and optionally in the presence of a base such as triethylamine or pyridine in a suitable solvent such as tetrahydrofuran, dichloromethane or acetonitrile. Suitable procedures are described, for example, by W. Zhang and G. Pugh, Tetrahedron Lett., (1999), 40 (43), 7595-7598; T. Isobe and T. Ishikawa, J. Org. Chem., (1999), 64 (19), 6984-6988 and K. Nicolaou, T. Montagnon, G. Vassilikogiannakis, C. Mathison, J. Am. Chem. Soc., (2005), 127(24), 8872-8888.

Phosphorylation of cyclic 1,3-diones may be effected using a phosphoryl halide or thiophosphoryl halide and a base by procedures analogous to those described by L. Hodakowski, U.S. Pat. No. 4,409,153.

Sulfonylation of a compound of formula (A) may be achieved using an alkyl or aryl sulfonyl halide, preferably in

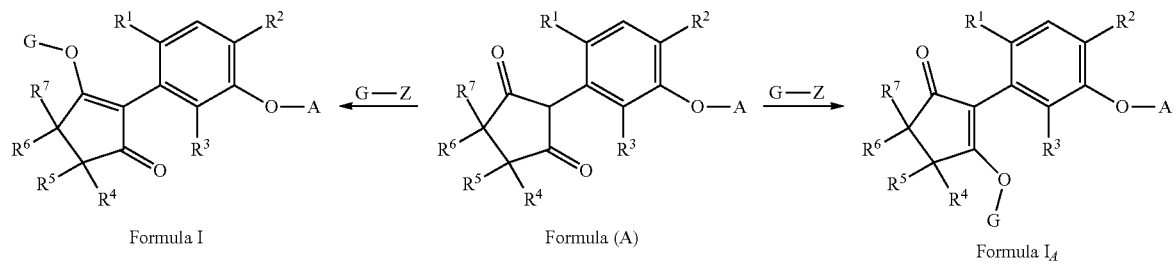

Formula I            Formula (A)            Formula $I_A$ the presence of at least one equivalent of base, for example by the procedure of C. Kowalski and K. Fields, J. Org. Chem., (1981), 46, 197-201.

A compound of formula (A) may be prepared via the cyclisation of a compound of formula (B), preferably in the presence of an acid or base, and optionally in the presence of a suitable solvent, by analogous methods to those described by T. Wheeler, U.S. Pat. No. 4,283,348. The compounds of the formula (B) have been particularly designed as intermediates in the synthesis of the compounds of the formula I. Compounds of formula (B) wherein R is hydrogen or $C_1$-$C_4$alkyl, (especially methyl, ethyl and tert-butyl) may be cyclised under acidic conditions, preferably in the presence of a strong acid such as sulfuric acid, polyphosphoric acid or Eaton's reagent, optionally in the presence of a suitable solvent such as acetic acid, toluene or dichloromethane.

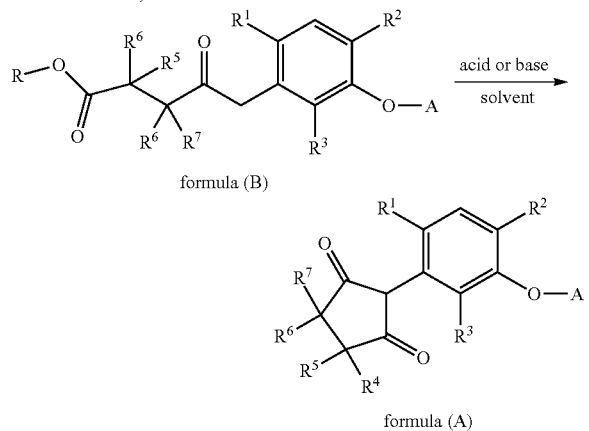

formula (B)

formula (A)

A compound of formula (B) wherein R is alkyl (preferably methyl or ethyl) may be cyclised under acidic or basic conditions, preferably under basic conditions in the presence of at least one equivalent of a strong base such as potassium tert-butoxide, lithium diisopropylamide, sodium bis(trimethylsilyl)amide or sodium hydride and in a solvent such as tetrahydrofuran, toluene, dimethylsulfoxide or N,N-dimethylformamide.

A compound of formula (B), wherein R is H may be esterified to a compound of formula (B), wherein R is alkyl, under known conditions (for example by treatment with an alcohol, R—OH, in the presence of an acid catalyst).

A compound of formula (B), wherein R is H may be prepared by hydrolysis of a compound of formula (C) wherein R is H or alkyl and R' is alkyl (preferably methyl or ethyl), followed by acidification of the reaction mixture to effect decarboxylation. Alternatively, a compound of formula (B), wherein R is alkyl may be prepared from a compound of formula (C), wherein R is alkyl and R' is methyl or ethyl (preferably methyl) through a Krapcho decarboxylation procedure under known conditions using known reagents (see for example G. Quallich, P. Morrissey, Synthesis, (1993), (1), 51-53).

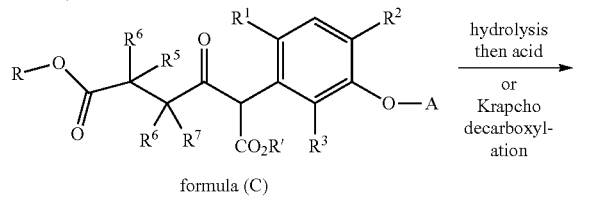

formula (C)

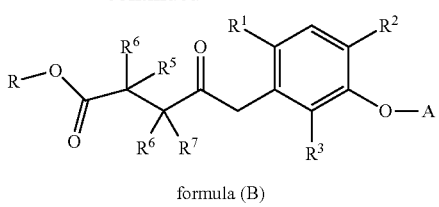

formula (B)

A compound of formula (C), wherein R is H, may be prepared by treating a compound of formula (D) with a suitable base (such as potassium tert-butoxide, sodium bis(trimethylsilyl)amide and lithium diisopropylamide) in a suitable solvent (such as tetrahydrofuran or toluene) at a suitable temperature (between −80° C. and 30° C.) and reacting the resulting anion with a suitable anhydride of formula (E):

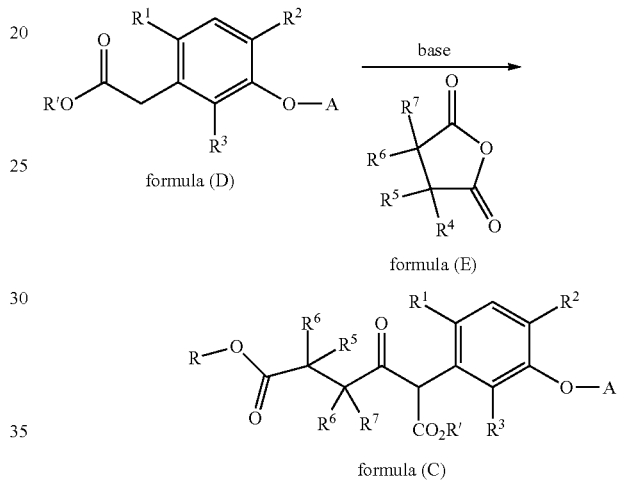

formula (D)

formula (E)

formula (C)

Compounds of formula (D) are known, or may be made by known methods from commercially available starting materials (see, for example, H. Ishibashi et al., Chem. Pharm. Bull., (1991), 39 (11), 2878-2882; R. Kirsten et al., EP338306 A2; W. Marshall, U.S. Pat. No. 3,649,679) or may be made by similar methods from known compounds. Compounds of formula (E) are known, or may be made by known methods from commercially available starting materials (see, for example, J. Rowley et al., J. Am. Chem. Soc., (2007), 129 (16), 4948-4960; J. Pohlmann et al., Bioorg. Med. Chem. Lett., (2005), 15(4), 1189-1192; L. Fieser and E. Martin., Org. Synth. Coll. Vol. II, (1943), 560-561).

In an alternative approach, a compound of formula (A) may be prepared by cross-coupling a dione of formula (F) with an aryl halide of formula (G). Similar couplings are known in the literature (see for example, S. Buchwald et al., J. Am. Chem. Soc. (2000), 122, 1360-1370; B. Hong et al. WO 2005/000233).

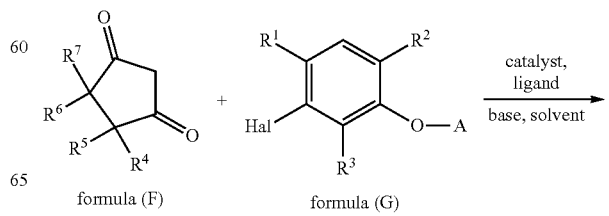

formula (F)     formula (G)

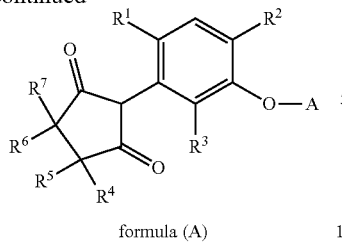

formula (A)

Compounds of formula (F) are known, or may be made by known methods from known compounds (see, for example M. Nishizawa et al., Synlett., (2006), 4, 642-644; J. Mascarenas et al., Org. Lett., (2003), 5 (11), 1975-1977; A. Demir and D. Enders, Journal fuer Praktische Chemie, (1997), 339 (6), 553-563; B. Zwanenburg et al., Tetrahedron (1989), 45 (22), 7109-7133; A. Demir and D. Enders, Tetrahedron Lett., (1989), 30 (13), 1705-1708; E. Guntrum et al., Synthesis, (1986), (11), 921-925, and by M. Oda et al., Chem. Lett., (1977), 6 (3), 307-310).

In an alternative approach, a compound of formula I, wherein G is $C_1$-$C_4$alkyl may be prepared by reacting a compound of formula (H) (wherein G is $C_{1-4}$ alkyl, and Hal is a halogen, preferably bromine or iodine), with an arylboronic acid of formula (I) in the presence of a suitable palladium catalyst (for example 0.001-50% palladium(II) acetate with respect to compound (H)) and a base (for example 1 to 10 equivalents potassium phosphate with respect to compound (H)) and preferably in the presence of a suitable ligand (for example 0.001-50% (2-dicyclohexyl-phosphino)-2',6'-dimethoxybiphenyl with respect to compound (U)), and in a suitable solvent (for example toluene), preferably between 25° C. and 200° C. Similar couplings are known in the literature (see for example, Y. Song, B. Kim and J.-N. Heo, Tetrahedron Letters (2005), 46 (36), 5987-5990.

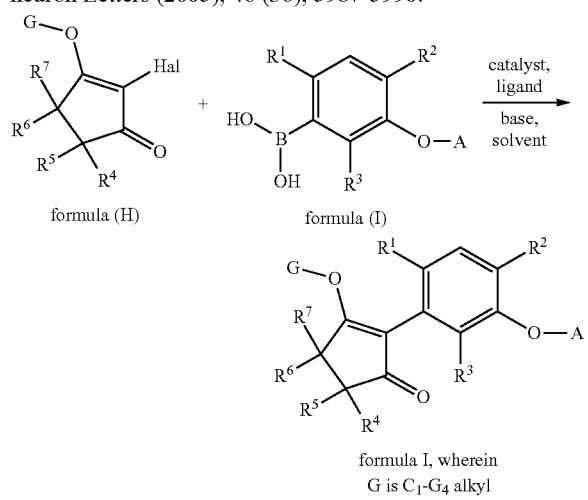

formula I, wherein G is $C_1$-$G_4$ alkyl

A compound of formula (H) may be prepared by halogenating a compound of formula (F), followed by reaction of the resulting halide of formula (J) with a $C_1$-$C_4$alkyl halide or tri-$C_1$-$C_4$-alkylorthoformate under known conditions, for example by the procedures of R. Shepherd and A. White (J. Chem. Soc. Perkin Trans. 1 (1987), 2153-2155) and Y.-L. Lin et al. (Bioorg. Med. Chem. (2002), 10, 685-690). Alternatively, a compound of formula (H) may be prepared by reacting a compound of formula (F), with a $C_1$-$C_4$ alkyl halide or a tri-$C_1$-$C_4$-alkylorthoformate, and halogenating the resulting enone of formula (K) under known conditions (see for example Y. Song, B. Kim and J.-N. Heo, Tetrahedron Letters (2005), 46(36), 5987-5990).

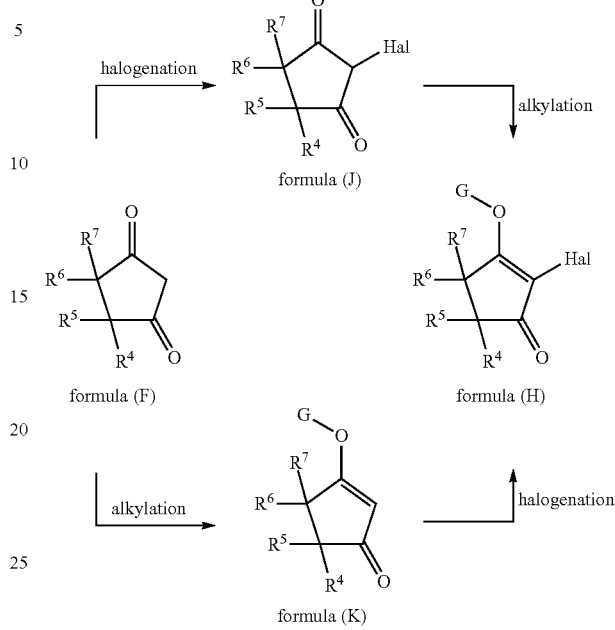

In a further approach, a compound of formula (A) may be prepared by reacting a compound of formula (F) with an aryllead tricarboxylate, in the presence of a suitable ligand and in a suitable solvent. Similar reactions are described in the literature (for example see, M. Muehlebach et al., WO08/071,405; J. Pinhey, B. Rowe, Aust. J. Chem., (1979), 32, 1561-6; J. Morgan, J. Pinhey, J. Chem. Soc. Perkin Trans. 1, (1990), 3, 715-20). Preferably the aryllead tricarboxylate is an aryllead triacetate of formula (L). Preferably the ligand is a nitrogen containing heterocycle such as N,N-dimethylamino-pyridine, 1,10-phenanthroline pyridine, bipyridine, or imidazole, and one to ten equivalents of ligand with respect to a compound of formula (F) is preferably used. Most preferably the ligand is N,N-dimethylaminopyridine. The solvent is preferably chloroform, dichloromethane or toluene, most preferably chloroform, or a mixture of chloroform and toluene. Preferably the reaction is conducted at a temperature of −10° C. to 100° C., most preferably at 40-90° C.).

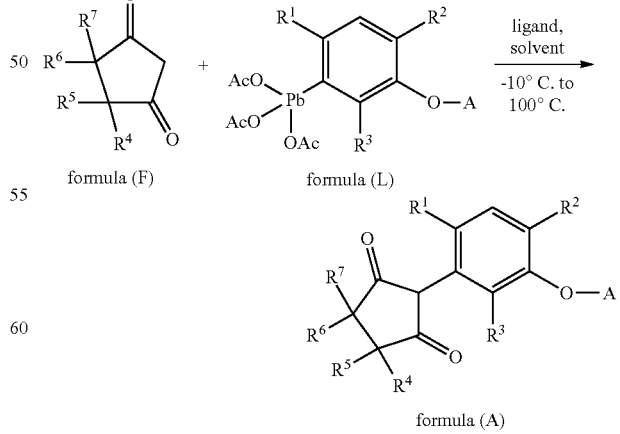

A compound of formula (L) may be prepared from a compound of formula (I) by treatment with lead tetraacetate in a suitable solvent (for example chloroform) at 25° C. to 100° C. (preferably 25-50° C.), and optionally in the presence of a catalyst such as mercury diacetate, according to procedures described in the literature (for example see, M. Muehlebach et al., WO08/071,405; K. Shimi, G. Boyer, J-P. Finet and J-P. Galy, Letters in Organic Chemistry, (2005), 2, 407-409; J. Morgan and J. Pinhey, J. Chem. Soc. Perkin Trans. 1; (1990), 3, 715-720).

Aryl halides of formula (G) are known compounds or may be made by known methods from known compounds (See, for example, R. Clark, J. Agric. Food Chem., (1996), 44 (11), 3643-3652; T. Okamato and J. Bunnett, J. Am. Chem. Soc., (1956), 78, 5357-5362; H. Scarborough and J. Sweeten, J. Chem. Soc., (1934), 52-56).

In a further approach, a compound of formula (A) may be prepared by derivatisation of a compound of formula (M), which is a compound of formula I wherein G is hydrogen and $R^5$ and $R^6$ together form a bond. Compounds of formula (M) are α,β-unsaturated cyclic diones and undergo reactions in the presence of reagents known to effect transformations of α,β-unsaturated ketones to give additional compounds of formula (A).

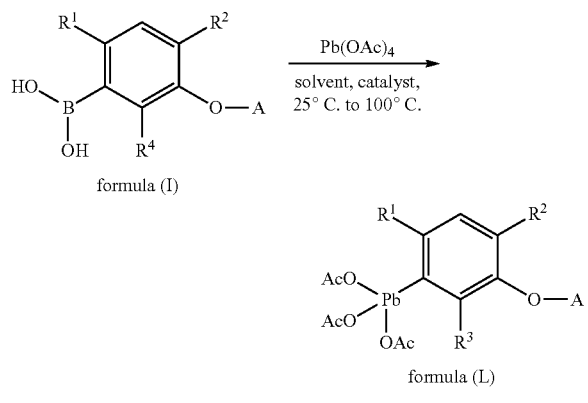

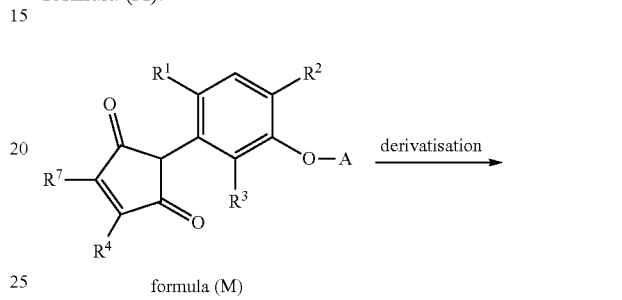

An aryl boronic acid of formula (I) may be prepared from an aryl halide of formula (G), wherein Hal is bromine or iodine by known methods (see, for example, W. Thompson and J. Gaudino, J. Org. Chem., (1984), 49, 5237-5243 and R. Hawkins et al., J. Am. Chem. Soc., (1960), 82, 3053-3059). Thus an aryl halide of formula (G) may be treated with an alkyl lithium or alkyl magnesium halide at low temperature, and the aryl magnesium or aryl lithium reagent obtained is allowed to react with a trialkyl borate, $B(OR")_3$, preferably trimethylborate (R" is methyl), to give an aryl dialkylboronate which may be hydrolysed to the desired boronic acid of formula (I) under acidic conditions. Alternatively the same overall transformation of compound (G) to compound (I) may be achieved through a palladium-catalysed borylation reaction under known conditions using known reagents (see for example T. Ishiyama, M. Murata, N. Miyaura, J. Org. Chem. (1995), 60, 7508-7501; and K. L. Billingsley, T. E. Barder, S. L. Buchwald, Angew. Chem. Int. Ed. (2007), 46, 5359-5363), followed by hydrolysis of the intermediate boronate ester.

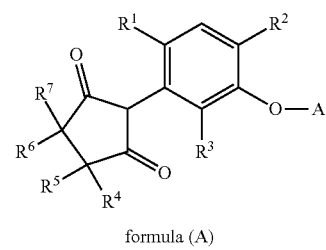

formula (A)

For example, a compound of formula (M) may be reacted with a suitable nucleophile, Nuc-H, optionally in the presence of a suitable base and a suitable solvent to give compounds of formula (A) wherein $R^5$ is the group Nuc resulting from nucleophilic attack and $R^6$ is hydrogen.

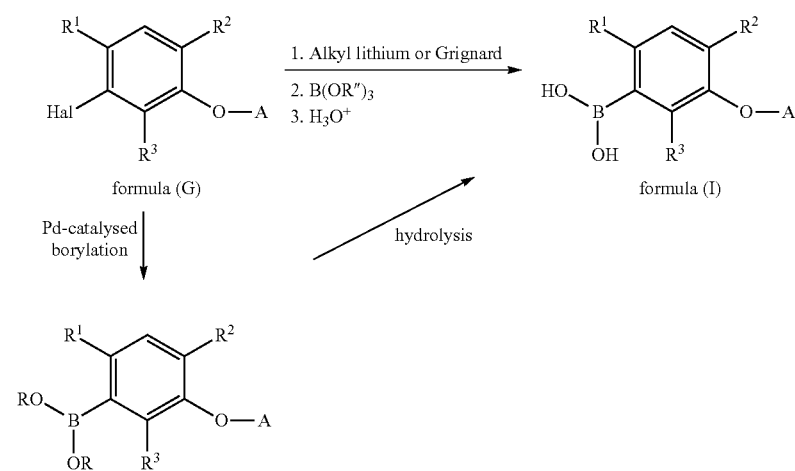

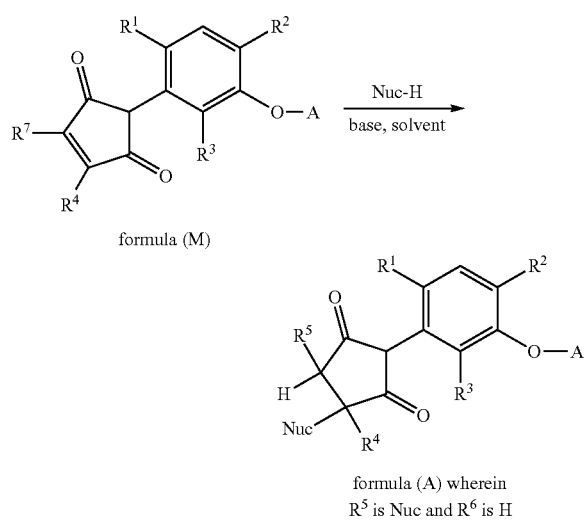

formula (M)

formula (A) wherein
$R^5$ is Nuc and $R^6$ is H

Suitable nucleophiles, Nuc-H, include, but are not limited to, optionally substituted $C_1$-$C_6$alkylthiols, optionally substituted arylthiols, optionally substituted heteroarylthiols optionally substituted $C_1$-$C_6$alkyl alcohols and optionally substituted $C_3$-$C_7$cyclic alcohols (including $C_3$-$C_6$ alicyclic alcohols, 4-6 membered heterocyclic alcohols, phenols and heteroaromatic alcohols).

A compound of formula (M) will also participate in cycloaddition reactions under suitable conditions to afford additional compounds of formula (A).

For example, a compound of formula (M) may be reacted with a suitable 1,3-diene of formula (N), wherein $R_a$ represents a suitable substituent (such as $C_1$-$C_4$alkyl, $C_1$-$C_4$alkoxy or tri-$C_1$-$C_4$alkylsilyloxy), and n is 0, 1 or 2, under suitable conditions to give a compound of formula (A) wherein $R^5$ and $R^6$ together with the atoms to which they are joined form an unsaturated six-membered ring.

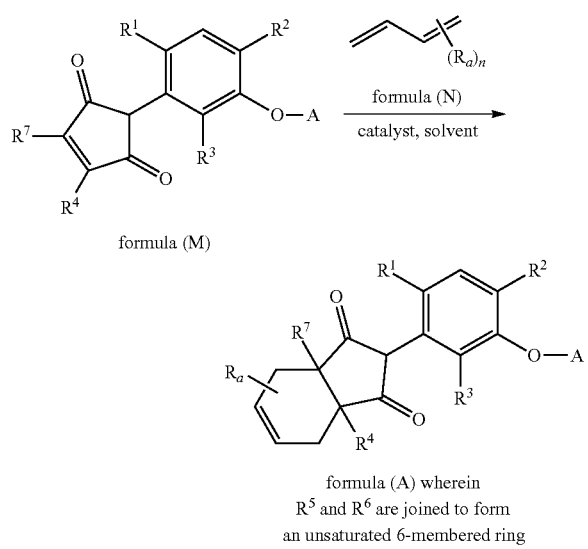

formula (M)

formula (A) wherein
$R^5$ and $R^6$ are joined to form
an unsaturated 6-membered ring Suitable 1,3-dienes include 1,3-butadiene (or an equivalent, for instance 2,5-dihydrothiophene-1,1-dioxide), and substituted 1,3-butadienes. Similarly, a compound of formula (M) may also be reacted with cyclic dienes of formula (O) such as cyclopentadiene (W is —$CH_2$— and $R_b$ is hydrogen), substituted cyclopentadienes, cyclohexa-1,3-diene (W is —$CH_2$—$CH_2$— and $R_b$ is hydrogen), substituted cyclopentadienes, furan (W is oxygen and $R_b$ is hydrogen) and substituted furans.

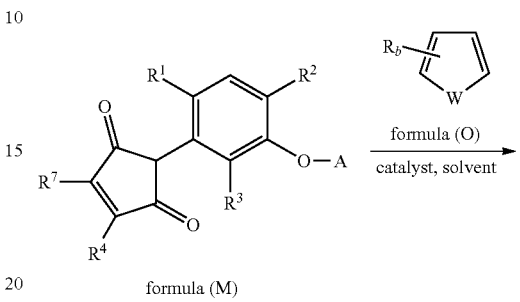

formula (M)

formula (A) wherein $R^5$ and $R^6$
are joined to form an unsaturated
ring which is further bridged Those skilled in the art will appreciate that cyclic dienes of formula (O) bearing a wide variety of substituents $R_b$ will undergo cycloaddition reactions with a compound of formula (M) to give new compounds of formula (A), under appropriate conditions (for example, in the presence or absence of Lewis acid catalysts, such as aluminium chloride, bismuth (III) chloride, bismuth(III) trifluoromethanesulfonate, boron trifluoride, cerium(III) chloride, copper(I) trifluoromethanesulfonate, diethylaluminium chloride, hafnium(IV) chloride, iron(III) chloride, lithium perchlorate, lithium trifluoromethanesulfonate, magnesium bromide, magnesium iodide, scandium(III) trifluoromethanesulfonate, tin(IV) chloride, titanium(IV) chloride, titanium(IV) isopropoxide, trimethyl aluminium, N-trimethylsilyl-bis(trifluoromethanesulfonyl)imide, trimethylsilyl trifluoromethane-sulfonate, ytterbium(III) trifluoromethanesulfonate, zinc iodide and zirconium(IV) chloride, and in the presence or absence of solvents such as chloroform, dichloromethane, diethyl ether, ethanol, methanol, perfluorinated alkanes such as perfluorohexane, toluene, water, and ionic liquids such as 1-butyl-3-methylimidazolium tetrafluoroborate and 1-butyl-3-methylimidazolium hexafluorophosphate, and at normal atmospheric pressure or under high pressure conditions), as described, for example by G. Silvero et al., Tetrahedron (2005), 61, 7105-7111; I. Hemeon et al., Synlett, (2002), 11, 1815-1818; S. Otto and J. Engberts, Pure Appl. Chem. (2000), 72 (7), 1365-1372; R. Breslow, Acc. Chem. Res., (1991), 24 (6), 159-164; K. Hara et al., Org. Lett., (2005), 7 (25), 5621-5623; J, Auge et al., Synlett, (2000), 6, 877-879, B. Garrigues and A. Oussaid, J. Organometallic Chem., (1989), 585, 253-255; B. Mathieu and L. Ghosez, Tetrahedron Lett., (1997), 38 (31), 5497-5500; M. Ordoñez et al., Tetrahedron Asymmetry, (1996), 7 (9), 2675-2686; S. Kobayashi et al., Tetrahedron Lett., (1993), 34 (23), 3755-3758; C. Cativiela et al., U. Pindur et al., Chem. Rev., (1993), 93, 741-761; Tetrahedron, (1992), 48 (31), 6467-6476; J. Aubé et al., J. Am. Chem. Soc., (1992), 114, 5466-5467; S. Danishefsky and M. Bednarski, Tetrahedron Lett., (1985), 26 (21), 2507-2508 and references therein); Q. Chu, W. Zhang and D. Curran, Tetrahedron Lett., (2006), 47, 9287-9290; K. Ishihara and K. Nakano, J. Am. Chem. Soc., (2005), 127 (30), 10504-10505; and A. Northrup and D. MacMillan, (2002), J. Am. Chem. Soc., 124 (11), 2458-2460).

The reaction of compounds of formula (M) with compounds of formula (N) or with compounds of formula (O) provides compounds of formula (A) wherein $R^5$ and $R^6$ are joined to form an unsaturated ring. Such compounds are alkenes, which may undergo reactions typical of alkenes (for example reduction, halogenation or cross-coupling) to produce further compounds of formula (A).

A compound of formula (M) may also act as a dipolarophile and will therefore undergo a range of 3+2 cycloaddition reactions with suitable dipolar reagents under suitable conditions. For example, a compound of formula (M) may react with a nitrile oxide of formula (P), wherein $R_c$ is a suitable substituent (for example $C_1$-$C_4$alkyl or aryl), or with a nitrone of formula (O), wherein $R_e$, $R_f$ and $R_g$ are suitable substituents (for example hydrogen or $C_1$-$C_4$alkyl), under appropriate conditions to give further compounds of formula (A), wherein $R^4$ and $R^7$ together with the atoms to which they are attached form an isoxazoline or isoxazolidine ring respectively.

Suitable conditions for effecting 3+2 cycloadditions are described, for example, by L. Deng and Y. Hu, Synth. Commun. (2007), 37, 157-163; E. Kantorowski et al., J. Org. Chem., (1998), 63, 5272-5274; and by V. Jager and I. Müller, Tetrahedron (1985), 41 (17), 3519-3528.

A compound of formula (M), may be prepared by oxidising a compound of formula (R) in a suitable solvent such as toluene, acetone, chloroform, dichloromethane or 1,4-dioxane. A wide range of oxidants is suitable for effecting this transformation, including inorganic oxidants such as chromium trioxide, pyridinium dichromate, manganese dioxide and aluminium alkoxides such as aluminium isopropoxide, as well as organic oxidants such as 2,3-dichloro-5,6-dicyano-p-benzoquinone and hypervalent iodine oxidants such as 1,1,1,-tris(acetyloxy)-1,1-dihydro-1,2-benziodoxol-3-(1H)-one (Dess-Martin periodinane), Suitable procedures are described, for example, by K. Saito and H. Yamachika, U.S. Pat. No. 4,371,711. and by G. Piancatelli et al., Tetrahedron (1978), 34, 2775. The use of chromium trioxide in a mixture of sulfuric acid and acetone (Jones reagent) is preferred.

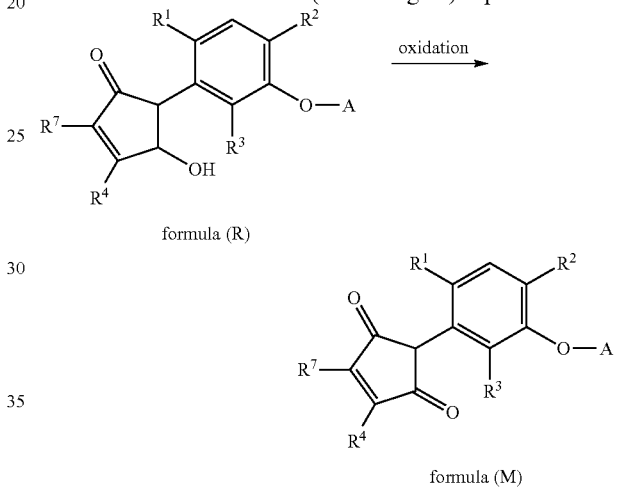

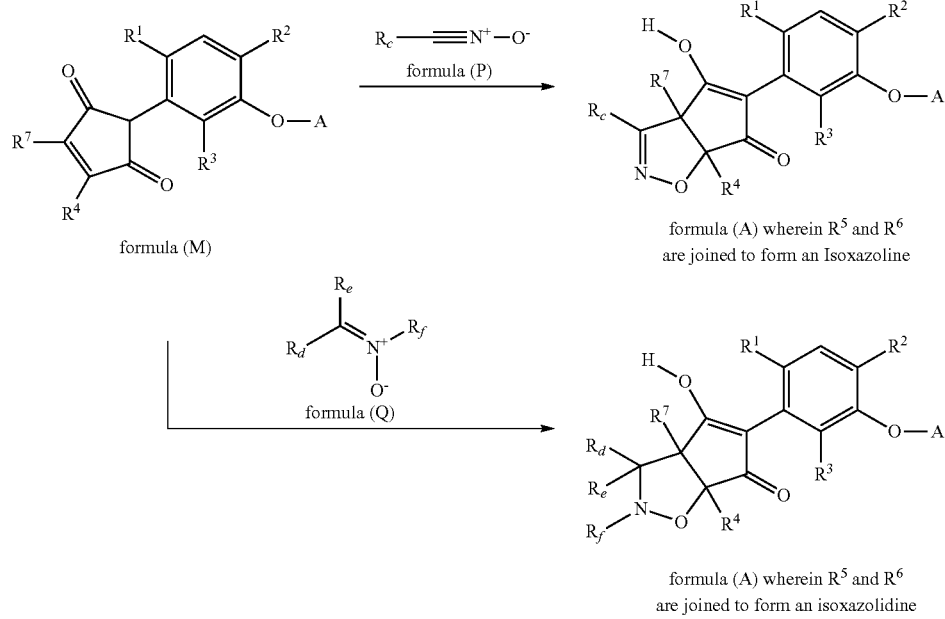

A compound of formula (R) may be prepared from a compound of formula (S) by treatment with a suitable acid catalyst in the presence of water and optionally in the presence of a suitable solvent.

The organometallic reagents of formula (T), formula (U) and formula (V) may be made by known methods from a compound of formula (G).

In a further approach, a compound of formula (A), wherein $R^5$ is Nuc (and Nuc is as previously defined) may be prepared by the hydrolysis of a compound of formula (X), which is a compound of formula I wherein G is $C_1$-$C_4$alkyl, under acidic conditions.

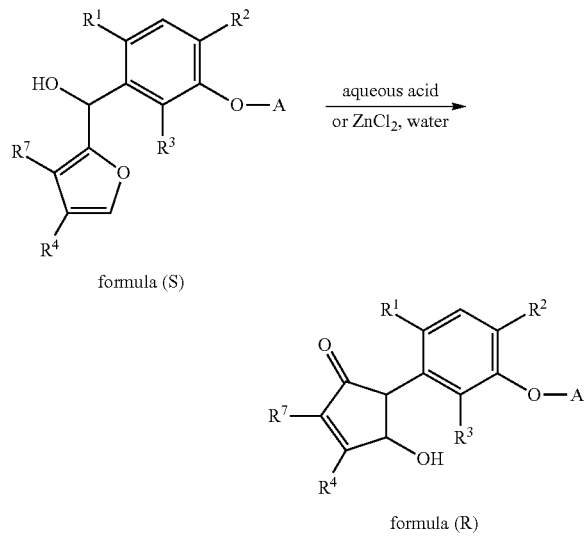

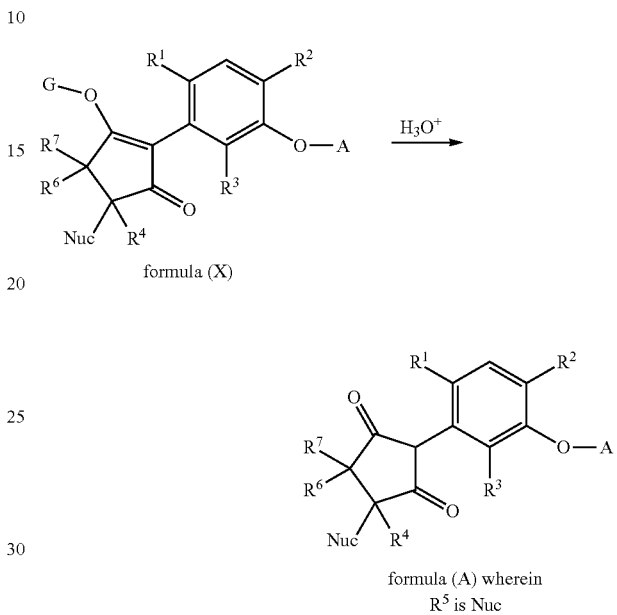

For example, a compound of formula (S) may be converted to a compound of formula (R) in the presence of an aqueous solution of an acid such as phosphoric acid or polyphosphoric acid under conditions described, for example by K. Saito and H. Yamachika, U.S. Pat. No. 4,371,711. Alternatively a compound of formula (R) may be prepared from a compound of formula (S) by rearrangement in the presence of a Lewis acid catalyst such as zinc chloride according to the procedure of G. Piancatelli et al., Tetrahedron, (1978), 34, 2775.

A compound of formula (S) may be prepared by the addition of a suitable organometallic reagent such as an arylmagnesium halide of formula (T) wherein Hal is a halide such as chloride, bromide or iodide, or an aryllithium reagent of formula (U) or a diarylzinc reagent of formula (V) to a furan-2-carboxaldehyde of formula (W) according to known procedures (see, for example G. Panda et al., Tetrahedron Lett., (2005), 46, 3097).

A compound of formula (X) may be prepared from a compound of formula (Y), which is a compound of formula I wherein $R^5$ is Hal and Hal is chlorine, bromine or iodine, by treatment with a nucleophile, Nuc-H, optionally in the presence of a suitable base and in a suitable solvent. Suitable conditions for effecting nucleophilic substitution reactions are described, for example, by J. March, Advanced Organic Chemistry Third Edition, ed J. Wiley and Sons, 1985.

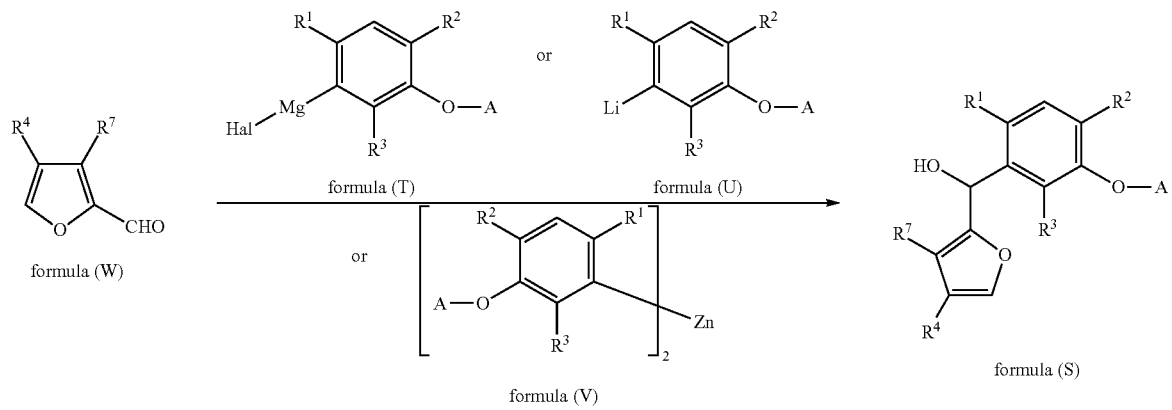

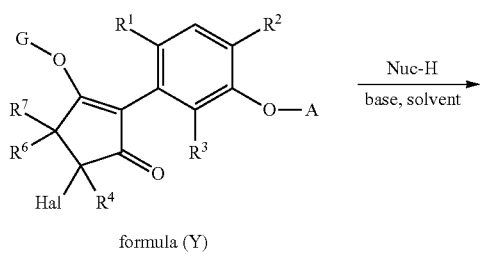

formula (Y)

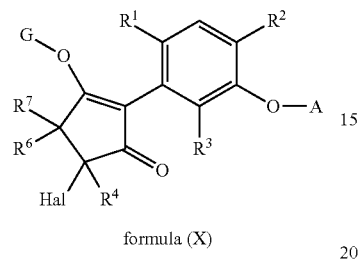

formula (X)

A compound of formula (Y) may be prepared from a compound of formula (Z), which is a compound of formula I wherein $R^5$ is H and G is $C_1$-$C_4$alkyl, by halogenation.

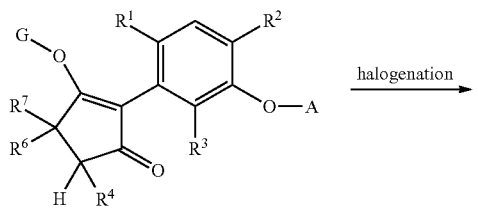

formula (Z)

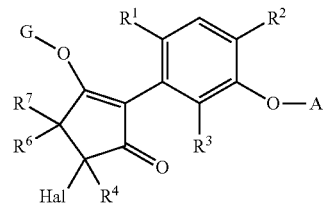

formula (Y)

For example, a compound of formula (Y) wherein Hal is chlorine may be prepared by reacting a compound of formula (Z) with copper(II) chloride and lithium chloride according to the procedure of E. Kosower et al., J. Org. Chem., (1963), 28, 630. Alternatively a compound of formula (Y) wherein Hal is bromine may be prepared treating a compound of formula (Z) with dibutylboryl trifluoromethanesulfonate and N-bromosuccinimide, by methods similar to those described by P. Page et al., Tetrahedron (1995), 51 (4), 1285-1294).

A compound of formula (Z) may be prepared reaction of a compound of formula (AA) with a $C_1$-$C_4$alkyl halide in the presence of a base and a solvent, or by reaction with a tri-$C_1$-$C_4$-alkylorthoformate under conditions similar to those described for the preparation of a compound of formula (K).

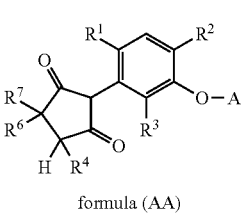

formula (AA)

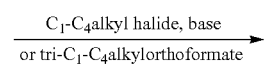

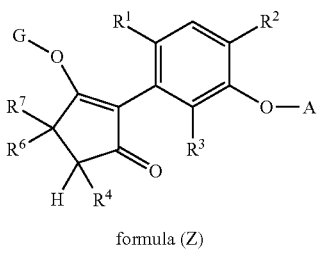

formula (Z)

A compound of formula (AA) is a compound of formula I, wherein $R^5$ is hydrogen, and may be made methods described previously for the preparation of a compound of formula (A).

Alternatively, a compound of formula (AA) wherein $R^6$ is hydrogen may be prepared by reduction of a compound of formula (M), for example by catalytic hydrogenation, or by the use of a suitable metal (such as zinc) in a suitable solvent (such as acetic acid).

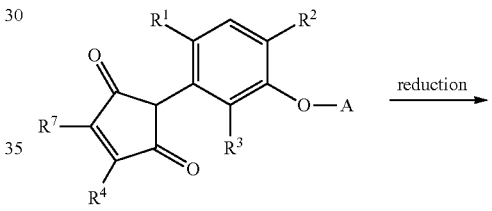

formula (M)

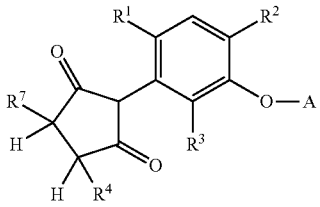

formula (AA) wherein
$R^6$ is hydrogen

In a further approach, a compound of formula I may be prepared by cross-coupling an aryl halide of formula (BB), wherein Hal represents bromine or iodine, with a phenol, A-OH, in the presence of a suitable catalyst, optionally a suitable ligand or additive, a suitable base and a suitable solvent.

formula (BB)

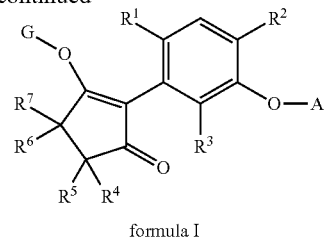

formula I

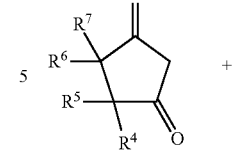

formula (F)

+

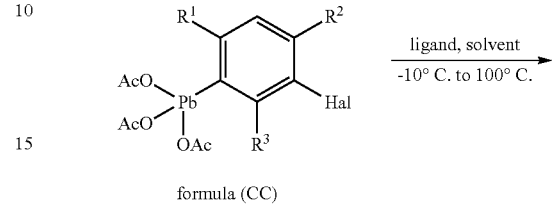

formula (CC)

Suitable conditions for effecting this cross-coupling are described, for example, by S. Hu et al., J. Org. Chem., (2008), 73, 7814-7817; P. Chan et al., Tetrahedron Lett., (2008), 49, 2018-2022); R. Hosseinzadeh et al., Synthetic Commun., (2008) 38, 3023-3031; S. Buchwald et al., J. Am. Chem. Soc., (2006), 128, 10694-10695; H. Rao et al., Chem. Eur. J., (2006), 12, 3636-3646; M. Taillefer et al., Adv. Synth. Catal. (2006), 348, 499-505; M. Beller et al., Tetrahedron Lett., (2005), 46 (18), 3237-3240; M. Taillefer et al., Org. Lett. (2004), 6 (6), 913; D. Ma and Q. Cai, Org. Lett. (2003), 5 (21), 3799-3802; J. Song et al., Org. Lett. (2002), 4 (9), 1623-1626; R. Venkataraman et al., Org. Lett. (2001), 3 (26), 4315-4317; S. Buchwald et al., J. Am. Chem. Soc. (1999), 121, 4369-4378; S. Buchwald et al., J. Am. Chem. Soc., (1997), 119, 10539-10540; G. Mann and J. Hartwig, Tetrahedron Lett., (1997), 38 (46), 8005-8008.

Suitable catalysts include palladium and copper catalysts such as palladium(II) acetate, bis(dibenzylideneacetone)palladium(II), copper powder, copper(II) acetate, copper(I) chloride, copper(I) bromide, copper(II) bromide, copper(I) iodide, copper(I) oxide, copper(II) sulfate, copper(I) trifluoromethanesulfonate and copper(II) trifluoromethanesulfonate. Optionally the catalysts are used in conjunction with appropriate ligands or additives, such as N-methylglycine N,N-dimethylglycine, 1-butylimidazole, ethyl acetate, ethylene glycol diacetate, 8-hydroxyquinoline, L-proline, 1-naphthoic acid, triphenylphosphine, 1,1'-bis(diphenylphosphino)ferrocene, salicylaldoxime, 2-(N,N-dimethylamino)-2'-di-tert-butylphosphinobiphenyl, neocuproine, pyrrolidine-2-phosphionic acid phenyl monoester, 2,2,6,6-tetramethylheptane-3,5-dione, tetrabutylammonium bromide, 2,2-bipyridine or 1,10-phenanthroline. Suitable bases are cesium carbonate, cesium fluoride, potassium fluoride, potassium phosphate and sodium hydroxide. Suitable solvents are acetonitrile, N,N,-dimethylformamide, 1,4-dioxane or toluene, or mixed solvent systems such as toluene/tetrahydrofuran and 1,4-dioxane/water.

The use of copper(I) iodide and copper(II) trifluoromethanesulfonate catalysts is preferred.

A compound of formula (BB) may be prepared by one of the methods described previously for the synthesis of a compound of formula (A), using appropriate starting materials. For example, a compound of formula (BB), wherein G is hydrogen, may be prepared from a compound of formula (F) and an aryllead reagent of formula (CC) under conditions described previously.

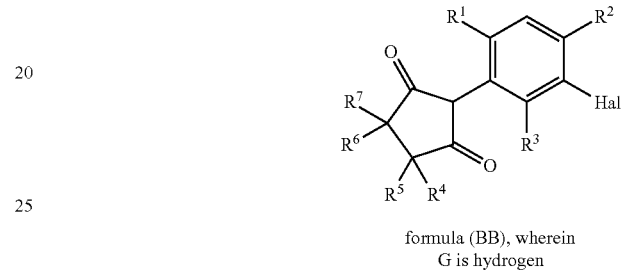

formula (BB), wherein G is hydrogen

In a further approach, a compound of formula I may be prepared by reacting a compound of formula (CC) with an aryl- or heteroaryl halide of formula A-Hal, wherein Hal represents fluorine, chlorine, bromine or iodine under appropriate conditions.

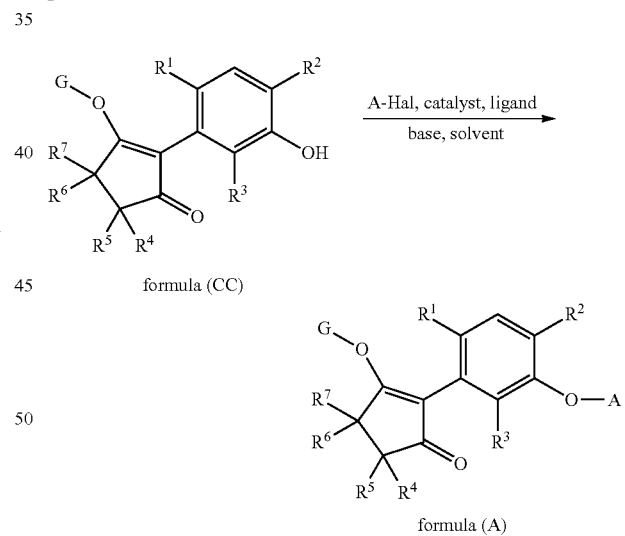

formula (CC)

formula (A)

When A-Hal is an aryl bromide or aryl iodide, the reaction may be effected using suitable copper or palladium catalysts under conditions described previously for the preparation of a compound of formula (A) from a compound of formula (BB). Alternatively, when A-Hal is a suitable, electron-deficient, aryl halide (for example an aryl fluororide or aryl chloride additionally bearing one or more electron-withdrawing substituents such as trifluoromethyl, nitro or cyano), or a suitable heteroaryl halide (for example a halopyridine, or halopyrimidine, haloquinoline, haloquinazoline or haloquinoxaline) the reaction may be effected in the presence of a suitable base such as potassium carbonate or cesium carbonate, without the need for a catalyst and a ligand.

A compound of formula (CC), wherein G is hydrogen, may be prepared from a compound of formula (BB), wherein G is hydrogen.

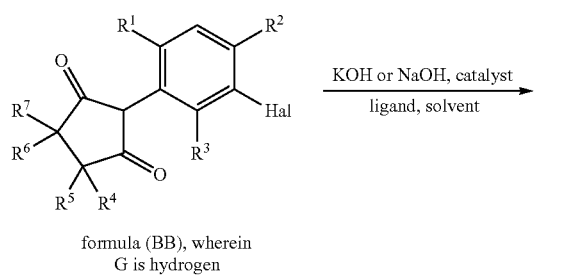

formula (BB), wherein G is hydrogen

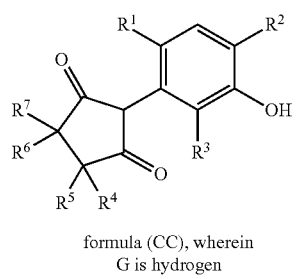

formula (CC), wherein G is hydrogen

In one approach, a compound of formula (BB), wherein G is hydrogen, is deprotonated with a base (such as a Grignard reagent or alkyllithium reagent), and then treated with an alkyllithium reagent to effect metal-halogen exchange. The resulting organometallic species may then be converted into a compound of formula (CC) either by treatment with a trialkylborate such as trimethyl borate followed by oxidation (for example by hydrogen peroxide, N-methyl morpholine N-oxide or oxone) as described, for example by G. Prakash et al., J. Org. Chem., (2001), 66 (2), 633-634; J-P Gotteland and S Halazy, Synlett. (1995), 931-932; K. Webb and D. Levy, Tetrahedron Lett., (1995), 36 (29), 5117-5118. In an alternative approach, a compound of formula (CC), wherein G is hydrogen, may be prepared from a compound of formula (BB), wherein G is hydrogen, by treatment with an aqueous solution of an alkali metal hydroxide in the presence of a suitable catalyst and a suitable ligand, according to known procedures. For example, a compound of formula (CC), wherein G is hydrogen, may be prepared by treating a compound of formula (BB), wherein G is hydrogen, with potassium hydroxide in the presence of a palladium catalyst (for example bis(dibenzylidene-acetone)palladium(II), and in the presence of a suitable phosphine ligand such as 2-(di-tert-butylphosphino)-2',4',6'-triisopropylbiphenyl and 2-(di-tert-butylphosphino)-3,4,5,6-tetramethyl-2',4',6'-triisopropylbiphenyl, under conditions described, for example, by S. Buchwald et al., J. Am. Chem. Soc., (2006), 128, 10694-10695. Alternatively, a compound of formula (CC), wherein G is hydrogen, may be prepared by treating a compound of formula (BB), wherein G is hydrogen, by treatment with an aqueous solution of sodium hydroxide in the presence of a suitable copper catalyst (for example copper(I) iodide) and a suitable ligand (such as L-proline), under conditions described, for example, by C. Kormos and N. Leadbeater, Tetrahedron (2006), 62 (19), 4728-4732.

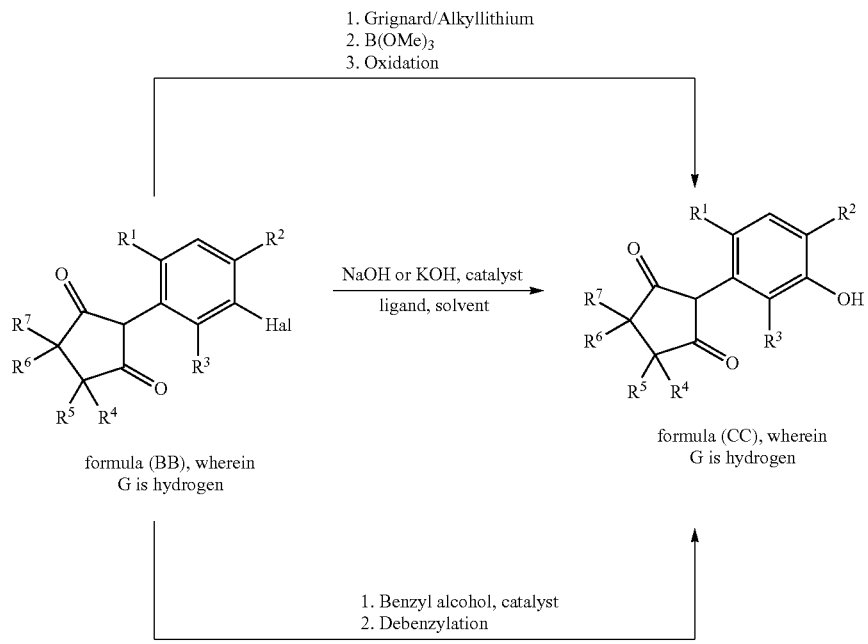

In a third approach to a compound of formula (CC), wherein G is hydrogen, a compound of formula (BB), wherein G is hydrogen, may be treated with a benzyl alcohol in the presence of a suitable copper catalyst, followed by debenzylation under known conditions (for example by catalytic hydrogenolysis).

In a further approach, a compound of formula (CC) may be prepared by the deprotection of a compound of formula (DD), werein P is a suitable protecting group. Suitable protecting groups for phenols, and conditions for the removal of the protecting group are described, for example, by T. Green and P. Wuts, Protective Groups in Organic Synthesis, 3$^{rd}$ Edition, J. Wiley and Sons, (1999). Preferably the protecting group P is a benzyl group.

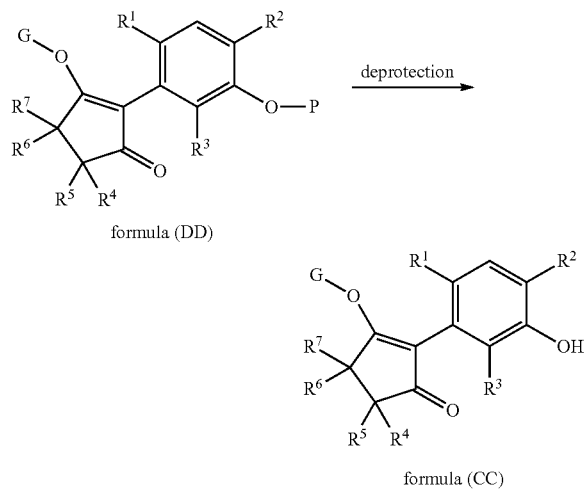

formula (DD)

formula (CC)

Compounds of formula (DD) may be prepared by one or more of the methods similar to those described above for the preparation of compounds of formula I, using appropriate starting materials and appropriate reagents.

The compounds of the formula (M) and (CC), have been particularly designed as intermediates in the synthesis of the compounds of formula I.

The compounds of formula I according to the invention can be used as crop protection agents in unmodified form, as obtained in the synthesis, but they are generally formulated into crop protection compositions in a variety of ways using formulation adjuvants, such as carriers, solvents and surface-active substances. The formulations can be in various physical forms, for example in the form of dusting powders, gels, wettable powders, coated or impregnated granules for manual or mechanical distribution on target sites, water-dispersible granules, water-soluble granules, emulsifiable granules, water-dispersible tablets, effervescent compressed tablets, water-soluble tapes, emulsifiable concentrates, microemulsifiable concentrates, oil-in-water (EW) or water-in-oil (WO) emulsions, other multiphase systems such as oil/water/oil and water/oil/water products, oil flowables, aqueous dispersions, oily dispersions, suspoemulsions, capsule suspensions, soluble liquids, water-soluble concentrates (with water or a water-miscible organic solvent as carrier), impregnated polymer films or in other forms known, for example, from the Manual on Development and Use of FAO Specifications for Plant Protection Products, 5th Edition, 1999. The active ingredient may be incorporated into microfibers or microrods formed of polymers or polymerizable monomers and having diameter of about 0.1 to about 50 microns and aspect ratio of between about 10 and about 1000.

Such formulations can either be used directly or are diluted prior to use. They can then be applied through suitable ground or aerial application spray equipment or other ground application equipment such as central pivot irrigation systems or drip/trickle irrigation means. Diluted formulations can be prepared, for example, with water, liquid fertilisers, micronutrients, biological organisms, oil or solvents.

The formulations can be prepared, for example, by mixing the active ingredient with formulation adjuvants in order to obtain compositions in the form of finely divided solids, granules, solutions, dispersions or emulsions. The active ingredients can also be contained in fine microcapsules consisting of a core and a polymeric shell. Microcapsules usually have a diameter of from 0.1 to 500 microns. They contain active ingredients in an amount of about from 25 to 95% by weight of the capsule weight. The active ingredients can be present in the form of liquid technical material, in the form of a suitable solution, in the form of fine particles in solid or liquid dispersion or as a monolithic solid. The encapsulating membranes comprise, for example, natural and synthetic gums, cellulose, styrene-butadiene copolymers or other similar suitable membrane forming material, polyacrylonitrile, polyacrylate, polyester, polyamides, polyureas, polyurethane, aminoplast resins or chemically modified starch or other polymers that are known to the person skilled in the art in this connection.

Alternatively it is possible for fine so called "microcapsules" to be formed wherein the active ingredient is present in the form of finely divided particles in a solid matrix of a base substance, but in that case the microcapsule is not encapsulated with a diffusion limiting membrane as outlined in the preceding paragraph.

The active ingredients may be adsorbed on a porous carrier. This may enable the active ingredients to be released into their surroundings in controlled amounts (e.g. slow release). Other forms of controlled release formulations are granules or powders in which the active ingredient is dispersed or dissolved in a solid matrix consisting of a polymer, a wax or a suitable solid substance of lower molecular weight. Suitable polymers are polyvinyl acetates, polystyrenes, polyolefins, polyvinyl alcohols, polyvinyl pyrrolidones, alkylated polyvinyl pyrrolidones, copolymers of polyvinyl pyrrolidones and maleic anhydride and esters and half-esters thereof, chemically modified cellulose esters like carboxymethyl cellulose, methyl cellulose, hydroxyethyl cellulose, examples of suitable waxes are polyethylene wax, oxidized polyethylene wax, ester waxes like montan waxes, waxes of natural origin like carnauba wax, candelilla wax, bees wax etc.

Other suitable matrix materials for slow release formulations are starch, stearin, lignin.

The formulation adjuvants suitable for the preparation of the compositions according to the invention are known per se.

As liquid carriers there may be used: water, aromatic solvents such as toluene, m-xylene, o-xylene, p-xylene and mixtures thereof, cumene, aromatic hydrocarbon blends with boiling ranges between 140 and 320° C. known under various trademarks like Solvesso®, Shellsol A®, Caromax®, Hydrosol®, paraffinic and isoparaffinic carriers such as paraffin oils, mineral oils, dearomatized hydrocarbon solvents with boiling ranges between 50 and 320° C. known for instance under the trademark Exxsol®, non-dearomatized hydrocarbon solvents with boiling ranges between 100 and 320° C. known under the tradename Varsol®, isoparaffinic solvents with boiling ranges between 100 and 320° C. known under tradenames like Isopar® or Shellsol T®, hydrocarbons such as cyclohexane, tetrahydronaphthalene (tetralin), decahydronaphthalene, alpha-pinene, d-limonene, hexadecane, isooctane, ester solvents such as ethyl acetate, n/i-butyl acetate, amyl acetate, i-bornyl acetate, 2-ethylhexyl acetate, $C_6$-$C_{18}$ alkyl esters of acetic acid known under the tradename Exxate®, lactic acid ethylester, lactic acid propylester, lactic acid butylester, benzyl benzoate, benzyl lactate, dipropyleneglycol dibenzoate, dialkyl esters of succinic, maleic and fumaric acid and polar solvents like N-methylpyrrolidone, N-ethyl pyrrolidone, $C_3$-$C_{18}$-alkyl pyrrolidones, gamma-butyrolactone, dimethylsulfoxide, N,N-dimethylformamide, N,N-dimethylacetamide, N,N-dimethyllactamide, $C_4$-$C_{18}$ fatty acid dimethylamides, benzoic acid dimethylamide, acetonitrile, acetone, methyl ethyl ketone, methyl-isobutyl ketone, isoamyl ketone, 2-heptanone, cyclohexanone, isophorone, methyl isobutenyl ketone (mesityl oxide), acetophenone, ethylene carbonate, propylene carbonate, butylene carbonate, alcoholic solvents and diluents such as methanol, ethanol, propanol, n/iso-butanol, n/iso-pentanol, 2-ethyl hexanol, n-octanol, tetrahydrofurfuryl alkohol, 2-methyl-2,4-pentanediol, 4-hydroxy-4-methyl-2-pentanon, cyclohexanol, benzyl alcohol, ethylene glycol, ethylene glycol butyl ether, ethylene glycol methyl ether, diethylene glycol, diethylene glycol butyl ether, diethylene glycol ethyl ether, diethylene glycol methyl ether, propylene glycol, dipropylene glycol, dipropylene glycol methyl ether and other similar glycol ether solvents based on ethylene glycol, propylene glycol and butylene glycol feedstocks, triethylene glycol, polyethylene glycol (PEG 400), polypropylenglycols with molecular masses of 400-4000, glycerol, glycerol acetate, glycerol diacetate, glycerol triacetate, 1,4-dioxane, diethylene glycol abietate, chlorobenzene, chlorotoluene, fatty acid esters such as methyl octanoate, isopropyl myristate, methyl laurate, methyl oleate, mixture of $C_8$-$C_{10}$ fatty acid methyl esters, rape seed oil methyl and ethyl esters, soy bean oil methyl and ethyl esters, vegetable oils, fatty acids such as oleic acid, linoleic acid, linolenic acid, esters of phosphoric and phosphonic acid such as triethyl phosphate, $C_3$-$C_{18}$-tris-alkyl phosphates, alkylaryl phosphates, bis-octyl-octyl phosphonates.

Water is generally the carrier of choice for the dilution of the concentrates.

Suitable solid carriers are, for example, talc, titanium dioxide, pyrophyllite clay, silica (fumed or precipated silica and optionally functionalised or treated, for instance silanised), attapulgite clay, kieselguhr, limestone, calcium carbonate, bentonite, calcium montomorillonite, cottonseed husks, wheatmeal, soybean flour, pumice, wood flour, ground walnut shells, lignin and similar materials, as described, for example, in the EPA CFR 180.1001. (c) & (d). Powdered or granulated fertilisers can also be used as solid carriers.

A large number of surface-active substances can advantageously be used both in solid and in liquid formulations, especially in those formulations which can be diluted with a carrier prior to use. Surface-active substances may be anionic, cationic, amphoteric, non-ionic or polymeric and they may be used as emulsifying, wetting, dispersing or suspending agents or for other purposes. Typical surface-active substances include, for example, salts of alkyl sulfates, such as diethanolammonium lauryl sulfate; Sodium lauryl sulfate, salts of alkylarylsulfonates, such as calcium or sodium dodecylbenzenesulfonate; alkylphenol-alkylene oxide addition products, such as nonylphenol ethoxylates; alcohol-alkylene oxide addition products, such as tridecyl alcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride, polyethylene glycol esters of fatty acids, such as polyethylene glycol stearate; block copolymers of ethylene oxide and propylene oxide; and salts of mono- and di-alkyl phosphate esters; and also further substances described e.g. in "McCutcheon's Detergents and Emulsifiers Annual", MC Publishing Corp., Ridgewood, N.J., 1981.

Further adjuvants which can usually be used in pesticidal formulations include crystallisation inhibitors, viscosity-modifying substances, suspending agents, dyes, anti-oxidants, foaming agents, light absorbers, mixing aids, anti-foams, complexing agents, neutralising or pH-modifying substances and buffers, corrosion-inhibitors, fragrances, wetting agents, absorption improvers, micronutrients, plasticisers, glidants, lubricants, dispersants, thickeners, anti-freezes, microbiocides, compatibility agents and solubilisers and also liquid and solid fertilisers.

The formulations may also comprise additional active substances, for example further herbicides, herbicide safeners, plant growth regulators, fungicides or insecticides.

The compositions according to the invention can additionally include an additive (commonly referred to as an adjuvant), comprising a mineral oil, an oil of vegetable or animal origin, alkyl esters of such oils or mixtures of such oils and oil derivatives. The amount of oil additive used in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsifiable vegetable oil, such as AMIGO® (Loveland Products Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being important. Those esters are known as methyl laurate (CAS-111-82-0), methyl palmitate (CAS-112-39-0) and methyl oleate (CAS-112-62-9). A preferred fatty acid methyl ester derivative is AGNIQUE ME 18 RD-F® (Cognis). Those and other oil derivatives are also known from the Compendium of Herbicide Adjuvants, 5th Edition, Southern Illinois University, 2000.

The application and action of the oil additives can be further improved by combining them with surface-active substances, such as non-ionic, anionic, cationic or amphoteric surfactants. Examples of suitable anionic, non-ionic, cationic or amphoteric surfactants are listed on pages 7 and 8 of WO97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant). Also preferred are silicone surfactants, especially polyalkyl-oxide-modified heptamethyltrisiloxanes, which are commercially available e.g. as SILWET L-77®, and also perfluorinated surfactants. The concentration of surface-active substances in relation to the total additive is generally from 1 to 50% by weight. Examples of oil additives that consist of mixtures of oils or mineral oils or derivatives thereof with surfactants are TURBOCHARGED, ADIGOR® (both (Syngenta Crop Protection AG), ACTIPRON® (BP Oil UK Limited), AGRI-DEX® (Helena Chemical Company).

The said surface-active substances may also be used in the formulations alone, that is to say without oil additives.

Furthermore, the addition of an organic solvent to the oil additive/surfactant mixture can contribute to a further enhancement of action. Suitable solvents are, for example, SOLVESSO® and AROMATIC® solvents (Exxon Corporation). The concentration of such solvents can be from 10 to 80% by weight of the total weight. Such oil additives, which may be in admixture with solvents, are described, for example, in U.S. Pat. No. 4,834,908. A commercially available oil additive disclosed therein is known by the name MERGE® (BASF). Further oil additives that are preferred according to the invention are SCORE® and ADIGOR® (both Syngenta Crop Protection AG).

In addition to the oil additives listed above, in order to enhance the activity of the compositions according to the invention it is also possible for formulations of alkylpyrrolidones, (e.g. AGRIMAX® from ISP) to be added to the spray mixture. Formulations of synthetic latices, such as, for example, polyacrylamide, polyvinyl compounds or poly-1-p-menthene (e.g. BOND®, COURIER® or EMERALD®) can also be used.

Such adjuvant oils as described in the preceding paragraphs may be employed as the carrier liquid in which an active compound is dissolved, emulsified or dispersed as appropriate to the physical form of the active compound.

The pesticidal formulations generally contain from 0.1 to 99% by weight, especially from 0.1 to 95% by weight, of a compound of formula I and from 1 to 99.9% by weight of a formulation adjuvant, which preferably includes from 0 to 25% by weight of a surface-active substance. Whereas commercial products will preferably be formulated as concentrates, the end user will normally employ dilute formulations.

The rate of application of the compounds of formula I may vary within wide limits and depends upon the nature of the soil, the method of application (pre- or post-emergence; seed dressing; application to the seed furrow; no tillage application etc.), the crop plant, the weed or grass to be controlled, the prevailing climatic conditions, and other factors governed by the method of application, the time of application and the target crop. The compounds of formula I according to the invention are generally applied at a rate of 1-2000 g/ha, preferably 1-1000 g/ha and most preferably at 1-500 g/ha.

Preferred formulations have especially the following representative compositions:
(%=percent by weight):
Emulsifiable Concentrates:
active ingredient: 1 to 95%, preferably 60 to 90%
surface-active agents: 1 to 30%, preferably 5 to 20%
solvents as liquid carrier: 1 to 80%, preferably 1 to 35%
Dusts:
active ingredient: 0.1 to 10%, preferably 0.1 to 5%
solid carriers: 99.9 to 90%, preferably 99.9 to 99%
Suspension Concentrates:
active ingredient: 5 to 75%, preferably 10 to 50%
water: 94 to 24%, preferably 88 to 30%
surface-active agents: 1 to 40%, preferably 2 to 30%
Wettable Powders:
active ingredient: 0.5 to 90%, preferably 1 to 80%
surface-active agents: 0.5 to 20%, preferably 1 to 15
solid carriers: 5 to 95%, preferably 15 to 90%
Granules:
active ingredient: 0.1 to 30%, preferably 0.1 to 15%
solid carriers: 99.5 to 70%, preferably 97 to 85%
Waterdispersible Granules:
active ingredient: 1 to 90%, preferably 10 to 80%
surface-active agents: 0.5 to 80%, preferably 5 to 30%
solid carriers: 90 to 10%, preferably 70 to 30%

The following Examples further illustrate, but do not limit, the invention.

| F1. Emulsifiable concentrates | a) | b) | c) | d) |
|---|---|---|---|---|
| active ingredient | 5% | 10% | 25% | 50% |
| calcium dodecylbenzene-sulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP | — | 10% | — | 20% |
| arom. hydrocarbon mixture $C_9$-$C_{12}$ | 85% | 68% | 65% | 16% |

Emulsions of any desired concentration can be prepared from such concentrates by dilution with water.

| F2. Solutions | a) | b) | c) | d) |
|---|---|---|---|---|
| active ingredient | 5% | 10% | 50% | 90% |
| 1-methoxy-3-(3-methoxy-propoxy)-propane | 40% | 50% | — | — |
| polyethylene glycol MW 400 | 20% | 10% | — | — |
| NMP | — | — | 50% | 10% |
| arom. hydrocarbon mixture $C_9$-$C_{12}$ | 35% | 30% | — | — |

The solutions are suitable for application undiluted or after dilution with water.

| F3. Wettable powders | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly disperse silicic acid | 1% | 3% | 5% | 10% |
| kaolin | 88% | 62% | 35% | — |

The active ingredient is thoroughly mixed with the adjuvants and the mixture is thoroughly ground in a suitable mill, yielding wettable powders which can be diluted with water to give suspensions of any desired concentration.

| F4. Coated granules | a) | b) | c) |
|---|---|---|---|
| active ingredient | 0.1% | 5% | 15% |
| highly dispersed silica | 0.9% | 2% | 2% |
| inorg. carrier (diameter 0.1-1 mm) e.g. $CaCO_3$ or $SiO_2$ | 99.0% | 93% | 83% |

The active ingredient is dissolved in methylene chloride, the solution is sprayed onto the carrier and the solvent is subsequently evaporated off in vacuo.

| F5. Coated granules | a) | b) | c) |
|---|---|---|---|
| active ingredient | 0.1% | 5% | 15% |
| polyethylene glycol MW 200 | 1.0% | 2% | 3% |
| highly dispersed silica | 0.9% | 1% | 2% |
| inorg. carrier (diameter 0.1-1 mm) e.g. $CaCO_3$ or $SiO_2$ | 98.0% | 92% | 80% |

The finely ground active ingredient is applied uniformly, in a mixer, to the carrier moistened with polyethylene glycol. Non-dusty coated granules are obtained in this manner.

| F6. Extruded granules | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants and the mixture is moistened with water. The resulting mixture is extruded and then dried in a stream of air.

| F7. Water-dispersible granules | a) | b) | c) | d) |
|---|---|---|---|---|
| active ingredient | 5% | 10% | 40% | 90% |
| sodium lignosulfonate | 20% | 20% | 15% | 7% |
| dibutyl naphthalene sulfonate | 5% | 5% | 4% | 2% |
| Gum arabic | 2% | 1% | 1% | 1% |
| Diatomaceous earth | 20% | 30% | 5% | |
| Sodium sulfate | | | 4% | 5% |
| kaolin | 48% | 30% | 30% | |

The active ingredient is mixed and ground with the adjuvants and the mixture is moistened with water. The resulting mixture is extruded and then dried in a stream of air.

| F8. Dusts | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F9. Suspension concentrates | a) | b) | c) | d) |
|---|---|---|---|---|
| active ingredient | 3% | 10% | 25% | 50% |
| propylene glycol | 5% | 5% | 5% | 5% |
| nonylphenol polyglycol ether (15 mol of ethylene oxide) | — | 1% | 2% | — |
| sodium lignosulfonate | 3% | 3% | 7% | 6% |
| heteropolysacharide (Xanthan) | 0.2% | 0.2% | 0.2% | 0.2% |
| 1,2-Benzisothiazolin-3-on | 0.1% | 0.1% | 0.1% | 0.1% |
| silicone oil emulsion | 0.7% | 0.7% | 0.7% | 0.7% |
| water | 87% | 79% | 62% | 38% |

The finely ground active ingredient is intimately mixed with the adjuvants, yielding a suspension concentrate from which suspensions of any desired concentration can be prepared by dilution with water.

Crops of useful plants in which the compositions according to the invention can be used include especially cereals, in particular wheat and barley, rice, corn, rape, sugarbeet, sugarcane, soybean, cotton, sunflower, peanut and plantation crops.

The term "crops" is to be understood as also including crops that have been rendered tolerant to herbicides or classes of herbicides (for example ALS, GS, EPSPS, PPO and HPPD inhibitors) as a result of conventional methods of breeding or genetic engineering. An example of a crop that has been rendered tolerant e.g. to imidazolinones, such as imazamox, by conventional methods of breeding is Clearfield® summer rape (Canola). Examples of crops that have been rendered tolerant to herbicides by genetic engineering methods include e.g. glyphosate- and glufosinate-resistant maize varieties commercially available under the trade names Roundu- pReady® and LibertyLink®. The weeds to be controlled may be both monocotyledonous and dicotyledonous weeds, such as, for example, *Stellaria, Nasturtium, Agrostis, Digitaria, Avena, Setaria, Sinapis, Lolium, Solanum, Echinochloa, Scirpus, Monochoria, Sagittaria, Bromus, Alopecurus, Sorghum, Rottboellia, Cyperus, Abutilon, Sida, Xanthium, Amaranthus, Chenopodium, Ipomoea, Chrysanthemum, Galium, Viola* and *Veronica*. Control of monocotyledonous weeds, in particular *Agrostis, Avena, Setaria, Lolium, Echinochloa, Bromus, Alopecurus* and *Sorghum* is very extensive.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt-176 maize hybrids of NK® (Syngenta Seeds). The Bt toxin is a protein that is formed naturally by *Bacillus thuringiensis* soil bacteria. Examples of toxins and transgenic plants able to synthesise such toxins are described in EP-A-451 878, EP-A-374 753, WO 93/07278, WO 95/34656, WO 03/052073 and EP-A-427 529. Examples of transgenic plants that contain one or more genes which code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops and their seed material can be resistant to herbicides and at the same time also to insect feeding ("stacked" transgenic events). Seed can, for example, have the ability to express an insecticidally active Cry3 protein and at the same time be glyphosate-tolerant. The term "crops" is to be understood as also including crops obtained as a result of conventional methods of breeding or genetic engineering which contain so-called output traits (e.g. improved flavour, storage stability, nutritional content).

Areas under cultivation are to be understood as including land where the crop plants are already growing as well as land intended for the cultivation of those crop plants.

The compounds of formula I according to the invention can also be used in combination with further herbicides. Preferably, in these mixtures, the compound of the formula I is one of those compounds listed in Tables 1 to 39 below. The following mixtures of the compound of formula I are especially important:

compound of formula I+acetochlor, compound of formula I+acifluorfen, compound of formula I+acifluorfen-sodium, compound of formula I+aclonifen, compound of formula I+acrolein, compound of formula I+alachlor, compound of formula I+alloxydim, compound of formula I+allyl alcohol, compound of formula I+ametryn, compound of formula I+amicarbazone, compound of formula I+amidosulfuron, compound of formula I+aminopyralid, compound of formula I+amitrole, compound of formula I+ammonium sulfamate, compound of formula I+anilofos, compound of formula I+asulam, compound of formula I+atraton, compound of formula I+atrazine, compound of formula I+azimsulfuron, compound of formula I+BCPC, compound of formula I+beflubutamid, compound of formula I+benazolin, compound of formula I+benfluralin, compound of formula I+benfuresate, compound of formula I+bensulfuron, compound of formula I+bensulfuron-methyl, compound of formula I+bensulide, compound of formula I+bentazone, compound of formula I+benzfendizone, compound of formula I+benzobicyclon, compound of formula I+benzofenap, compound of formula I+bifenox, compound of formula I+bilanafos, compound of formula I+bispyribac, compound of formula I+bispyribac-sodium, compound of formula I+borax, compound of formula I+bromacil, compound of formula I+bromobutide, compound of formula I+bromoxynil, compound of formula I+butachlor, compound of formula I+butafenacil, compound of formula I+butamifos, compound of formula I+butralin, compound of formula I+butroxydim, compound of formula I+butylate, compound of formula I+cacodylic acid, compound of formula I+calcium chlorate, compound of formula I+cafenstrole, compound of formula I+carbetamide, compound of formula I+carfentrazone, compound of formula I+carfentrazone-ethyl, compound of formula I+CDEA, compound of formula I+CEPC, compound of formula I+chlorflurenol, compound of formula I+chlorflurenol-methyl, compound of formula I+chloridazon, compound of formula I+chlorimuron, compound of formula I+chlorimuron-ethyl, compound of formula I+chloroacetic acid, compound of formula I+chlorotoluron, compound of formula I+chlorpropham, compound of formula I+chlorsulfuron, compound of formula I+chlorthal, compound of formula I+chlorthal-dimethyl, compound of formula I+cinidon-ethyl, compound of formula I+cinmethylin, compound of formula I+cinosulfuron, compound of formula I+cisanilide, compound of formula I+clethodim, compound of formula I+clodinafop, compound of formula I+clodinafop-propargyl, compound of formula I+clomazone, compound of formula I+clomeprop, compound of formula I+clopyralid, compound of formula I+cloransulam, compound of formula I+cloransulam-methyl, compound of formula I+CMA, compound of formula I+4-CPB, compound of formula I+CPMF, compound of formula I+4-CPP, compound of formula I+CPPC, compound of formula I+cresol, compound of formula I+cumyluron, compound of formula I+cyanamide, compound of formula I+cyanazine, compound of formula I+cycloate, compound of formula I+cyclosulfamuron, compound of formula I+cycloxydim, compound of formula I+cyhalofop, compound of formula I+cyhalofop-butyl, compound of formula I+2,4-D, compound of formula I+3,4-DA, compound of formula I+daimuron, compound of formula I+dalapon, compound of formula I+dazomet, compound of formula I+2,4-DB, compound of formula I+3,4-DB, compound of formula I+2,4-DEB, compound of formula I+desmedipham, compound of formula I+dicamba, compound of formula I+dichlobenil, compound of formula I+ortho-dichlorobenzene, compound of formula I+para-dichlorobenzene, compound of formula I+dichlorprop, compound of formula I+dichlorprop-P, compound of formula I+diclofop, compound of formula I+diclofop-methyl, compound of formula I+diclosulam, compound of formula I+difenzoquat, compound of formula I+difenzoquat metilsulfate, compound of formula I+diflufenican, compound of formula I+diflufenzopyr, compound of formula I+dimefuron, compound of formula I+dimepiperate, compound of formula I+dimethachlor, compound of formula I+dimethametryn, compound of formula I+dimethenamid, compound of formula I+dimethenamid-P, compound of formula I+dimethipin, compound of formula I+dimethylarsinic acid, compound of formula I+dinitramine, compound of formula I+dinoterb, compound of formula I+diphenamid, compound of formula I+diquat, compound of formula I+diquat dibromide, compound of formula I+dithiopyr, compound of formula I+diuron, compound of formula I+DNOC, compound of formula I+3,4-DP, compound of formula I+DSMA, compound of formula I+EBEP, compound of formula I+endothal, compound of formula I+EPTC, compound of formula I+esprocarb, compound of formula I+ethalfluralin, compound of formula I+ethametsulfuron, compound of formula I+ethametsulfuron-methyl, compound of formula I+ethofumesate, compound of formula I+ethoxyfen, compound of formula I+ethoxysulfuron, compound of formula I+etobenzanid, compound of formula I+fenoxaprop-P, compound of formula I+fenoxaprop-P-ethyl, compound of formula I+fenoxasulfone (CAS RN 639826-16-7), compound of formula I+fentrazamide, compound of formula I+ferrous sulfate, compound of formula I+flamprop-M, compound of formula I+flazasulfuron, compound of formula I+florasulam, compound of formula I+fluazifop, compound of formula I+fluazifop-butyl, compound of formula I+fluazifop-P, compound of formula I+fluazifop-P-butyl, compound of formula I+flucarbazone, compound of formula I+flucarbazone-sodium, compound of formula I+flucetosulfuron, compound of formula I+fluchloralin, compound of formula I+flufenacet, compound of formula I+flufenpyr, compound of formula I+flufenpyr-ethyl, compound of formula I+flumetsulam, compound of formula I+flumiclorac, compound of formula I+flumiclorac-pentyl, compound of formula I+flumioxazin, compound of formula I+fluometuron, compound of formula I+fluoroglycofen, compound of formula I+fluoroglycofen-ethyl, compound of formula I+flupropanate, compound of formula I+flupyrsulfuron, compound of formula I+flupyrsulfuron-methyl-sodium, compound of formula I+flurenol, compound of formula I+fluridone, compound of formula I+fluorochloridone, compound of formula I+fluoroxypyr, compound of formula I+flurtamone, compound of formula I+fluthiacet, compound of formula I+fluthiacet-methyl, compound of formula I+fomesafen, compound of formula I+foramsulfuron, compound of formula I+fosamine, compound of formula I+glufosinate, compound of formula I+glufosinate-ammonium, compound of formula I+glyphosate, compound of formula I+halosulfuron, compound of formula I+halosulfuron-methyl, compound of formula I+haloxyfop, compound of formula I+haloxyfop-P, compound of formula I+HC-252, compound of formula I+hexazinone, compound of formula I+imazamethabenz, compound of formula I+imazamethabenz-methyl, compound of formula I+imazamox, compound of formula I+imazapic, compound of formula I+imazapyr, compound of formula I+imazaquin, compound of formula I+imazethapyr, compound of formula I+imazosulfuron, compound of formula I+indanofan, compound of formula I+iodomethane, compound of formula I+iodosulfuron, compound of formula I+iodosulfuron-methyl-sodium, compound of formula I+ioxynil, compound of formula I+ipfencarbazone (CAS RN 212201-70-2), compound of formula I+isoproturon, compound of formula I+isouron, compound of formula I+isoxaben, compound of formula I+isoxachlortole, compound of formula I+isoxaflutole, compound of formula I+karbutilate, compound of formula I+lactofen, compound of formula I+lenacil, compound of formula I+linuron, compound of formula I+MAA, compound of formula I+MAMA, compound of formula I+MCPA, compound of formula I+MCPA-thioethyl, compound of formula I+MCPB, compound of formula I+mecoprop, compound of formula I+mecoprop-P, compound of formula I+mefenacet, compound of formula I+mefluidide, compound of formula I+mesosulfuron, compound of formula I+mesosulfuron-methyl, compound of formula I+mesotrione, compound of formula I+metam, compound of formula I+metamifop, compound of formula I+metamitron, compound of formula I+metazachlor, compound of formula I+metazosulfuron (NC-620, CAS RN 868680-84-6), compound of formula I+methabenzthiazuron, compound of formula I+methylarsonic acid, compound of formula I+methyldymron, compound of formula I+methyl isothiocyanate, compound of formula I+metobenzuron, compound of formula I+metolachlor, compound of formula I+S-metolachlor, compound of formula I+metosulam, compound of formula I+metoxuron, compound of formula I+metribuzin, compound of formula I+metsulfuron, compound of formula I+metsulfuron-methyl, compound of formula I+MK-616, compound of formula I+molinate, compound of formula I+monolinuron, compound of formula I+MSMA, compound of formula I+naproanilide, compound of formula I+napropamide, compound of formula I+naptalam, compound of formula I+neburon, compound of formula I+nicosulfuron, compound of formula I+nonanoic acid, compound of formula I+norflurazon, compound of formula I+oleic acid (fatty acids), compound of formula I+orbencarb, compound of formula I+orthosulfamuron, compound of formula I+oryzalin, compound of formula I+oxadiargyl, compound of formula I+oxadiazon, compound of formula I+oxasulfuron, compound of formula I+oxaziclomefone, compound of formula I+oxyfluorfen, compound of formula I+paraquat, compound of formula I+paraquat dichloride, compound of formula I+pebulate, compound of formula I+pendimethalin, compound of formula I+penoxsulam, compound of formula I+pentachlorophenol, compound of formula I+pentanochlor, compound of formula I+pentoxazone, compound of formula I+pethoxamid, compound of formula I+petrolium oils, compound of formula I+phenmedipham, compound of formula I+phenmedipham-ethyl, compound of formula I+picloram, compound of formula I+picolinafen, compound of formula I+pinoxaden, compound of formula I+piperophos, compound of formula I+potassium arsenite, compound of formula I+potassium azide, compound of formula I+pretilachlor, compound of formula I+primisulfuron, compound of formula I+primisulfuron-methyl, compound of formula I+prodiamine, compound of formula I+profluazol, compound of formula I+profoxydim, compound of formula I+prometon, compound of formula I+prometryn, compound of formula I+propachlor, compound of formula I+propanil, compound of formula I+propaquizafop, compound of formula I+propazine, compound of formula I+propham, compound of formula I+propisochlor, compound of formula I+propoxycarbazone, compound of formula I+propoxycarbazone-sodium, compound of formula I+propyrisulfuron (TH-547, CAS RN 570415-88-2), compound of formula I+propyzamide, compound of formula I+prosulfocarb, compound of formula I+prosulfuron, compound of formula I+pyraclonil, compound of formula I+pyraflufen, compound of formula I+pyraflufen-ethyl, compound of formula I+pyrazolynate, compound of formula I+pyrazosulfuron, compound of formula I+pyrazosulfuron-ethyl, compound of formula I+pyrazoxyfen, compound of formula I+pyribenzoxim, compound of formula I+pyributicarb, compound of formula I+pyridafol, compound of formula I+pyridate, compound of formula I+pyriftalid, compound of formula I+pyriminobac, compound of formula I+pyriminobac-methyl, compound of formula I+pyrimisulfan, compound of formula I+pyrithiobac, compound of formula I+pyrithiobac-sodium, compound of formula I+quinclorac, compound of formula I+quinmerac, compound of formula I+quinoclamine, compound of formula I+quizalofop, compound of formula I+quizalofop-P, compound of formula I+rimsulfuron, compound of formula I+sethoxydim, compound of formula I+siduron, compound of formula I+simazine, compound of formula I+simetryn, compound of formula I+SMA, compound of formula I+sodium arsenite, compound of formula I+sodium azide, compound of formula I+sodium chlorate, compound of formula I+sulcotrione, compound of formula I+sulfentrazone, compound of formula I+sulfometuron, compound of formula I+sulfometuron-methyl, compound of formula I+sulfosate, compound of formula I+sulfosulfuron, compound of formula I+sulfuric acid, compound of formula I+tar oils, compound of formula I+2,3,6-TBA, compound of formula I+TCA, compound of formula I+TCA-sodium, compound of formula I+tebuthiuron, compound of formula I+tepraloxydim, compound of formula I+terbacil, compound of formula I+terbumeton, compound of formula I+terbuthylazine, compound of formula I+terbutryn, compound of formula I+thenylchlor, compound of formula I+thiazopyr, compound of formula I+thifensulfuron, compound of formula I+thifensulfuron-methyl, compound of formula I+thiobencarb, compound of formula I+tiocarbazil, compound of formula I+topramezone, compound of formula I+tralkoxydim, compound of formula I+tri-allate, compound of formula I+triasulfuron, compound of formula I+triaziflam, compound of formula I+tribenuron, compound of formula I+tribenuron-methyl, compound of formula I+tricamba, compound of formula I+triclopyr, compound of formula I+trietazine, compound of formula I+trifloxysulfuron, compound of formula I+trifloxysulfuron-sodium, compound of formula I+trifluralin, compound of formula I+triflusulfuron, compound of formula I+triflusulfuron-methyl, compound of formula I+trihydroxytriazine, compound of formula I+tritosulfuron, compound of formula I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6), compound of formula I+4-[(4,5-dihydro-3-methoxy-4-methyl-5-oxo)-1H-1,2,4-triazol-1-ylcarbonylsulfamoyl]-5-methylthiophene-3-carboxylic acid (BAY636), compound of formula I+BAY747 (CAS RN 335104-84-2), compound of formula I+topramezone (CAS RN 210631-68-8), compound of formula I+4-hydroxy-3-[[2-[(2-methoxyethoxy)methyl]-6-(trifluoromethyl)-3-pyridinyl]carbonyl]-bicyclo[3.2.1]oct-3-en-2-one (CAS RN 352010-68-5), and compound of formula I+4-hydroxy-3-[[2-(3-methoxypropyl)-6-(difluoromethyl)-3-pyridinyl]carbonyl]-bicyclo[3.2.1]oct-3-en-2-one.

The mixing partners for the compound of formula I may also be in the form of esters or salts, as mentioned e.g. in The Pesticide Manual, 12th Edition (BCPC) 2000.

For applications in cereals, the following mixtures are preferred: compound of formula I+aclonifen, compound of formula I+amidosulfuron, compound of formula I+aminopyralid, compound of formula I+beflubutamid, compound of formula I+benfluralin, compound of formula I+bifenox, compound of formula I+bromoxynil, compound of formula I+butafenacil, compound of formula I+carbetamide, compound of formula I+carfentrazone, compound of formula I+carfentrazone-ethyl, compound of formula I+chlorotoluron, compound of formula I+chlorpropham, compound of formula I+chlorsulfuron, compound of formula I+cinidon-ethyl, compound of formula I+clodinafop, compound of formula I+clodinafop-propargyl, compound of formula I+clopyralid, compound of formula I+2,4-D, compound of formula I+dicamba, compound of formula I+dichlobenil, compound of formula I+dichlorprop, compound of formula I+diclofop, compound of formula I+diclofop-methyl, compound of formula I+difenzoquat, compound of formula I+difenzoquat metilsulfate, compound of formula I+diflufenican, compound of formula I+diquat, compound of formula I+diquat dibromide, compound of formula I+fenoxaprop-P, compound of formula I+fenoxaprop-P-ethyl, compound of formula I+flamprop-M, compound of formula I+florasulam, compound of formula I+fluazifop-P-butyl, compound of formula I+flucarbazone, compound of formula I+flucarbazone-sodium, compound of formula I+flufenacet, compound of formula I+flupyrsulfuron, compound of formula I+flupyrsulfuron-methyl-sodium, compound of formula I+fluorochloridone, compound of formula I+fluoroxypyr, compound of formula I+flurtamone, compound of formula I+imazamethabenz-methyl, compound of formula I+imazamox, compound of formula I+iodosulfuron, compound of formula I+iodosulfuron-methyl-sodium, compound of formula I+ioxynil, compound of formula I+isoproturon, compound of formula I+linuron, compound of formula I+MCPA, compound of formula I+mecoprop, compound of formula I+mecoprop-P, compound of formula I+mesosulfuron, compound of formula I+mesosulfuron-methyl, compound of formula I+mesotrione, compound of formula I+metribuzin, compound of formula I+metsulfuron, compound of formula I+metsulfuron-methyl, compound of formula I+pendimethalin, compound of formula I+picolinafen, compound of formula I+pinoxaden, compound of formula I+prodiamine, compound of formula I+propanil, compound of formula I+propoxycarbazone, compound of formula I+propoxycarbazone-sodium, compound of formula I+prosulfocarb, compound of formula I+pyrasulfotole, compound of formula I+pyridate, compound of formula I+pyroxasulfone (KIN-485), compound of formula I+pyroxsulam compound of formula I+sulfosulfuron, compound of formula I+tembotrione, compound of formula I+terbutryn, compound of formula I+thifensulfuron, compound of formula I+thiencarbazone, compound of formula I+thifensulfuron-methyl, compound of formula I+topramezone, compound of formula I+tralkoxydim, compound of formula I+tri-allate, compound of formula I+triasulfuron, compound of formula I+tribenuron, compound of formula I+tribenuron-methyl, compound of formula I+trifluralin, compound of formula I+trinexapac-ethyl and compound of formula I+tritosulfuron, where the mixtures comprising a compound of formula (I)+amidosulfuron, compound of formula (I)+aminopyralid, compound of formula (I)+beflubutamid, compound of formula (I)+bromoxynil, compound of formula (I)+carfentrazone, compound of formula (I)+carfentrazone-ethyl, compound of formula (I)+chlorotoluron, compound of formula (I)+chlorsulfuron, compound of formula (I)+clodinafop, compound of formula (I)+clodinafop-propargyl, compound of formula (I)+clopyralid, 2,4-D, compound of formula (I)+dicamba, compound of formula (I)+difenzoquat, compound of formula (I)+difenzoquat metilsulfate, compound of formula (I)+diflufenican, compound of formula (I)+fenoxaprop-P, compound of formula (I)+fenoxaprop-P-ethyl, compound of formula (I)+florasulam, compound of formula (I)+flucarbazone, compound of formula (I)+flucarbazone-sodium, compound of formula (I)+flufenacet, compound of formula (I)+flupyrsulfuron, compound of formula (I)+flupyrsulfuron-methyl-sodium, compound of formula (I)+fluoroxypyr, compound of formula (I)+flurtamone, compound of formula (I)+iodosulfuron, compound of formula (I)+iodosulfuron-methyl-sodium, compound of formula (I)+MCPA, compound of formula (I)+mesosulfuron, compound of formula (I)+mesosulfuron-methyl, compound of formula (I)+metsulfuron, compound of formula (I)+metsulfuron-methyl, compound of formula (I)+pendimethalin, compound of formula (I)+picolinafen, compound of formula (I)+pinoxaden, compound of formula (I)+prosulfocarb, compound of formula (I)+pyrasulfotole, compound of formula (I)+pyroxasulfone (KIN-485), compound of formula (I)+pyroxsulam, compound of formula (I)+sulfosulfuron, compound of formula (I)+thifensulfuron, compound of formula (I)+thifensulfuron-methyl, compound of formula (I)+tralkoxydim, compound of formula (I)+triasulfuron, compound of formula (I)+tribenuron, compound of formula (I)+tribenuron-methyl, compound of formula (I)+trifluralin, compound of formula (I)+trinexapac-ethyl and compound of formula (I)+tritosulfuron are particularly preferred.

For applications in rice, the following mixtures are preferred: compound of formula (I)+azimsulfuron, compound of formula (I)+bensulfuron, compound of formula (I)+bensulfuron-methyl, compound of formula (I)+benzobicyclon, compound of formula (I)+benzofenap, compound of formula (I)+bispyribac, compound of formula (I)+bispyribac-sodium, compound of formula (I)+butachlor, compound of formula (I)+cafenstrole, compound of formula (I)+cinosulfuron, compound of formula (I)+clomazone, compound of formula (I)+clomeprop, compound of formula (I)+cyclosulfamuron, compound of formula (I)+cyhalofop, compound of formula (I)+cyhalofop-butyl, compound of formula (I)+2,4-D, compound of formula (I)+daimuron, compound of formula (I)+dicamba, compound of formula (I)+diquat, compound of formula (I)+diquat dibromide, compound of formula (I)+esprocarb, compound of formula (I)+ethoxysulfuron, compound of formula (I)+fenoxaprop-P, compound of formula (I)+fenoxaprop-P-ethyl, compound of formula I+fenoxasulfone (CAS RN 639826-16-7), compound of formula (I)+fentrazamide, compound of formula (I)+florasulam, compound of formula (I)+glufosinate-ammonium, compound of formula (I)+glyphosate, compound of formula (I)+halosulfuron, compound of formula (I)+halosulfuron-methyl, compound of formula (I)+imazosulfuron, compound of formula I+ipfencarbazone (CAS RN 212201-70-2), compound of formula (I)+MCPA, compound of formula (I)+mefenacet, compound of formula (I)+mesotrione, compound of formula (I)+metamifop, compound of formula I+metazosulfuron (NC-620, CAS RN 868680-84-6), compound of formula (I)+metsulfuron, compound of formula (I)+metsulfuron-methyl, compound of formula (I)+n-methyl glyphosate, compound of formula (I)+orthosulfamuron, compound of formula (I)+oryzalin, compound of formula (I)+oxadiargyl, compound of formula (I)+oxadiazon, compound of formula (I)+paraquat dichloride, compound of formula (I)+pendimethalin, compound of formula (I)+penoxsulam, compound of formula (I)+pretilachlor, compound of formula (I)+profoxydim, compound of formula (I)+propanil, compound of formula I+propyrisulfuron (TH-547, CAS RN 570415-88-2), compound of formula (I)+pyrazolynate, compound of formula (I)+pyrazosulfuron, compound of formula (I)+pyrazosulfuron-ethyl, compound of formula (I)+pyrazoxyfen, compound of formula (I)+pyribenzoxim, compound of formula (I)+pyriftalid, compound of formula (I)+pyriminobac, compound of formula (I)+pyriminobac-methyl, compound of formula (I)+pyrimisulfan, compound of formula (I)+quinclorac, compound of formula (I)+tefuryltrione, compound of formula (I)+triasulfuron and compound of formula (I)+trinexapac-ethyl, where the mixtures comprising a compound of formula (I)+azimsulfuron, compound of formula (I)+bensulfuron, compound of formula (I)+bensulfuron-methyl, compound of formula (I)+benzobicyclon, compound of formula (I)+benzofenap, compound of formula (I)+bispyribac, compound of formula (I)+bispyribac-sodium, compound of formula (I)+clomazone, compound of formula (I)+clomeprop, compound of formula (I)+cyhalofop, compound of formula (I)+cyhalofop-butyl, compound of formula (I)+2,4-D, compound of formula (I)+daimuron, compound of formula (I)+dicamba, compound of formula (I)+esprocarb, compound of formula (I)+ethoxysulfuron, compound of formula (I)+fenoxaprop-P, compound of formula (I)+fenoxaprop-P-ethyl, compound of formula I+fenoxasulfone (CAS RN 639826-16-7), compound of formula (I)+fentrazamide, compound of formula (I)+florasulam, compound of formula (I)+halosulfuron, compound of formula (I)+halosulfuron-methyl, compound of formula (I)+imazosulfuron, compound of formula I+ipfencarbazone (CAS RN 212201-70-2), compound of formula (I)+MCPA, compound of formula (I)+mefenacet, compound of formula (I)+mesotrione, compound of formula I+metazosulfuron (NC-620, CAS RN 868680-84-6), compound of formula (I)+metsulfuron, compound of formula (I)+metsulfuron-methyl, compound of formula (I)+orthosulfamuron, compound of formula (I)+oxadiargyl, compound of formula (I)+oxadiazon, compound of formula (I)+pendimethalin, compound of formula (I)+penoxsulam, compound of formula (I)+pretilachlor, compound of formula I+propyrisulfuron (TH-547, CAS RN 570415-88-2), compound of formula (I)+pyrazolynate, compound of formula (I)+pyrazosulfuron, compound of formula (I)+pyrazosulfuron-ethyl, compound of formula (I)+pyrazoxyfen, compound of formula (I)+pyribenzoxim, compound of formula (I)+pyriftalid, compound of formula (I)+pyriminobac, compound of formula (I)+pyriminobac-methyl, compound of formula (I)+pyrimisulfan, compound of formula (I)+quinclorac, compound of formula (I)+tefuryltrione, compound of formula (I)+triasulfuron and compound of formula (I)+trinexapac-ethyl are particularly preferred.

The compounds of formula I according to the invention can also be used in combination with safeners. Preferably, in these mixtures, the compound of the formula I is one of those compounds listed in Tables 1 to 39 below. The following mixtures with safeners, especially, come into consideration: compound of formula I+cloquintocet-mexyl, compound of formula I+cloquintocet acid and salts thereof, compound of formula I+fenchlorazole-ethyl, compound of formula I+fenchlorazole acid and salts thereof, compound of formula I+mefenpyr-diethyl, compound of formula I+mefenpyr diacid, compound of formula I+isoxadifen-ethyl, compound of formula I+isoxadifen acid, compound of formula I+furilazole, compound of formula I+furilazole R isomer, compound of formula (I)+N-(2-methoxybenzoyl)-4-[(methylaminocarbonyl)amino]benzenesulfonamide, compound of formula I+benoxacor, compound of formula I+dichlormid, compound of formula I+AD-67, compound of formula I+oxabetrinil, compound of formula I+cyometrinil, compound of formula I+cyometrinil Z-isomer, compound of formula I+fenclorim, compound of formula I+cyprosulfamide, compound of formula I+naphthalic anhydride, compound of formula I+flurazole, compound of formula I+CL 304,415, compound of formula I+dicyclonon, compound of formula I+fluxofenim, compound of formula I+DKA-24, compound of formula I+R-29148 and compound of formula I+PPG-1292. A safening effect can also be observed for the mixtures compound of the formula I+dymron, compound of the formula I+MCPA, compound of the formula I+mecoprop and compound of the formula I+mecoprop-P.

The above-mentioned safeners and herbicides are described, for example, in the Pesticide Manual, Twelfth Edition, British Crop Protection Council, 2000. R-29148 is described, for example by P. B. Goldsbrough et al., Plant Physiology, (2002), Vol. 130 pp. 1497-1505 and references therein, PPG-1292 is known from WO09211761 and N-(2-methoxybenzoyl)-4-[(methylaminocarbonyl)amino]benzenesulfonamide is known from EP365484.

Benoxacor, cloquintocet-mexyl, cyprosulfamide, mefenpyr-diethyl and N-(2-methoxybenzoyl)-4-[(methylaminocarbonyl)amino]benzenesulfonamide are especially preferred, where cloquintocet-mexyl is particularly valuable.

The rate of application of safener relative to the herbicide is largely dependent upon the mode of application. In the case of field treatment, generally from 0.001 to 5.0 kg of safener/ha, preferably from 0.001 to 0.5 kg of safener/ha, and generally from 0.001 to 2 kg of herbicide/ha, but preferably from 0.005 to 1 kg/ha, are applied.

The herbicidal compositions according to the invention are suitable for all methods of application customary in agriculture, such as, for example, pre-emergence application, post-emergence application and seed dressing. Depending upon the intended use, the safeners can be used for pretreating the seed material of the crop plant (dressing the seed or seedlings) or introduced into the soil before or after sowing, followed by the application of the (unsafened) compound of the formula (I), optionally in combination with a co-herbicide. It can, however, also be applied alone or together with the herbicide before or after emergence of the plants. The treatment of the plants or the seed material with the safener can therefore take place in principle independently of the time of application of the herbicide. The treatment of the plant by simultaneous application of herbicide and safener (e.g. in the form of a tank mixture) is generally preferred. The rate of application of safener relative to herbicide is largely dependent upon the mode of application. In the case of field treatment, generally from 0.001 to 5.0 kg of safener/ha, preferably from 0.001 to 0.5 kg of safener/ha, are applied. In the case of seed dressing, generally from 0.001 to 10 g of safener/kg of seed, preferably from 0.05 to 2 g of safener/kg of seed, are applied. When the safener is applied in liquid form, with seed soaking, shortly before sowing, it is advantageous to use safener solutions which contain the active ingredient in a concentration of from 1 to 10 000 ppm, preferably from 100 to 1000 ppm.

It is preferred to apply the other herbicide together with one of the safeners mentioned above.

The following Examples illustrate the invention further but do not limit the invention.

PREPARATION EXAMPLES

Those skilled in the art will appreciate that certain compounds described below are 3-ketoenols, and as such may exist as a single tautomer or as a mixture of keto-enol and diketone tautomers, as described, for example by J. March, Advanced Organic Chemistry, third edition, John Wiley and Sons. The compounds shown below, and in Table T1 are drawn as an arbitrary single enol tautomer, but it should be inferred that this description covers both the diketone form and any possible enols which could arise through tautomerism. Where more than one tautomer is observed in proton NMR, the data shown are for the mixture of tautomers. Furthermore, some of the compounds shown below are drawn as single enantiomers for the purposes of simplicity, but unless specified as single enantiomers, these structures should be construed as representing a mixture of enantiomers in any ratio. Additionally, some of the compounds can exist as diastereoisomers, and it should be inferred that these can be present as a single diastereoisomer or as a mixture of diastereoisomers in any ratio.

Within the detailed experimental section the diketone tautomer is chosen for naming purposes, even if the predominant tautomer is the enol form.

Example 1

Preparation of meso-(1R,2S,6R,7S)-4-[5-(4-chlorophenoxy)-2-ethylphenyl]-10-oxatricyclo[5.2.1.0$^{2,6}$]dec-8-ene-3,5-dione

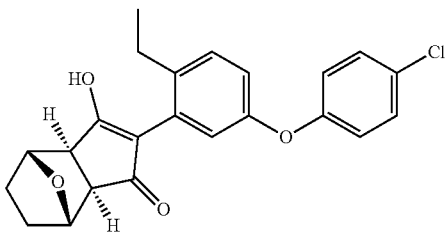 [SMILES: CCc1ccc(Oc2ccc(Cl)cc2)cc1C1=C(O)[C@H]2[C@@H](C1=O)[C@@H]1CC[C@H]2O1]

Step 1: Preparation of meso-(1R,2S,6R,7S)-10-oxatricyclo[5.2.1.0$^{2,6}$]dec-8-ene-3,5-dione

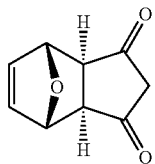

Furan (13.9 ml, 0.19 mol) is added to cyclopentene-1,4-dione (18.4 g, 0.19 mol) and the reaction mixture is stirred at room temperature for 5 days. The mixture is diluted with methanol and meso-(1R,2S,6R,7S)-10-oxatricyclo[5.2.1.0$^{2,6}$]dec-8-ene-3,5-dione is collected by filtration, and used without further purification in the next step.

Step 2: Preparation of meso-(1R,2S,6R,7S)-10-oxatricyclo[5.2.1.0$^{2,6}$]decane-3,5-dione

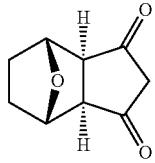

meso-(1R,2S,6R,7S)-10-oxatricyclo[5.2.1.0$^{2,6}$]dec-8-ene-3,5-dione (2.1 g, 12.8 mmol), is dissolved in warm methanol (180 ml) and the mixture is allowed to cool to room temperature. The mixture is then hydrogenated in the presence of 5% palladium on carbon (approx. 50 mg) at 3.5 bar for 4 hours. The catalyst is removed by filtration through diatomaceous earth and the filtrate is concentrated under reduced pressure to afford meso-(1R,2S,6R,7S)-10-oxatricyclo[5.2.1.0$^{2,6}$]decane-3,5-dione.

Step 3: Preparation of meso-(1R,2S,6R,7S)-4-[5-bromo-2-ethylphenyl]-10-oxatricyclo[5.2.1.0$^{2,6}$]-decane-3,5-dione 5-Bromo-2-ethylphenyllead triacetate (13.0 g, 9.0 mmol) is added portionwise, over 20 minutes, to a solution of meso-(1R,2S,6R,7S)-10-oxatricyclo[5.2.1.0$^{2,6}$]decane-3,5-dione (1.0 g, 6.0 mmol) and 4-dimethylaminopyridine (3.67 g, 30 mmol) in toluene (10 ml) and chloroform (40 ml) and the mixture is stirred at 80° C. for 4 hours. The mixture is cooled to room temperature, 2M aqueous hydrochloric acid (40 ml) is added and the mixture is stirred vigorously for 15 minutes. The mixture is filtered through diatomaceous earth, washing the filter cake with dichloromethane (40 ml). The organic phase is collected, and the aqueous phase is extracted with dichloromethane. The organic solutions are combined, dried over anhydrous magnesium sulfate, filtered and the filtrate is evaporated under reduced pressure. The residue is purified by column chromatography on silica gel to give meso-(1R,2S,6R,7S)-4-[5-bromo-2-ethylphenyl]-10-oxatricyclo[5.2.1.0$^{2,6}$]-decane-3,5-dione.

Step 5: Preparation of meso-(1R,2S,6R,7S)-4-[5-(4-chlorophenoxy)-2-ethylphenyl]-10-oxatricyclo[5.2.1.0$^{2,6}$]decane-3,5-dione A mixture of meso-(1R,2S,6R,7S)-4-[5-bromo-2-ethylphenyl]-10-oxatricyclo[5.2.1.0$^{2,6}$]-decane-3,5-dione (100 mg, 0.29 mmol), 4-chlorophenol (44 mg, 0.34 mmol), cesium carbonate (187 mg, 0.57 mmol) and copper(II) trifluoromethanesulfonate (5 mg, 0.01 mmol) in 1,2-dimethoxyethane (3 ml) is heated to 150° C. under microwave irradiation for 30 minutes. The mixture is cooled to room temperature, poured into 2M aqueous hydrochloric acid and extracted with ethyl acetate. The organic extract is washed with brine, dried over anhydrous magnesium sulfate, filtered and the filtrate is evaporated under reduced pressure. The residue is purified by preparative reverse phase HPLC to give meso-(1R,2S,6R,7S)-4-[5-(4-chlorophenoxy)-2-ethylphenyl]-10-oxatricyclo[5.2.1.0$^{2,6}$]decane-3,5-dione.

Example 2

Preparation of meso-(3aS,4S,7R,7aR)-2-[5-(6-chloroquinoxalin-2-yloxy)-2-ethylphenyl]hexahydro-4,7-methanoindene-1,3-dione

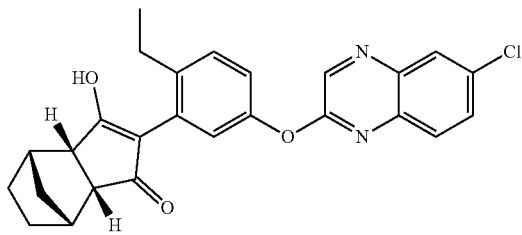 [SMILES: CCc1ccc(Oc2cnc3cc(Cl)ccc3n2)cc1C1=C(O)[C@H]2[C@H]3CC[C@H](C3)[C@H]2C1=O]

Step 1: Preparation of (5-bromo-2-ethylphenyl)furan-2-ylmethanol

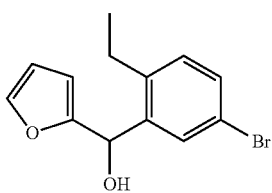 [SMILES: CCc1ccc(Br)cc1C(O)c1ccco1]

4-Bromo-2-iodoethyl benzene (50.0 g, 160.8 mmol) is dissolved in anhydrous tetrahydrofuran (250 ml) and cooled to −70° C. under an atmosphere of nitrogen. Isopropylmagnesium chloride (2M solution in THF, 100 ml, 200 mmol) is added dropwise with vigorous stirring over 40 minutes, maintaining the internal temp below −60° C. by external cooling. When the addition is complete, the reaction is stirred at −70° C. for 20 minutes then allowed to warm to room temperature over 1 h 20 minutes. The reaction mixture is then cooled to −70° C. and a solution of 2-furaldehyde (16 ml, 18.6 g, 190 mmol) in tetrahydrofuran (50 ml) is added dropwise over 40 minutes. On completion of the addition, the reaction is allowed to warm to room temperature and stirred at room temperature for 3 hours. Saturated aqueous ammonium chloride solution (~500 ml) is added and the mixture is extracted into ethyl acetate. The organic solutions are combined, washed with brine, dried over anhydrous magnesium sulfate and concentrated under reduced pressure. The residue is further purified by column chromatography on silica gel to give (5-bromo-2-ethylphenyl)furan-2-ylmethanol (40.7 g).

Step 2: Preparation of 5-(5-bromo-2-ethylphenyl)-4-hydroxycyclopent-2-enone

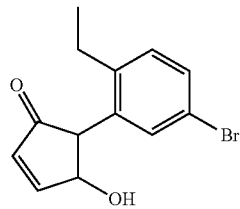 [SMILES: CCc1ccc(Br)cc1C1C(=O)C=CC1O]

A solution of (5-bromo-2-ethylphenyl)furan-2-ylmethanol (40.73 g, 145 mmol) in acetone (1150 ml) and water (170 ml) is heated to 55° C. and 30 drops of polyphosphoric acid are added. The mixture is stirred at 55° C. for 44 hours, then cooled to room temperature. The reaction mixture is concentrated under reduced pressure to remove most of the acetone then ethyl acetate (500 ml) is added, and the reaction mixture is partitioned. The aqueous phase is extracted into ethyl acetate and the organic solutions are combined, washed with saturated aqueous sodium bicarbonate solution and brine, dried over anhydrous magnesium sulfate, filtered and the filtrate is concentrated under reduced pressure. The residue is purified by column chromatography on silica gel to give 5-(5-bromo-2-ethylphenyl)-4-hydroxycyclopent-2-enone (33.67 g).

Step 3: Preparation of 2-(5-bromo-2-ethylphenyl)cyclopent-4-ene-1,3-dione

Jones' reagent (75 ml of 1.67 M solution, 125 mmol) is added dropwise over 30 minutes to a cooled (ice-bath) solution of 5-(5-bromo-4-ethylphenyl)-4-hydroxycyclopent-2-enone (33 g, 117 mmol) in acetone (400 ml). The mixture is stirred for 20 minutes, then the cooling bath is removed and the mixture is stirred for 1 hour at room temperature. Isopropanol (150 ml) is added to the yellow slurry and the mixture is stirred at room temperature for 2 hours. The mixture is diluted with ethyl acetate and washed with brine, dried over anhydrous magnesium sulfate, filtered and the filtrate is evaporated under reduced pressure to give 2-(5-bromo-2-ethylphenyl)cyclopent-4-ene-1,3-dione (32.17 g).

Step 4: Preparation of meso-(3a-5,7aR)-2-(5-bromo-2-ethylphenyl)-3a,4,7,7a-tetrahydro-4,7-methanoindene-1,3-dione

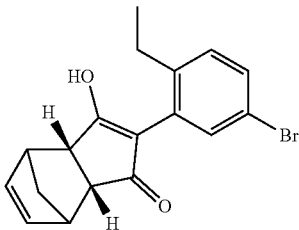 [SMILES: CCc1ccc(Br)cc1C1=C(O)[C@H]2C3C=CC(C3)[C@H]2C1=O]

Dicyclopentadiene (25 ml) is cracked by heating to 180° C., according to known procedures (Elements of Organometallic Chemistry, F R Hartley, page 92-94) and cyclopentadiene (approximately 10 ml), is distilled into a collecting flask containing 2-(5-bromo-2-ethylphenyl)cyclopent-4-ene-1,3-dione (2.6 g, 9.2 mmol), cooled in a salt-ice bath. The resultant reaction mixture is stirred at 0-5° C. for 2 hours, then at room temperature for 18 hours. Iso-hexane (250 mL) is added to the reaction mixture and the resultant white solid is filtered and washed with iso-hexane to give meso-(3a-5,7aR)-2-(5-bromo-2-ethylphenyl)-3a,4,7,7a-tetrahydro-4,7-methanoindene-1,3-dione (2.99 g) used without further purification in the next step.

Step 5: Preparation of meso-(3aS,7aR)-2-(5-bromo-2-ethylphenyl)-hexahydro-4,7-methano-indene-1,3-dione

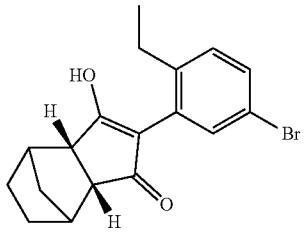 [SMILES: CCc1ccc(Br)cc1C1=C(O)[C@H]2C3CCC(C3)[C@H]2C1=O]

meso-(3aS,7aR)-2-(5-Bromo-2-ethylphenyl)-3a,4,7,7a-tetrahydro-4,7-methanoindene-1,3-dione (2.99 g, 8.67 mmol) is dissolved in methanol (400 ml) and hydrogenated in two portions in the presence of 5% palladium on carbon (approx. 200 mg) at 3.5 bar for 2 hours. The catalyst is removed by filtration through diatomaceous earth and the filtrate is concentrated under reduced pressure to give meso-(3aS,7aR)-2-(5-bromo-2-ethylphenyl)-hexahydro-4,7-methano-indene-1,3-dione (2.98 g).

Step 6: Preparation of meso-(3aS,4S,7R,7aR)-2-(2-ethyl-5-hydroxyphenyl)hexahydro-4,7-methanoindene-1,3-dione

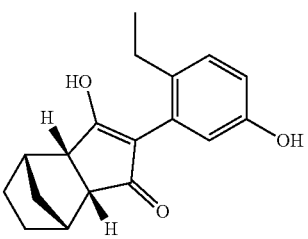 [SMILES: CCc1ccc(O)cc1C1=C(O)[C@H]2[C@H]3CC[C@H](C3)[C@H]2C1=O]

To a solution of meso-(3aS,4S,7R,7aR)-2-(5-bromo-2-ethylphenyl)hexahydro-4,7-methanoindene-1,3-dione (1.0 g, 2.9 mmol), copper (I) iodide (108 mg, 0.57 mmol) and L-proline (33 mg, 0.28 mmol) is added a solution of 1M aqueous sodium hydroxide (8.9 ml, 8.9 mmol), and the mixture is heated at 200° C. for 2 hours under microwave irradiation. After cooling to room temperature the mixture is diluted with ethyl acetate then acidified with 2M hydrochloric acid and filtered through diatomaceous earth (washing with additional ethyl acetate). The aqueous phase is further extracted into ethyl acetate (×3) and the combined organic extracts are washed with brine, dried over magnesium sulfate, filtered and the filtrate concentrated under reduced pressure. The residue was purified by flash column chromatography on silica gel (dichloromethane/methanol eluant) to afford meso-(3aS,4S,7R,7aR)-2-(2-ethyl-5-hydroxyphenyl)hexahydro-4,7-methanoindene-1,3-dione.

Step 7: Preparation of meso-(3aS,4S,7R,7aR)-2-[5-(6-chloroquinoxalin-2-yloxy)-2-ethylphenyl]hexahydro-4,7-methanoindene-1,3-dione

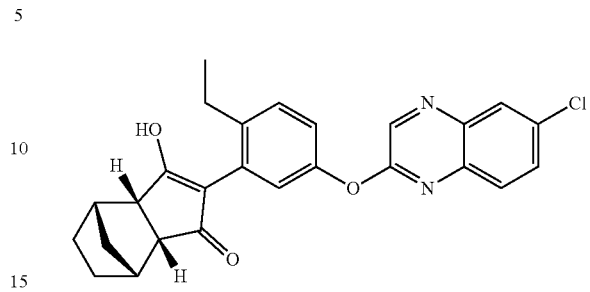

To a mixture of meso-(3aS,4S,7R,7aR)-2-(2-ethyl-5-hydroxyphenyl)hexahydro-4,7-methanoindene-1,3-dione (80 mg, 0.28 mmol) and anhydrous potassium carbonate (90 mg, 0.56 mmol) is added a solution of 2,6-dichloroquinoxaline (67 mg, 0.34 mmol) in anhydrous N,N-dimethylformamide (2.0 ml), and the mixture is heated at 140° C. for 40 minutes under microwave irradiation. After acidification with 2M aqueous hydrochloric acid the mixture is diluted with dichloromethane then filtered (washing with additional dichloromethane). The organic phase is concentrated under reduced pressure and the residue is purified by preparative reverse phase HPLC to afford meso-(3aS,4S,7R,7aR)-2-[5-(6-chloroquinoxalin-2-yloxy)-2-ethylphenyl]hexahydro-4,7-methanoindene-1,3-dione.

Example 3

Preparation of 2-[5-(6-chloroquinoxalin-2-yloxy)-2-ethylphenyl]hexahydro-4,7-ethanoindene-1,3-dione

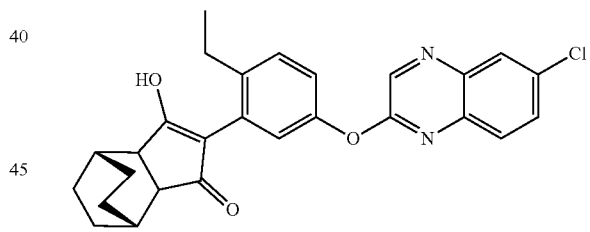

Step 1: Preparation of meso-(3a-5,4R,7S,7aR)-2-(5-bromo-2-ethylphenyl)-3a,4,7,7a-tetrahydro-4,7-ethano-indene-1,3-dione

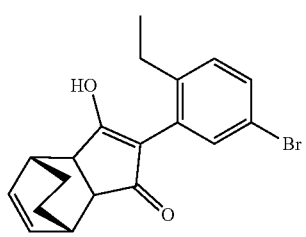 [SMILES: CCc1ccc(Br)cc1C1=C(O)C2C(C1=O)[C@@H]1C=C[C@H]2CC1]

Magnesium iodide (897 mg, 3.22 mmol) is added to a solution of 2-(5-bromo-2-ethylphenyl)cyclopent-4-ene-1,3- dione (3.00 g, 10.7 mmol) in 1,3-cyclohexadiene (10 ml, 108 mmol), and the mixture is heated at 80° C. for 17 hours. The mixture is cooled to room temperature and the solvent evaporated under reduced pressure. Trituration with iso-hexane gave meso-(3aS,4R,7S,7aR)-2-(5-bromo-2-ethylphenyl)-3a, 4,7,7a-tetrahydro-4,7-ethano-indene-1,3-dione (4.638 g) as a white solid.

Step 2: Preparation of 2-(5-Bromo-2-ethylphenyl)-3a,4,5,6,7,7a-hexahydro-4,7-ethanoindene-1,3-dione

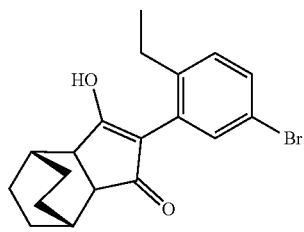 [SMILES: CCc1ccc(Br)cc1C1=C(O)C2C(C1=O)[C@H]1CC[C@@H]2CC1]

meso-(3a-5,4R,7S,7aR)-2-(5-Bromo-2-ethylphenyl)-3a, 4,7,7a-tetrahydro-4,7-ethano-indene-1,3-dione (3.87 g, 10.8 mmol) is dissolved in a mixture of methanol (135 ml) and ethyl acetate (45 ml) and hydrogenated over 10% palladium on charcoal at 25° C. and 30 bar under continuous flow conditions (using an H-Cube® supplied by ThalesNano Nanotechnology Inc. a CatCart® 10% palladium on charcoal cartridge, and a flow-rate of 1.0 ml/minute). The solvent is evaporated and the residue is purified by column chromatography on silica gel, to give 2-(5-bromo-2-ethylphenyl)-3a,4,5,6,7,7a-hexahydro-4,7-ethanoindene-1,3-dione (2.484 g) as an off-white solid.

Step 3: Preparation of 2-(2-ethyl-5-hydroxyphenyl)hexahydro-4,7-ethanoindene-1,3-dione

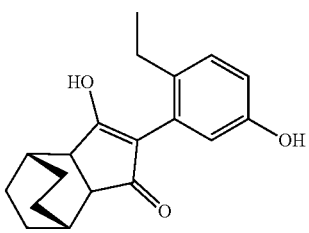 [SMILES: CCc1ccc(O)cc1C1=C(O)C2C(C1=O)[C@H]1CC[C@@H]2CC1]

To a solution of 2-(5-bromo-2-ethylphenyl)-3a,4,5,6,7,7a-hexahydro-4,7-ethanoindene-1,3-dione (1.01 g, 2.8 mmol), copper (I) iodide (108 mg, 0.57 mmol) and L-proline (33 mg, 0.28 mmol) is added a solution of 1M aqueous sodium hydroxide (8.8 mL, 8.8 mmol), and the mixture is then heated at 200° C. for 150 minutes under microwave irradiation. After cooling to room temperature the mixture is diluted with ethyl acetate and then acidified with 2M hydrochloric acid and filtered through diatomaceous earth (washing with additional ethyl acetate). The aqueous phase is extracted into ethyl acetate (×3) and the combined organic extracts are washed with brine, dried over magnesium sulfate, filtered and the filtrate concentrated under reduced pressure. The residue is purified by flash column chromatography on silica gel (ethyl acetate/iso-hexane eluant) to afford 2-(2-ethyl-5-hydroxyphenyl)hexahydro-4,7-ethanoindene-1,3-dione.

Step 4: Preparation of 2-[5-(6-chloroquinoxalin-2-yloxy)-2-ethylphenyl]hexahydro-4,7-ethanoindene-1,3-dione

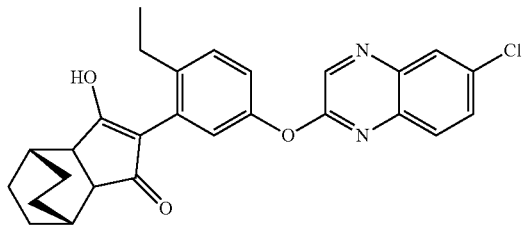 [SMILES: CCc1ccc(Oc2cnc3cc(Cl)ccc3n2)cc1C1=C(O)C2C(C1=O)[C@H]1CC[C@@H]2CC1]

To a mixture of 2-(2-ethyl-5-hydroxyphenyl)hexahydro-4,7-ethanoindene-1,3-dione (83 mg, 0.28 mmol) and anhydrous potassium carbonate (90 mg, 0.56 mmol) is added a solution of 2,6-dichloroquinoxaline (67 mg, 0.34 mmol) in anhydrous dimethylformamide (2.0 ml), and the mixture is heated at 140° C. for 40 minutes under microwave irradiation. The mixture is acidified with 2M aqueous hydrochloric acid and diluted with dichloromethane then filtered. The organic phase is concentrated under reduced pressure and the residue is purified by preparative reverse phase HPLC to afford 2-[5-(6-chloroquinoxalin-2-yloxy)-2-ethylphenyl]hexahydro-4,7-ethanoindene-1,3-dione.

Example 4

Preparation of 2-[5-(3,4-dichlorophenoxy)-2-ethylphenyl]cyclopentane-1,3-dione

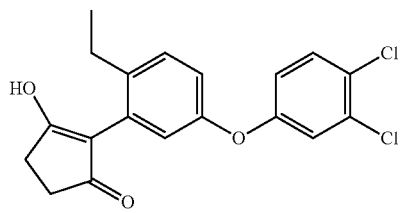 [SMILES: CCc1ccc(Oc2ccc(Cl)c(Cl)c2)cc1C1=C(O)CCC1=O]

Step 1: Preparation of 2-(5-bromo-2-ethylphenyl)cyclopentane-1,3-dione

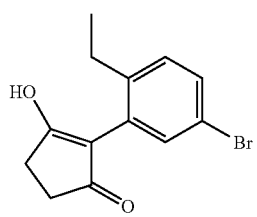 [SMILES: CCc1ccc(Br)cc1C1=C(O)CCC1=O]

To a suspension of zinc dust (13.9 g, 214 mmol) in acetic acid (270 ml) is added a solution of 2-(5-bromo-2-ethylphenyl)cyclopent-4-ene-1,3-dione (8.544 g, 31 mmol) in acetic acid (70 ml). The reaction mixture is stirred at room temperature for 18 hours, then filtered through diatomaceous earth and washed with acetic acid and concentrated under reduced pressure. The crude oil is azeotroped with toluene (×2) then concentrated in vacuo and purified by flash column chromatography on silica gel to afford 2-(5-bromo-2-ethylphenyl)cyclopentane-1,3-dione.

Step 2: Preparation of 2-[5-(3,4-dichlorophenoxy)-2-ethylphenyl]cyclopentane-1,3-dione

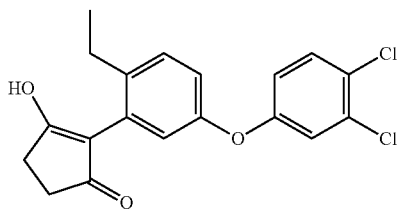 [SMILES: CCc1ccc(Oc2ccc(Cl)c(Cl)c2)cc1C1=C(O)CCC1=O]

To a mixture of 2-(5-bromo-2-ethylphenyl)cyclopentane-1,3-dione (0.200 g, 0.71 mmol), 3,4-dichlorophenol (0.577 g, 3.56 mmol), cesium carbonate (0.502 g, 1.42 mmol), copper triflate (13 mg, 0.04 mmol) and activated (powdered) 5 Å molecular sieves (0.400 g) is added anhydrous toluene (2.5 ml). The reaction mixture is purged with nitrogen and heated at 160° C. for 1 hour under microwave irradiation. After cooling to room temperature dichloromethane is added and mixture is quenched with 2M aqueous hydrochloric acid then filtered. The organic phase is concentrated under reduced pressure to give a crude oil which is purified by preparative reverse-phase HPLC to afford 2-[5-(3,4-dichlorophenoxy)-2-ethylphenyl]cyclopentane-1,3-dione.

Example 5

Preparation of 2-[5-(4-chlorophenoxy)-2-trifluoromethoxyphenyl]cyclopentane-1,3-dione

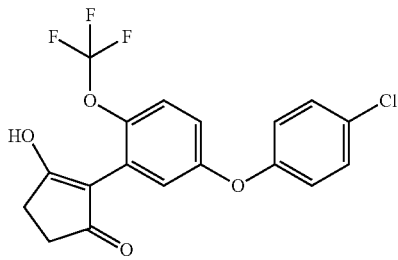 [SMILES: O=C1CCC(O)=C1c1cc(Oc2ccc(Cl)cc2)ccc1OC(F)(F)F]

Step 1: Preparation of 2-(5-bromo-2-trifluoromethoxyphenyl)cyclopentane-1,3-dione

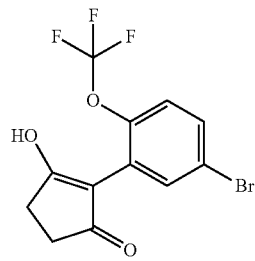 [SMILES: O=C1CCC(O)=C1c1cc(Br)ccc1OC(F)(F)F]

To a solution of 5-bromo-2-trifluoromethoxybenzaldehyde (2.0 g, 7.43 mmol) in anhydrous dichloromethane (40 ml) at room temperature is added boron trifluoride etherate (1.13 ml, 8.92 mmol) then 1,2-bis(trimethylsilyloxy)cyclobutene (2.86 ml, 11.2 mmol). The mixture is stirred at room temperature for 23 hours, followed by addition of distilled water (1.2 ml) and additional boron trifluoride etherate (14.1 ml, 112 mmol). After stirring for 24 hours at room temperature the reaction mixture is then quenched with saturated aqueous ammonium chloride solution (50 ml) and extracted with dichloromethane (2×50 ml). The crude product is extracted into 0.5 M aqueous potassium carbonate solution (×3), then the aqueous phase is acidified to pH 1 with concentrated hydrochloric acid. Final extraction with dichloromethane (×3) is followed by washing with brine then drying over magnesium sulfate. Filtration then concentration in vacuo gives a crude product which is purified by preparative reverse phase HPLC to afford 2-(5-bromo-2-trifluoromethoxyphenyl)cyclopentane-1,3-dione.

Step 2: Preparation of 2-[5-(4-chlorophenoxy)-2-trifluoromethoxyphenyl]cyclopentane-1,3-dione

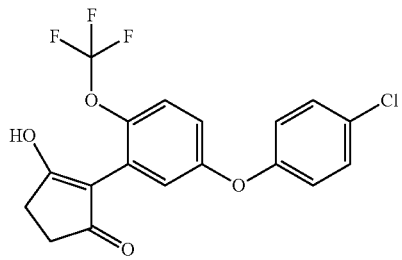 [SMILES: O=C1CCC(O)=C1c1cc(Oc2ccc(Cl)cc2)ccc1OC(F)(F)F]

To a mixture of 4-chlorophenol (0.473 g, 3.69 mmol), cesium carbonate (0.521 g, 1.48 mmol), copper triflate (0.013 g, 0.04 mmol) and powdered 5 Å molecular sieves (0.400 g) is added a solution of 2-(5-bromo-2-trifluoromethoxyphenyl)cyclopentane-1,3-dione (0.249 g, 0.74 mmol) in anhydrous toluene (3.5 ml). The mixture is flushed with nitrogen and heated at 160° C. for 1 hour under microwave radiation, then for a further 1 h at 170° C. After cooling to room temperature the crude product is partitioned between dichloromethane (5 ml) and 2M hydrochloric acid (5 ml), and the organic phase is separated then concentrated in vacuo. The residue is then purified by flash column chromatography on silica gel (ethyl acetate/iso-hexane eluant) to afford 2-[5-(4-chlorophenoxy)-2-trifluoromethoxyphenyl]cyclopentane-1,3-dione as a white solid.

Example 6

Preparation of 2-[5-(4-chlorophenoxy)-2-cyclopropylphenyl]cyclopentane-1,3-dione

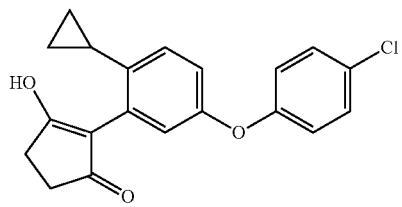 [SMILES: O=C1CCC(O)=C1c1cc(Oc2ccc(Cl)cc2)ccc1C1CC1]

Step 1: Preparation of 5-bromo-2-cyclopropylnitrobenzene

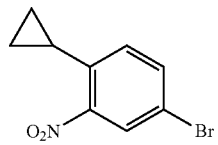

To a mixture of 4-bromo-1-iodo-2-nitrobenzene (21.1 g, 0.064 mol) (described in Synthesis, (2008), (13), 2039-2044), cyclopropyl boronic acid (7.2 g, 0.083 mol), tricyclohexyl phosphine (1.7 g, 0.0064 mol) and potassium phosphate (50.0 g, 0.24 mol) is added toluene (255 ml) and distilled water (23 ml). The stirred mixture is degassed then flushed with nitrogen (cycle repeated ×3), followed by addition of palladium (II) acetate (0.70 g, 0.0032 mol) and heating at 100° C. overnight. After cooling to room temperature the mixture is quenched with distilled water and extracted with ethyl acetate (×3). All organics fractions are combined, washed with distilled water then brine, and dried over magnesium sulfate. Concentration in vacuo affords an approximate 6:4 mixture of 5-bromo-2-cyclopropylnitrobenzene and 4-bromo-1-iodo-2-nitrobenzene (11.9 g) as a brown oil. To this crude mixture is then added additional cyclopropyl boronic acid (1.8 g, 0.021 mol), tricyclohexylphosphine (0.43 g, 0.0016 mol), palladium acetate (0.18 g, 0.0008 mol), potassium phosphate (12.5 g, 0.06 mol), toluene (65 ml) and water (6 ml). After heating at 100° C. overnight the suspension is allowed to cool to room temperature and the mixture is quenched with distilled water and extracted with ethyl acetate (×3). All organics fractions are combined, washed with distilled water then brine, and dried over magnesium sulfate. Concentration in vacuo affords a crude product which is purified by flash column chromatography on silica gel to give a mixture of 5-bromo-2-cyclopropylnitrobenzene, 3-bromo-nitrobenzene and 2,5-dicyclopropyl-nitrobenzene which is used in the next step without further purification.

Step 2: Preparation of 5-bromo-2-cyclopropylaniline

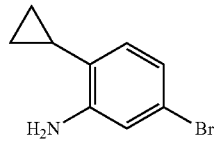 [SMILES: Nc1cc(Br)ccc1C1CC1]

Tin (II) chloride (16.0 g, 0.10 mol) is added in one portion to a solution of crude 5-bromo-2-cyclopropylnitrobenzene (8.68 g) in ethanol (190 ml) and water (1.9 ml). The reaction mixture is stirred at room temperature overnight, followed by addition of further tin (II) chloride (28 g, 0.175 mol) and additional stirring overnight. After concentration in vacuo ice is added, and the solution is basified with 2M aqueous sodium hydroxide. After extraction with ethyl acetate (×2) the organic phase is washed again with 2M aqueous sodium hydroxide, then also distilled water and brine. After drying over magnesium sulfate the solution is concentrated in vcauo to give a brown oil which is purified by flash column chromatography on silica gel (9:1 isohexane/ethyl acetate eluant) to afford 5-bromo-2-cyclopropylaniline as a brown oil.

Step 4: Preparation of 5-bromo-2-cyclopropyliodobenzene

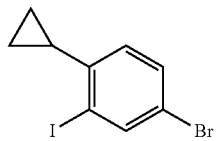 [SMILES: Brc1ccc(C2CC2)c(I)c1]

5-Bromo-2-cyclopropylaniline (4.74 g) is added to a solution of para-toluene sulfonic acid monohydrate (12.2 g, 0.064 mol) in acetonitrile (130 ml), followed by stirring for 10 minutes at room temperature. The suspension is then cooled to 10° C. and a mixed solution of sodium nitrite (8.9 g, 0.054 mol) and potassium iodide (3.1 g, 0.044 mol) in water (16 ml) is added dropwise over 30 minutes. Once the addition is complete the reaction mixture is allowed to stir at 10° C. for 20 minutes and then at room temperature for 4 hours. The reaction mixture is basified to pH 9-10 with aqueous sodium bicarbonate, followed by addition of ethyl acetate and 10% aqueous sodium metabisulphite. The phases are separated and the aqueous layer is extracted again with ethyl acetate (×2). Organics are combined, washed with brine, dried over magnesium sulfate then concentrated in vacuo to give the crude product which is purified by flash column chromatography on silica gel (isohexane eluant) to afford 5-bromo-2-cyclopropyliodobenzene as a colourless oil.

Step 5: Preparation of 5-bromo-2-cyclopropylphenyl boronic acid

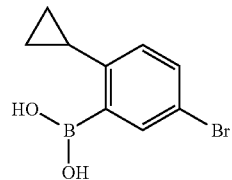

To a solution of 5-bromo-2-cyclopropyliodobenzene (5.67 g, 0.018 mol) in anhydrous tetrahydrofuran (32 ml) at −78° C. is added isopropylmagnesium chloride (9.5 ml, 0.019 mol, 2M solution in THF) at such a rate as to maintain a temperature below −60° C. Once addition is complete the reaction mixture is stirred for 20 minutes at this temperature and then allowed to warm to room temperature and stir for an additional 2 hours. The solution is then cooled again to −78° C. and triisopropylborate (8.3 ml, 0.036 mol) is added dropwise. After stirring at this temperature for 10 minutes the solution is allowed to warm to room temperature and stir for an additional 2 hours. After quenching with 2M aqueous hydrochloric acid (20 ml) the reaction mixture is dilluted with distilled water then extracted with ethyl acetate (×3). Organic fractions are combined, washed with distilled water and brine, then dried over magnesium sulfate and concentrated in vacuo. The crude solid is azeotroped with toluene (×3) then triturated with isohexane to afford 5-bromo-2-cyclopropylphenyl boronic acid as a cream solid.

Step 6: 5-bromo-2-cyclopropylphenyl lead triacetate

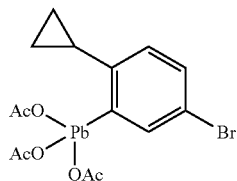

To a solution of lead (IV) acetate (4.0 g, 0.0089 mol) and mercury (II) acetate (139 mg, 0.45 mmol) in chloroform (12 ml) at 50° C. is added 5-bromo-2-cyclopropylphenyl boronic acid (2.0 g, 0.0083 mol), and the solution is heated at this temperature for 5 hours. After cooling to room temperature the suspension is further cooled to 0° C. and anhydrous potassium carbonate (1.8 g) is added with rapid stirring for 2 minutes. The reaction mixture is then filtered (washing with additional chloroform), and the filtrate is concentrated to half its original volume and the crude product is precipitated with hexanes. Further concentration then filtration affords 5-bromo-2-cyclopropylphenyl lead triacetate as a beige solid.

Step 7: Preparation of 2-(5-bromo-2-cyclopropylphenyl)cyclopentane-1,3-dione

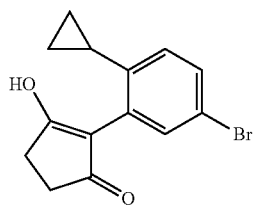 [SMILES: O=C1CCC(O)=C1c1cc(Br)ccc1C1CC1]

To a solution of cyclopentane-1,3-dione (0.57 g, 0.0058 mol) and N,N-dimethylaminopyridine (3.64 g, 0.030 mol) in chloroform (33 ml) is added toluene (9 ml) then 5-bromo-2-cyclopropylphenyl lead triacetate (3.77 g, 0.0065 mol). This solution is heated at 80° C. for 20 hours then cooled to room temperature and dilluted with dichloromethane and 2M aqueous hydrochloric acid. The resulting biphasic suspension is filtered through diatomaceous earth and the two phases are separated. The organic layer is further washed with 2M aqueous hydrochloric acid and the aqueous phase is extracted again with dichloromethane. All organic fractions are combined, washed with brine, dried over magnesium sulfate then concentrated in vacuo. The crude product is finally purified by flash column chromatography on silica gel (isohexane/ethyl acetate eluant) to afford 2-(5-bromo-2-cyclopropylphenyl)cyclopentane-1,3-dione as a pale yellow solid.

Step 8: Preparation of 2-[5-(4-chlorophenoxy)-2-cyclopropylphenyl]cyclopentane-1,3-dione To a mixture of 2-(5-bromo-2-cyclopropylphenyl)cyclopentane-1,3-dione (0.254 g, 0.062 mmol), 4-chlorophenol (0.400 g, 3.11 mmol), cesium fluoride (0.440 g, 1.25 mmol) and copper (II) triflate (11 mg, 0.03 mmol) is added 4 Å powdered molecular sieves (0.40 g) and anhydrous toluene (3.5 ml). This mixture is then heated at 160° C. for 1 hour under microwave irradiation, allowed to cool to room temperature then quenched with 2M hydrochloric acid. The reaction mixture is extracted with dichloromethane (×3), then the combined organics are washed with brine, dried over magnesium sulfate and concentrated in vacuo. The crude product is purified by preparative reverse phase HPLC to afford 2-[5-(4-chlorophenoxy)-2-cyclopropylphenyl]cyclopentane-1,3-dione as a white solid.

Additional compounds in Table T1 below were prepared by similar methods using appropriate starting materials.

TABLE T1

| Compound Number | Structure | $^1$H NMR (CDCl$_3$ unless stated) or other physical data |
|---|---|---|
| A-1 | 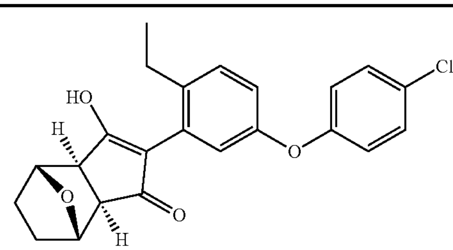 | CDCl$_3$ + 2 drops d$_6$-DMSO δ 7.23 (m, 3H), 6.94 (m, 2H), 6.88 (dd, 1H), 6.73-6.80 (br. m, 1H), 4.68 (m, 2H), 2.73 (br. m, 2H), 2.50 (q, 2H), 1.82 (m, 2H), 1.56 (m, 2H), 1.12 (t, 3H). |
| A-2 | 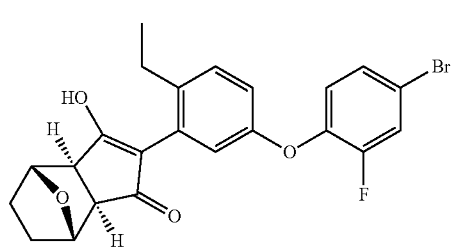 [SMILES: CCc1ccc(Oc2ccc(Br)cc2F)cc1C1=C(O)[C@H]2[C@@H](C1=O)[C@@H]1CC[C@H]2O1] | CDCl$_3$ + 2 drops d$_6$-DMSO δ 7.31 (m, 1H), 7.20 (m, 2H), 6.95 (m, 1H), 6.86 (dd, 1H), 6.79-6.71 (br. m, 1H), 4.68 (m, 2H), 2.92-2.54 (br. m, 2H), 2.49 (q, 2H), 1.88-1.75 (m, 2H), 1.56 (dd, 2H), 1.11 (t, 3H). |

TABLE T1-continued

| Compound Number | Structure | ¹H NMR (CDCl₃ unless stated) or other physical data |
|---|---|---|
| A-3 | 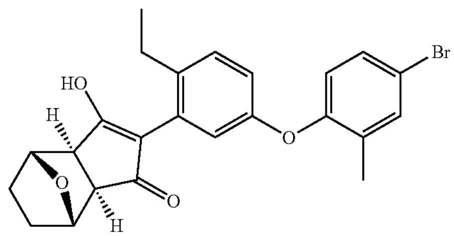 [SMILES: CCc1ccc(Oc2ccc(Br)cc2C)cc1C1=C(O)[C@H]2[C@@H](C1=O)[C@@H]1CC[C@H]2O1] | d₄-MeOH δ 7.39 (m, 1H), 7.25 (dd, 1H), 7.21 (d, 1H), 6.79 (m, 2H), 6.56-6.52 (br m, 1H), 4.58 (t, 2H), 2.81 (s, 2H), 2.43 (q, 2H), 2.22 (s, 3H), 1.83-1.76 (m, 2H), 1.64 (m, 2H), 1.06 (t, 3H). |
| A-4 | 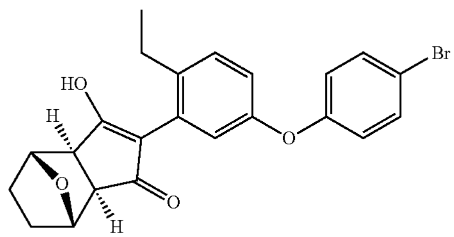 [SMILES: CCc1ccc(Oc2ccc(Br)cc2)cc1C1=C(O)[C@H]2[C@@H](C1=O)[C@@H]1CC[C@H]2O1] | d₄-MeOH δ 7.43 (m, 2H), 7.25 (dd, 1H), 6.93-6.86 (m, 3H), 6.65 (d, 1H), 4.58 (t, 2H), 2.82 (s, 2H), 2.43 (q, 2H), 1.83-1.76 (m, 2H), 1.64 (m, 2H), 1.08 (t, 3H). |
| A-5 | 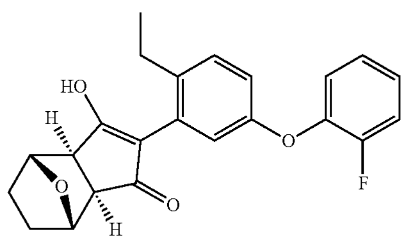 [SMILES: CCc1ccc(Oc2ccccc2F)cc1C1=C(O)[C@H]2[C@@H](C1=O)[C@@H]1CC[C@H]2O1] | d₄-MeOH δ 7.25-7.14 (m, 2H), 7.14-7.03 (m, 3H), 6.84 (dd, 1H), 6.60 (br s, 1H), 4.58 (m, 2H), 2.81 (s, 2H), 2.43 (q, 2H), 1.83-1.75 (m, 2H), 1.64 (m, 2H), 1.06 (t, 3H). |
| A-6 | 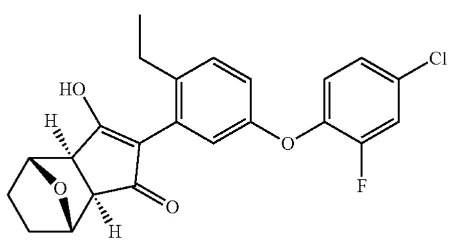 [SMILES: CCc1ccc(Oc2ccc(Cl)cc2F)cc1C1=C(O)[C@H]2[C@@H](C1=O)[C@@H]1CC[C@H]2O1] | d₄-MeOH δ 7.30 (m, 1H), 7.24 (d, 1H), 7.13 (m, 1H), 7.06 (t, 1H), 6.87 (m, 1H), 6.61 (s, 1H), 4.58 (m, 2H), 2.82 (s, 2H), 2.44 (q, 2H), 1.85-1.75 (m, 2H), 1.64 (m, 2H), 1.07 (t, 3H). |
| A-7 | 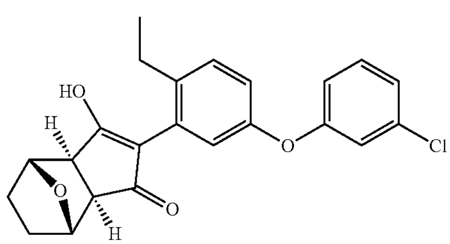 [SMILES: CCc1ccc(Oc2cccc(Cl)c2)cc1C1=C(O)[C@H]2[C@@H](C1=O)[C@@H]1CC[C@H]2O1] | d₄-MeOH δ 7.37-7.27 (m, 2H), 7.08 (m, 1H), 7.01 (m, 1H), 6.94 (m, 2H), 6.71 (m, 1H), 4.62 (t, 2H), 2.86 (s, 2H), 2.49 (q, 2H), 1.87-1.78 (m, 2H), 1.67 (m, 2H), 1.12 (t, 3H). |
| A-8 | 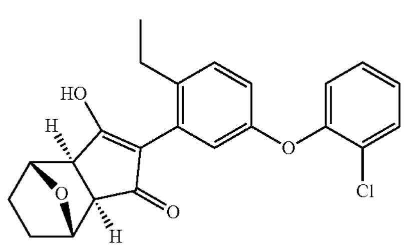 [SMILES: CCc1ccc(Oc2ccccc2Cl)cc1C1=C(O)[C@H]2[C@@H](C1=O)[C@@H]1CC[C@H]2O1] | d₄-MeOH δ 7.48 (m, 1H), 7.31-7.23 (m, 2H), 7.11 (m, 1H), 7.04 (m, 1H), 6.86 (m, 1H), 6.63 (br s, 1H), 4.62 (m, 2H), 2.85 (s, 2H), 2.48 (q, 2H), 1.86-1.78 (m, 2H), 1.67 (m, 2H), 1.10 (t, 3H). |

TABLE T1-continued

| Compound Number | Structure | ¹H NMR (CDCl₃ unless stated) or other physical data |
|---|---|---|
| A-9 | 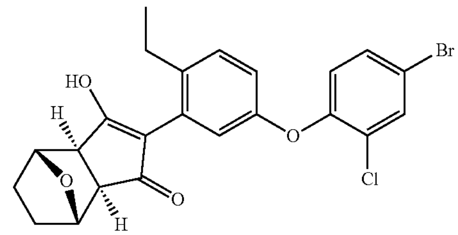 [SMILES: CCc1ccc(Oc2ccc(Br)cc2Cl)cc1C1=C(O)[C@H]2[C@@H](C1=O)[C@@H]1CC[C@H]2O1] | d₆-DMSO δ 7.79 (d, 1H), 7.46 (dd, 1H), 7.17 (d, 1H), 6.90 (d, 1H), 6.81 (dd, 1H), 6.47 (d, 1H), 4.43 (s, 2H), 2.67 (s, 2H), 2.33 (q, 2H), 1.59 (m, 2H), 1.47 (m, 2H), 0.96 (t, 3H). |
| A-10 | 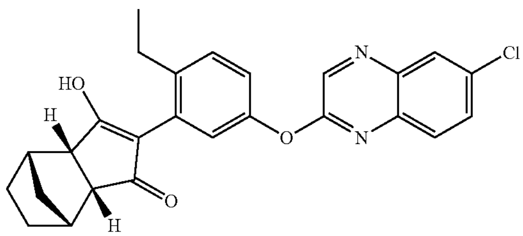 [SMILES: CCc1ccc(Oc2cnc3cc(Cl)ccc3n2)cc1C1=C(O)[C@H]2[C@H]3CC[C@H](C3)[C@H]2C1=O] | d₄-MeOH δ 8.72 (s, 1H), 8.03 (d, 1H), 7.73-7.66 (m, 2H), 7.38 (d, 1H), 7.19 (dd, 1H), 6.93 (d, 1H), 3.05 (s, 2H), 2.63-2.57 (m, 4H), 1.77-1.75 (m, 1H), 1.68-1.66 (m, 1H), 1.53-1.47 (br. m, 2H), 1.42-1.32 (br. m, 2H), 1.18 (t, 3H). |
| A-11 | 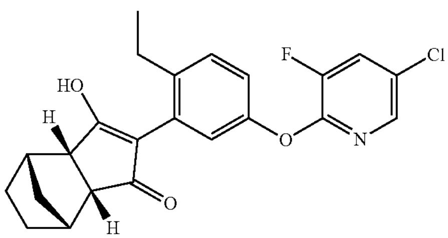 [SMILES: CCc1ccc(Oc2ncc(Cl)cc2F)cc1C1=C(O)[C@H]2[C@H]3CC[C@H](C3)[C@H]2C1=O] | d₄-MeOH δ 7.86 (d, 1H), 7.82 (dd, 1H), 7.31 (d, 1H), 7.04 (dd, 1H), 6.77 (d, 1H), 3.04 (s, 2H), 2.62 (s, 2H), 2.56-2.54 (m, 2H), 1.77-1.74 (m, 1H), 1.68-1.65 (m, 1H) 1.53-1.51 (br. m, 2H), 1.36-1.35 (br. m, 2H), 1.14 (t, 3H). |
| A-12 | 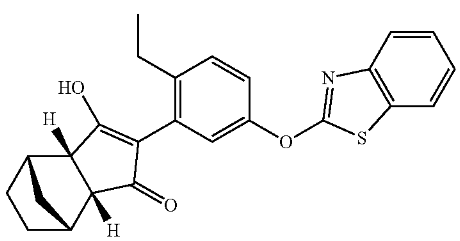 [SMILES: CCc1ccc(Oc2nc3ccccc3s2)cc1C1=C(O)[C@H]2[C@H]3CC[C@H](C3)[C@H]2C1=O] | d₄-MeOH δ 7.74 (d, 1H), 7.62 (d, 1H), 7.41-7.37 (m, 2H), 7.30-7.24 (m, 2H), 7.00 (d, 1H), 3.04 (s, 2H), 2.62-2.57 (m, 4H), 1.76-1.73 (m, 1H), 1.67-1.64 (m, 1H), 1.52 (br. d, 2H), 1.37 (br. d, 2H), 1.67 (t, 3H). |
| A-13 | 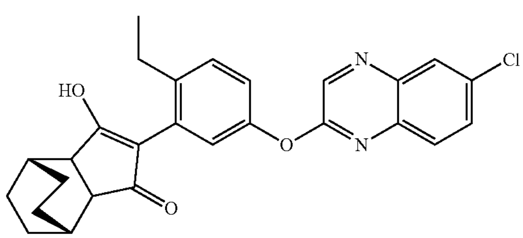 [SMILES: CCc1ccc(Oc2cnc3cc(Cl)ccc3n2)cc1C1=C(O)C2C(C1=O)[C@H]1CC[C@@H]2CC1] | d₄-MeOH δ 8.74 (s, 1H), 8.05 (d, 1H), 7.24-7.68 (m, 2H), 7.41 (d, 1H), 7.22 (dd, 1H), 6.97 (d, 1H), 2.79 (s, 2H), 2.60 (q, 2H), 2.09 (s, 2H), 1.78-1.71 (m, 4H), 1.61-1.59 (br. m, 2H), 1.45-1.43 (br. m, 2H), 1.19 (t, 3H). |
| A-14 | 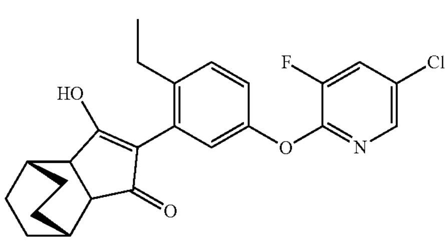 [SMILES: CCc1ccc(Oc2ncc(Cl)cc2F)cc1C1=C(O)C2C(C1=O)[C@H]1CC[C@@H]2CC1] | d₄-MeOH δ 7.89 (d, 1H), 7.83 (dd, 1H), 7.34 (d, 1H), 7.07 (dd, 1H), 6.82 (d, 1H), 2.79 (s, 2H), 2.56 (q, 2H), 2.09 (s, 2H), 1.80-1.69 (m, 4H), 1.59 (br. d, 2H), 1.45 (br. d, 2H), 1.15 (t, 3H). |

TABLE T1-continued

| Compound Number | Structure | ¹H NMR (CDCl₃ unless stated) or other physical data |
|---|---|---|
| A-15 | 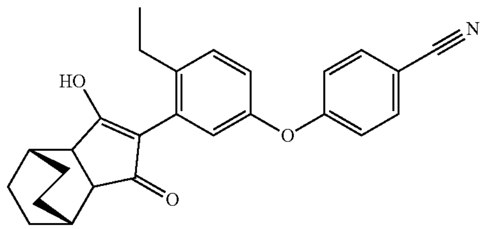 [SMILES: CCc1ccc(Oc2ccc(C#N)cc2)cc1C1=C(O)C2C(C1=O)[C@H]1CC[C@@H]2CC1] | d₄-MeOH δ 7.73-7.67 (m, 2H), 7.36 (d, 1H), 7.14-7.10 (m, 2H), 7.04-6.99 (m, 1H), 6.75 (d, 1H), 6.04 (br. s, 1H), 2.79 (s, 2H), 2.57 (q, 2H), 2.09 (s, 2H), 1.78-1.71 (br. m, 4H), 1.59-1.57 (br. m, 2H), 1.45-1.42 (br. m, 2H), 1.15 (t, 3H). |
| A-16 | 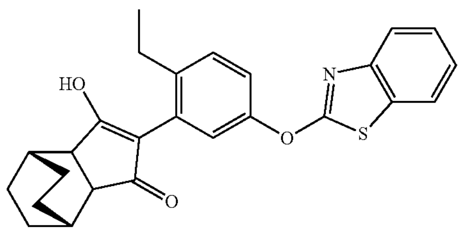 [SMILES: CCc1ccc(Oc2nc3ccccc3s2)cc1C1=C(O)C2C(C1=O)[C@H]1CC[C@@H]2CC1] | d₄-MeOH δ 7.78 (d, 1H), 7.63 (d, 1H), 7.44-7.40 (m, 2H), 7.33-7.28 (m, 2H), 7.03 (s, 1H), 2.80 (s, 2H), 2.57 (q, 2H), 2.10 (s, 2H), 1.78-1.71 (br. m, 4H), 1.60 (br. d, 2H), 1.45 (br. d, 2H), 1.18 (t, 3H). |
| A-17 | 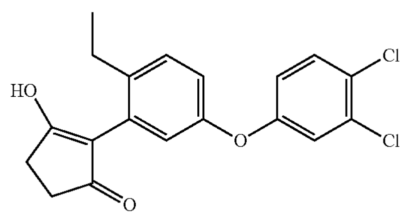 [SMILES: CCc1ccc(Oc2ccc(Cl)c(Cl)c2)cc1C1=C(O)CCC1=O] | δ 7.33 (d, 1H), 7.25 (s, 1H), 7.09 (d, 1H), 6.92 (dd, 1H), 6.85 (dd, 1H), 6.74 (d, 1H), 2.63 (s, 4H), 2.48 (q, 2H), 1.12 (t, 3H). |
| A-18 | 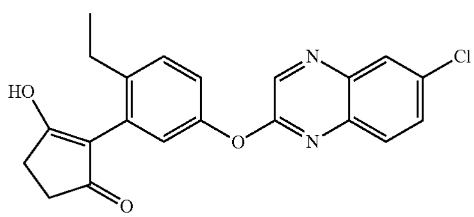 [SMILES: CCc1ccc(Oc2cnc3cc(Cl)ccc3n2)cc1C1=C(O)CCC1=O] | δ 8.71 (d, 1H), 8.03 (t, 1H), 7.67-7.58 (m, 2H), 7.37 (d, 1H), 7.12-7.09 (m, 1H), 6.92 (d, 1H), 2.61 (s, 4H), 2.56-2.50 (m, 2H), 1.15 (td, 3H). |
| A-19 | 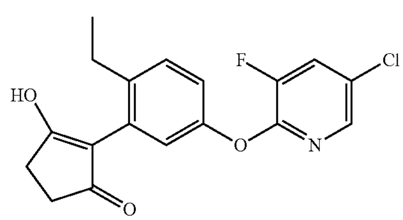 [SMILES: CCc1ccc(Oc2ncc(Cl)cc2F)cc1C1=C(O)CCC1=O] | δ 7.74 (d, 1H), 7.53 (dd, 1H), 7.31 (d, 1H), 7.03 (dd, 1H), 6.84 (d, 1H), 2.61 (s, 4H), 2.49 (q, 2H), 1.12 (t, 3H). |
| A-20 | 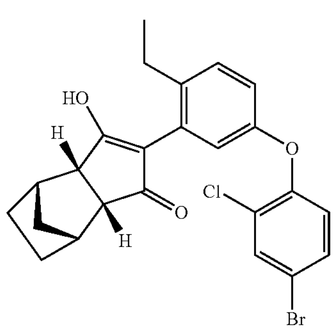 [SMILES: CCc1ccc(Oc2ccc(Br)cc2Cl)cc1C1=C(O)[C@H]2[C@H]3CC[C@H](C3)[C@H]2C1=O] | LCMS (Method B): t_r = 1.80 mins, MH⁺ = 473.0 |

TABLE T1-continued

| Compound Number | Structure | $^1$H NMR (CDCl$_3$ unless stated) or other physical data |
|---|---|---|
| A-21 | 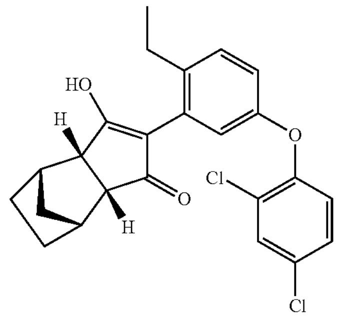 [SMILES: CCc1ccc(Oc2ccc(Cl)cc2Cl)cc1C1=C(O)[C@H]2[C@H]3CC[C@H](C3)[C@H]2C1=O] | LCMS (Method B): t$_r$ = 1.76 mins, MH$^+$ = 429.1 |
| A-22 | 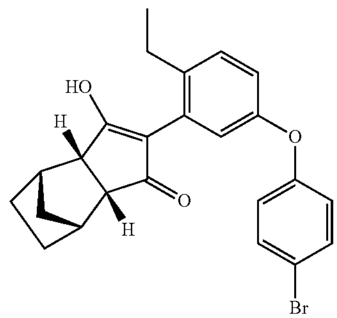 [SMILES: CCc1ccc(Oc2ccc(Br)cc2)cc1C1=C(O)[C@H]2[C@H]3CC[C@H](C3)[C@H]2C1=O] | LCMS (Method B): t$_r$ = 1.71 mins, MH$^+$ = 439.1 |
| A-23 | 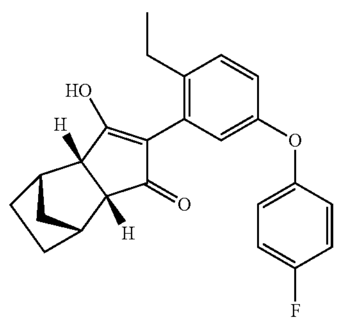 [SMILES: CCc1ccc(Oc2ccc(F)cc2)cc1C1=C(O)[C@H]2[C@H]3CC[C@H](C3)[C@H]2C1=O] | LCMS (Method B): t$_r$ = 1.59 mins, MH$^+$ = 379.2 |
| A-24 | 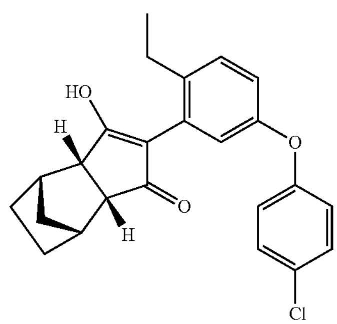 [SMILES: CCc1ccc(Oc2ccc(Cl)cc2)cc1C1=C(O)[C@H]2[C@H]3CC[C@H](C3)[C@H]2C1=O] | LCMS (Method B): t$_r$ = 1.68 mins, MH$^+$ = 395.1 |
| A-25 | 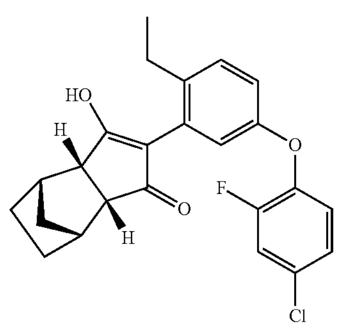 [SMILES: CCc1ccc(Oc2ccc(Cl)cc2F)cc1C1=C(O)[C@H]2[C@H]3CC[C@H](C3)[C@H]2C1=O] | LCMS (Method B): t$_r$ = 1.68 mins, MH$^+$ = 413.1 |

TABLE T1-continued

| Compound Number | Structure | ¹H NMR (CDCl₃ unless stated) or other physical data |
|---|---|---|
| A-26 | 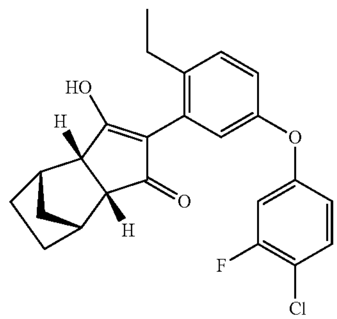 [SMILES: CCc1ccc(Oc2ccc(Cl)c(F)c2)cc1C1=C(O)[C@H]2[C@H]3CC[C@H](C3)[C@H]2C1=O] | LCMS (Method B): t$_r$ = 1.71 mins, MH⁺ = 413.1 |
| A-27 | 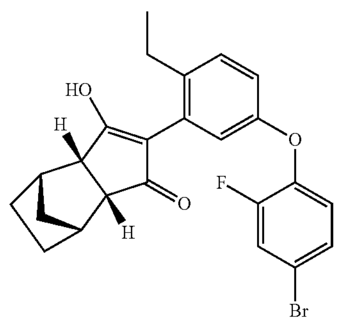 [SMILES: CCc1ccc(Oc2ccc(Br)cc2F)cc1C1=C(O)[C@H]2[C@H]3CC[C@H](C3)[C@H]2C1=O] | LCMS (Method B): t$_r$ = 1.71 mins, MH⁺ = 457.1 |
| A-28 | 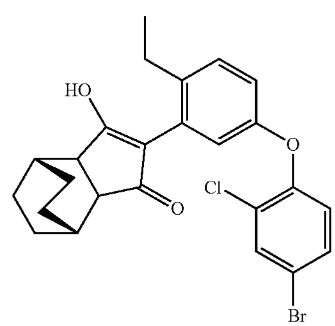 [SMILES: CCc1ccc(Oc2ccc(Br)cc2Cl)cc1C1=C(O)C2C(C1=O)[C@H]1CC[C@@H]2CC1] | δ 7.61-7..59 (m, 1H), 7.35-7.28 (m, 2H), 6.95-6.83 (m, 3H). 6.71 (br. s, 1H), 2.51 (q, 2H), 2.15 (br. s, 1H), 1.74-1.54 (m, 8H), 1.14 (t, 3H). |
| A-29 | 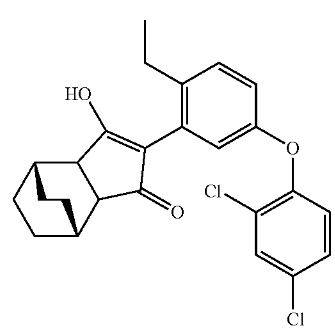 [SMILES: CCc1ccc(Oc2ccc(Cl)cc2Cl)cc1C1=C(O)C2C(C1=O)[C@H]1CC[C@@H]2CC1] | LCMS (Method B): t$_r$ = 1.86 mins, MH⁺ = 443.1 |

TABLE T1-continued

| Compound Number | Structure | ¹H NMR (CDCl₃ unless stated) or other physical data |
| --- | --- | --- |
| A-30 | 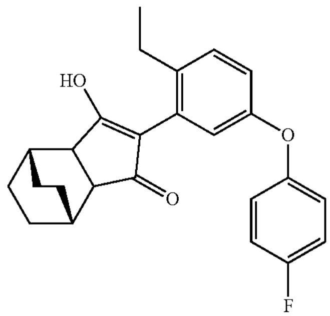 [SMILES: CCc1ccc(Oc2ccc(F)cc2)cc1C1=C(O)C2C(C1=O)[C@H]1CC[C@@H]2CC1] | LCMS (Method B): $t_r$ = 1.67 mins, MH⁺ = 393.2 |
| A-31 | 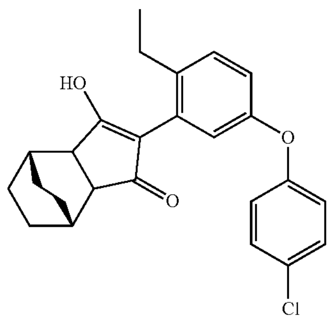 [SMILES: CCc1ccc(Oc2ccc(Cl)cc2)cc1C1=C(O)C2C(C1=O)[C@H]1CC[C@@H]2CC1] | LCMS (Method B): $t_r$ = 1.76 mins, MH⁺ = 409.1 |
| A-32 | 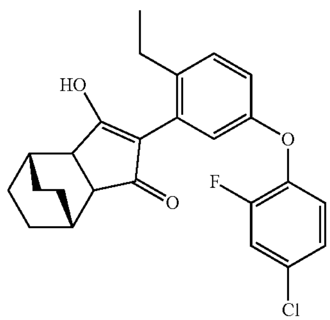 [SMILES: CCc1ccc(Oc2ccc(Cl)cc2F)cc1C1=C(O)C2C(C1=O)[C@H]1CC[C@@H]2CC1] | LCMS (Method B): $t_r$ = 1.77 mins, MH⁺ = 427.1 |
| A-33 | 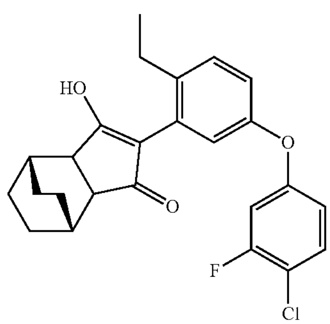 [SMILES: CCc1ccc(Oc2ccc(Cl)c(F)c2)cc1C1=C(O)C2C(C1=O)[C@H]1CC[C@@H]2CC1] | LCMS (Method B): $t_r$ = 1.80 mins, MH⁺ = 427.1 |
| A-34 | 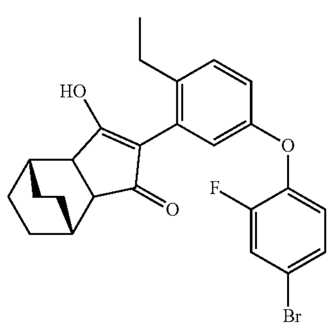 [SMILES: CCc1ccc(Oc2ccc(Br)cc2F)cc1C1=C(O)C2C(C1=O)[C@H]1CC[C@@H]2CC1] | LCMS (Method B): $t_r$ = 1.80 mins, MH⁺ = 471.1 |

TABLE T1-continued

| Compound Number | Structure | $^1$H NMR (CDCl$_3$ unless stated) or other physical data |
|---|---|---|
| A-35 | 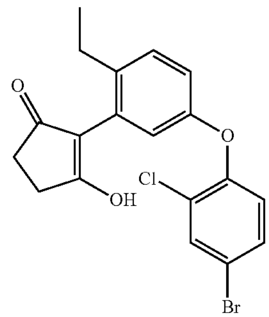 [SMILES: CCc1ccc(Oc2ccc(Br)cc2Cl)cc1C1=C(O)CCC1=O] | LCMS (Method B): t$_r$ = 1.63 mins, MH$^+$ = 409.0 |
| A-36 | 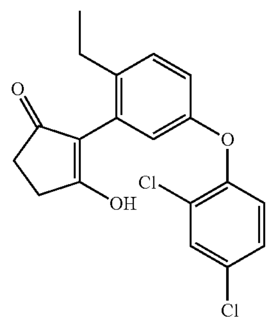 [SMILES: CCc1ccc(Oc2ccc(Cl)cc2Cl)cc1C1=C(O)CCC1=O] | LCMS (Method B): t$_r$ = 1.60 mins, MH$^+$ = 363.0 |
| A-37 | 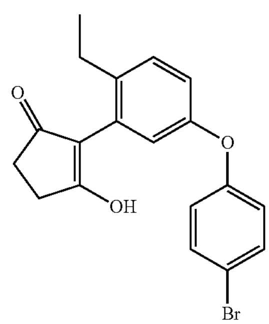 | LCMS (Method B): t$_r$ = 1.63 mins, MH$^+$ = 373.0 |
| A-38 | 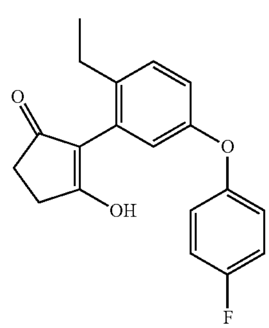 [SMILES: CCc1ccc(Oc2ccc(F)cc2)cc1C1=C(O)CCC1=O] | LCMS (Method B): t$_r$ = 1.44 mins, MH$^+$ = 313.1 |

TABLE T1-continued

| Compound Number | Structure | $^1$H NMR (CDCl$_3$ unless stated) or other physical data |
|---|---|---|
| A-39 | 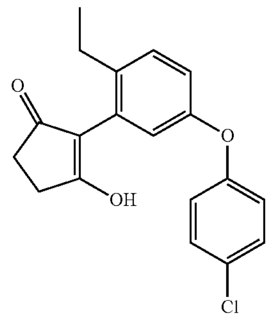 [SMILES: CCc1ccc(Oc2ccc(Cl)cc2)cc1C1=C(O)CCC1=O] | LCMS (Method B): t$_r$ = 1.52 mins, MH$^+$ = 329.1 |
| A-40 | 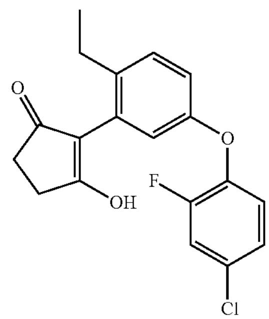 [SMILES: CCc1ccc(Oc2ccc(Cl)cc2F)cc1C1=C(O)CCC1=O] | LCMS (Method B): t$_r$ = 1.54 mins, MH$^+$ = 347.1 |
| A-41 | 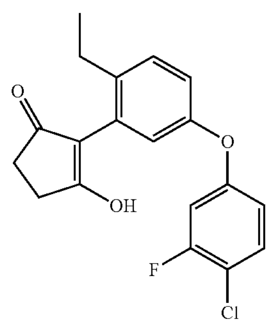 [SMILES: CCc1ccc(Oc2ccc(Cl)c(F)c2)cc1C1=C(O)CCC1=O] | LCMS (Method B): t$_r$ = 1.56 mins, MH$^+$ = 347.1 |
| A-42 | 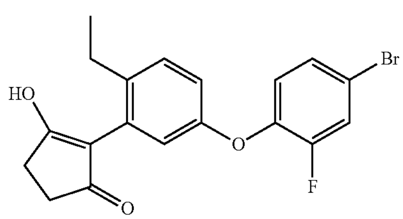 [SMILES: CCc1ccc(Oc2ccc(Br)cc2F)cc1C1=C(O)CCC1=O] | LCMS (Method B): t$_r$ = 1.56 mins, MH$^+$ = 391.0 |
| A-43 | 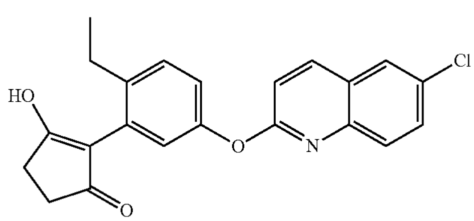 [SMILES: CCc1ccc(Oc2ccc3cc(Cl)ccc3n2)cc1C1=C(O)CCC1=O] | d$_4$-MeOH δ 8.25 (d, 1H), 7.89 (d, 1H), 7.71 (d, 1H), 7.61 (dd, 1H), 7.37 (d, 1H), 7.20 (d, 1H), 7.12 (dd, 1H), 6.90 (d, 1H), 2.65 (s, 4H), 2.54 (q, 2H), 1.15 (t, 3H). |

TABLE T1-continued
| Compound Number | Structure | ¹H NMR (CDCl₃ unless stated) or other physical data |
|---|---|---|
| A-44 | 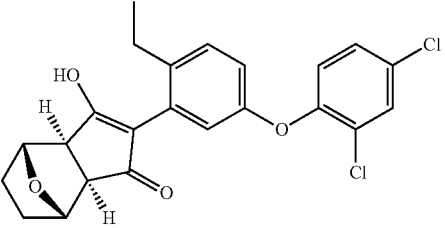 [SMILES: CCc1ccc(Oc2ccc(Cl)cc2Cl)cc1C1=C(O)[C@H]2[C@@H](C1=O)[C@@H]1CC[C@H]2O1] | d₄-MeOH δ 7.52 (d, 1H), 7.28-7.24 (m, 2H), 7.00 (d, 1H), 6.86 (dd, 1H), 6.62 (d, 1H), 4.60-4.59 (m, 2H), 2.84 (s, 2H), 2.46 (q, 2H), 1.82-1.80 (m, 2H), 1.68-1.64 (m, 2H), 1.08 (t, 3H). |
| A-45 | 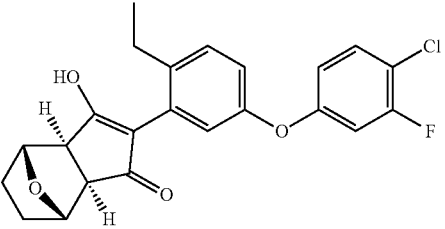 | δ 7.30-7.25 (m, 2H), 6.95 (dd, 1H), 6.79 (dd, 1H), 6.72 (dt, 2H), 4.68-4.67 (m, 2H), 2.78 (s, 2H), 2.46 (q, 2H), 1.85-1.82 (m, 2H), 1.59-1.55 (m, 2H), 1.11 (t, 3H). |
| A-46 | 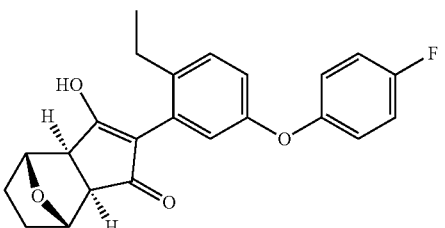 | δ 7.25 (d, 1H), 7.03-6.89 (m, 5H), 6.66 (br. s, 1H), 4.70-4.68 (m, 2H), 2.79 (br. s, 2H), 2.45 (q 2H), 1.86-1.83 (m, 2H), 1.58-1.57 (m, 2H), 1.10 (t, 3H). |
| A-47 | 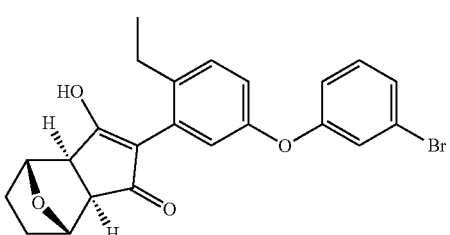 | δ 7.25-7.12 (m, 3H), 6.95-6.89 (m, 2H), 6.75-6.70 (m, 1H), 4.67-4.66 (m, 2H), 2.77 (s, 2H), 2.46 (q, 2H), 1.84-1.81 (m, 2H), 1.56-1.54 (m, 2H), 1.11 (t, 3H). |
| A-48 | 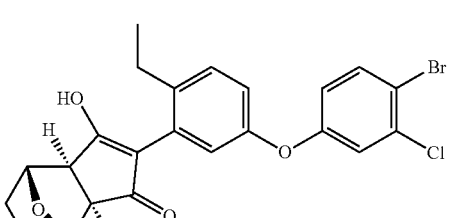 | LCMS (Method A): t_r = 1.71 mins, MH⁺ = 475 |
| A-49 | 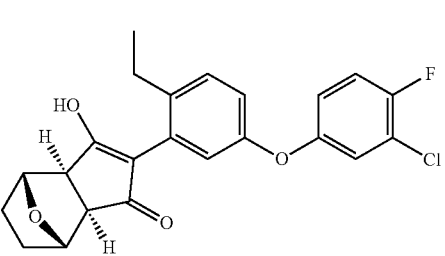 [SMILES: CCc1ccc(Oc2ccc(F)c(Cl)c2)cc1C1=C(O)[C@H]2[C@@H](C1=O)[C@@H]1CC[C@H]2O1] | δ 7.28-7.25 (m, 1H), 7.08-7.04 (m, 2H), 6.93-6.90 (m, 1H), 6.88-6.83 (m, 1H), 6.69-6.67 (m, 1H), 4.69-4.68 (m, 2H), 2.79 (br. s, 1H), 2.45 (q, 2H), 1.85-1.83 (m, 2H), 1.58-1.56 (m, 2H), 1.11 (t, 3H). |

TABLE T1-continued

| Compound Number | Structure | ¹H NMR (CDCl₃ unless stated) or other physical data |
|---|---|---|
| A-50 | 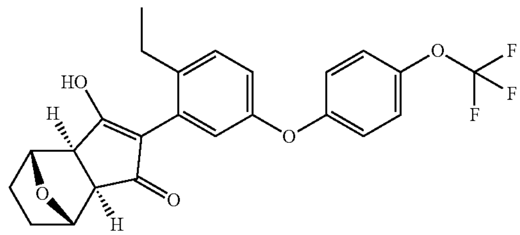 [SMILES: CCc1ccc(Oc2ccc(OC(F)(F)F)cc2)cc1C1=C(O)[C@H]2[C@@H](C1=O)[C@@H]1CC[C@H]2O1] | δ 7.30-7.28 (m, 1H), 7.17 (d, 2H), 7.00 (d, 2H), 6.96 (dd, 1H), 6.74-6.71 (m, 1H), 4.72-4.71 (m, 2H), 2.82 (br. s, 2H), 2.47 (q, 2H), 1.87-1.85 (m, 2H), 1.60-1.56 (m, 2H), 1.12 (t, 3H). |
| A-51 | 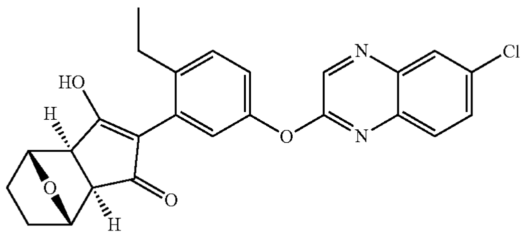 [SMILES: CCc1ccc(Oc2cnc3cc(Cl)ccc3n2)cc1C1=C(O)[C@H]2[C@@H](C1=O)[C@@H]1CC[C@H]2O1] | δ 8.73 (s, 1H), 8.07 (d, 1H), 7.95 (s, 1H), 7.67 (d, 1H), 7.61 (dd, 1H), 7.39 (d, 1H), 7.12 (dd, 1H), 4.74-4.71 (br. m, 2H), 2.68-2.57 (br. m, 4H), 1.84 (br. app. s, 2H), 1.61-1.59 (br. m, 2H), 1.17 (t, 3H). |
| A-52 | 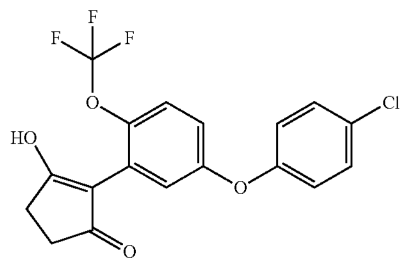 [SMILES: O=C1CCC(O)=C1c1cc(Oc2ccc(Cl)cc2)ccc1OC(F)(F)F] | δ 7.33-7.29 (m, 3H), 7.13 (d, 1H), 7.00-6.95 (m, 3H), 2.68 (s, 4H). |
| A-53 | 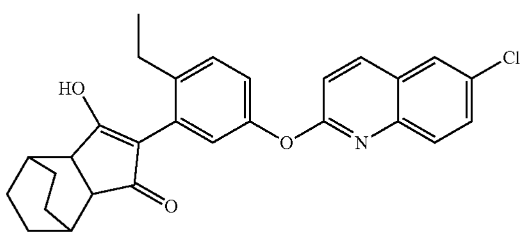 [SMILES: CCc1ccc(Oc2ccc3cc(Cl)ccc3n2)cc1C1=C(O)C2C3CCC(CC3)C2C1=O] | d₄-MeOH δ 8.26 (d, 1H), 7.90 (d, 1H), 7.71 (d, 1H), 7.63-7.60 (m, 1H), 7.40 (d, 1H), 7.22 (d, 1H), 7.15 (dd, 1H), 6.90 (d, 1H), 2.79 (br. s, 2H), 2.59 (q, 2H), 2.09 (br. s, 2H), 1.78-1.71 (m, 4H), 1.63-1.55 (br. m, 2H), 1.48-1.40 (br. m, 2H), 1.19 (t, 3H). |
| A-54 | 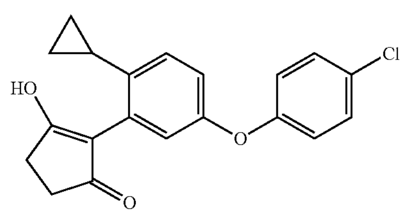 [SMILES: O=C1CCC(O)=C1c1cc(Oc2ccc(Cl)cc2)ccc1C1CC1] | CDCl₃ + 2 drops d₆-DMSO: δ 7.24 (d, 2H), 6.98-6.91 (m, 3H), 6.82 (dd, 1H), 6.78 (s, 1H), 2.65-2.56 (m, 4H), 1.89-1.80 (m, 1H), 0.84-0.76 (m, 2H), 0.58-0.52 (m, 2H). |
| A-55 | 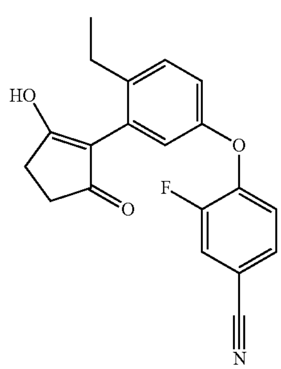 [SMILES: CCc1ccc(Oc2ccc(C#N)cc2F)cc1C1=C(O)CCC1=O] | LCMS (Method B): t$_r$ = 1.45 mins, MH⁺ = 338.1 |

TABLE T1-continued

| Compound Number | Structure | ¹H NMR (CDCl₃ unless stated) or other physical data |
|---|---|---|
| A-56 | 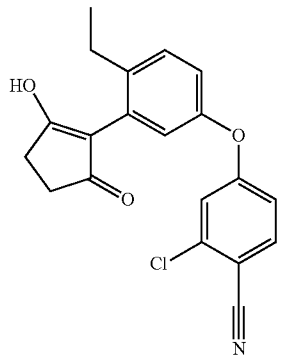 [SMILES: CCc1ccc(Oc2ccc(C#N)c(Cl)c2)cc1C1=C(O)CCC1=O] | LCMS (Method B): $t_r$ = 1.48 mins, MH⁺ = 354.1 |
| A-57 | 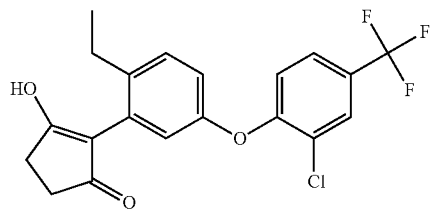 [SMILES: CCc1ccc(Oc2ccc(C(F)(F)F)cc2Cl)cc1C1=C(O)CCC1=O] | LCMS (Method B): $t_r$ = 1.66 mins, MH⁺ = 397.1 |
| A-58 | 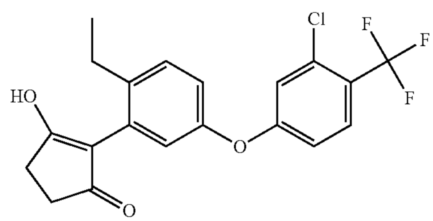 [SMILES: CCc1ccc(Oc2ccc(C(F)(F)F)c(Cl)c2)cc1C1=C(O)CCC1=O] | LCMS (Method B): $t_r$ = 1.70 mins, MH⁺ = 397.1 |
| A-59 | 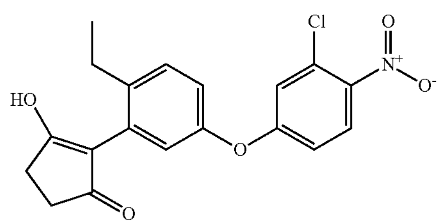 [SMILES: CCc1ccc(Oc2ccc([N+](=O)[O-])c(Cl)c2)cc1C1=C(O)CCC1=O] | LCMS (Method B): $t_r$ = 1.53 mins, MH⁺ = 374.1 |
| A-60 | 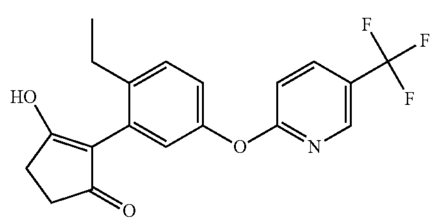 [SMILES: CCc1ccc(Oc2ccc(C(F)(F)F)cn2)cc1C1=C(O)CCC1=O] | LCMS (Method B): $t_r$ = 1.46 mins, MH⁺ = 364.1 |
| A-61 | 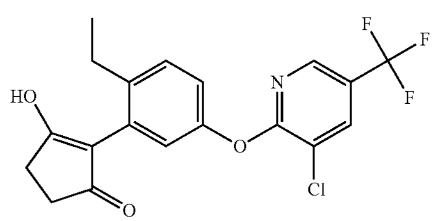 [SMILES: CCc1ccc(Oc2ncc(C(F)(F)F)cc2Cl)cc1C1=C(O)CCC1=O] | LCMS (Method B): $t_r$ = 1.52 mins, MH⁺ = 398.1 |

TABLE T1-continued
| Compound Number | Structure | ¹H NMR (CDCl₃ unless stated) or other physical data |
|---|---|---|
| A-62 | 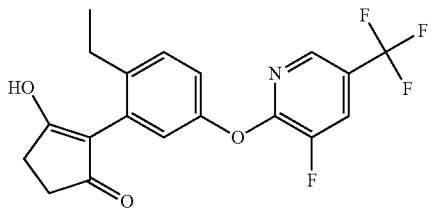 [SMILES: CCc1ccc(Oc2ncc(C(F)(F)F)cc2F)cc1C1=C(O)CCC1=O] | LCMS (Method B): $t_r$ = 1.51 mins, MH⁺ = 382.1 |
| A-63 | 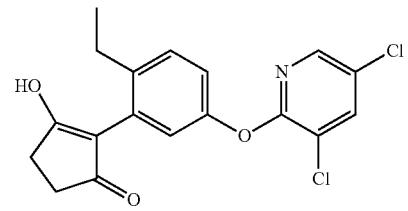 [SMILES: CCc1ccc(Oc2ncc(Cl)cc2Cl)cc1C1=C(O)CCC1=O] | δ 7.86 (d, 1H), 7.72-7.72 (m, 1H), 7.25 (d, 1H), 6.99 (dd, 1H), 6.82 (d, 1H), 2.56 (s, 4H), 2.47 (q, 2H), 1.10 (t, 3H). |
| A-64 | 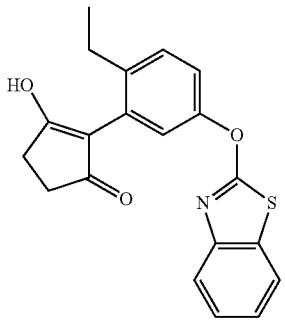 [SMILES: CCc1ccc(Oc2nc3ccccc3s2)cc1C1=C(O)CCC1=O] | LCMS (Method B): $t_r$ = 1.46 mins, MH⁺ = 352.1 |
| A-65 | 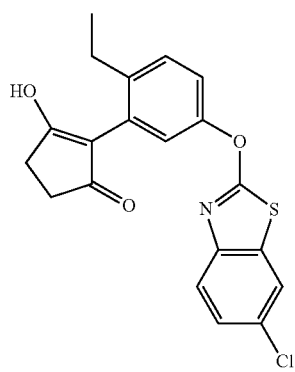 [SMILES: CCc1ccc(Oc2nc3ccc(Cl)cc3s2)cc1C1=C(O)CCC1=O] | LCMS (Method B): $t_r$ = 1.60 mins, MH⁺ = 386.1 |
| A-66 | 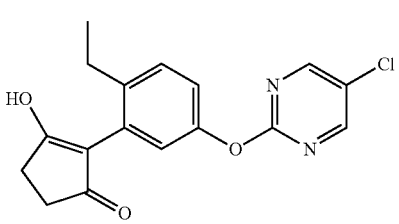 [SMILES: CCc1ccc(Oc2ncc(Cl)cn2)cc1C1=C(O)CCC1=O] | LCMS (Method B): $t_r$ = 1.25 mins, MH⁺ = 331.1 |

TABLE T1-continued

| Compound Number | Structure | $^1$H NMR (CDCl$_3$ unless stated) or other physical data |
|---|---|---|
| A-67 | 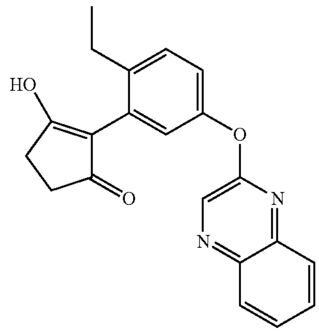 [SMILES: CCc1ccc(Oc2cnc3ccccc3n2)cc1C1=C(O)CCC1=O] | LCMS (Method B): t$_r$ = 1.36 mins, MH$^+$ = 347.1 |
| A-68 | 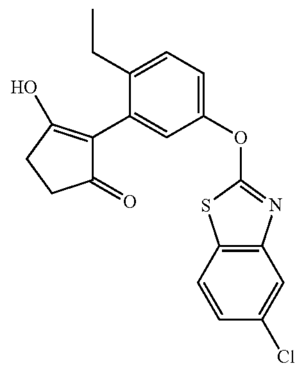 [SMILES: CCc1ccc(Oc2nc3cc(Cl)ccc3s2)cc1C1=C(O)CCC1=O] | LCMS (Method B): t$_r$ = 1.54 mins, MH$^+$ = 386.1 |
| A-69 | 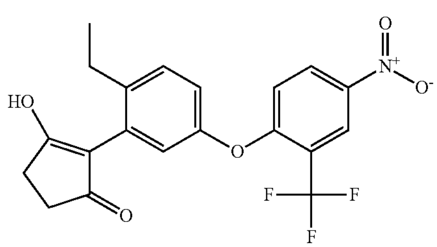 [SMILES: CCc1ccc(Oc2ccc([N+](=O)[O-])cc2C(F)(F)F)cc1C1=C(O)CCC1=O] | LCMS (Method B): t$_r$ = 1.54 mins, MH$^+$ = 408.1 |
| A-70 | 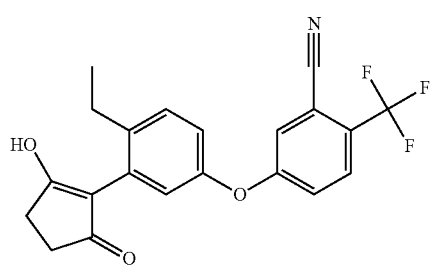 [SMILES: CCc1ccc(Oc2ccc(C(F)(F)F)c(C#N)c2)cc1C1=C(O)CCC1=O] | LCMS (Method B): t$_r$ = 1.56 mins, MH$^+$ = 388.1 |
| A-71 | 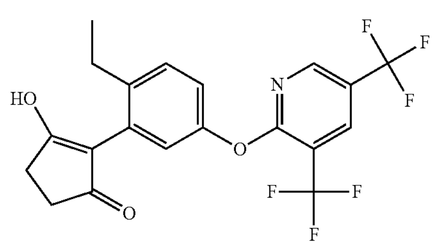 [SMILES: CCc1ccc(Oc2ncc(C(F)(F)F)cc2C(F)(F)F)cc1C1=C(O)CCC1=O] | LCMS (Method B): t$_r$ = 1.63 mins, MH$^+$ = 432.1 |

TABLE T1-continued

| Compound Number | Structure | $^1$H NMR (CDCl$_3$ unless stated) or other physical data |
| --- | --- | --- |
| A-72 | 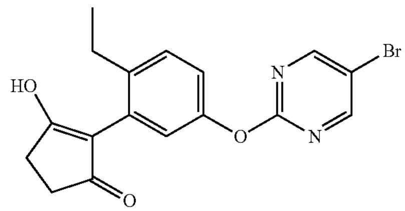 [SMILES: CCc1ccc(Oc2ncc(Br)cn2)cc1C1=C(O)CCC1=O] | LCMS (Method B): t$_r$ = 1.26 mins, MH$^+$ = 375.0 |
| A-73 | 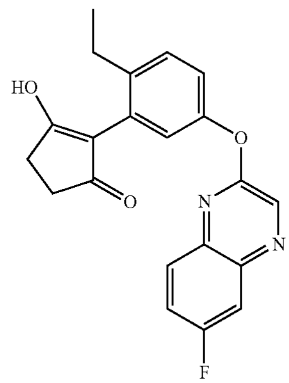 [SMILES: CCc1ccc(Oc2cnc3cc(F)ccc3n2)cc1C1=C(O)CCC1=O] | LCMS (Method B): t$_r$ = 1.41 mins, MH$^+$ = 365.1 |
| A-74 | 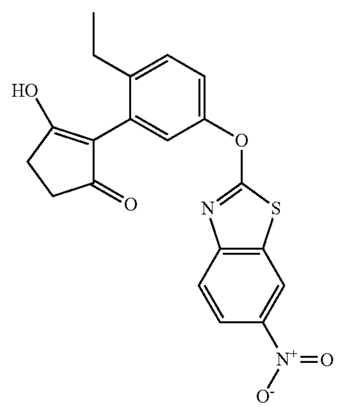 [SMILES: CCc1ccc(Oc2nc3ccc([N+](=O)[O-])cc3s2)cc1C1=C(O)CCC1=O] | LCMS (Method B): t$_r$ = 1.46 mins, MH$^+$ = 397.1 |
| A-75 | 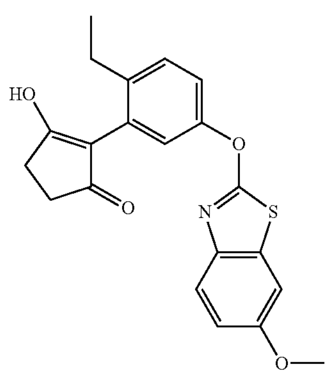 [SMILES: CCc1ccc(Oc2nc3ccc(OC)cc3s2)cc1C1=C(O)CCC1=O] | LCMS (Method B): t$_r$ = 1.48 mins, MH$^+$ = 382.1 |
| A-76 | 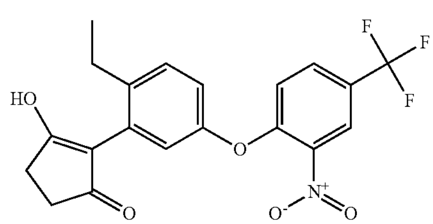 [SMILES: CCc1ccc(Oc2ccc(C(F)(F)F)cc2[N+](=O)[O-])cc1C1=C(O)CCC1=O] | LCMS (Method B): t$_r$ = 1.52 mins, MH$^+$ = 408.1 |

TABLE T1-continued
| Compound Number | Structure | ¹H NMR (CDCl₃ unless stated) or other physical data |
|---|---|---|
| A-77 | 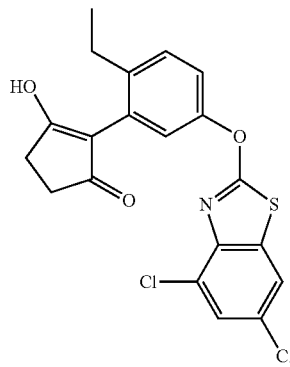 | LCMS (Method B): $t_r$ = 1.64 mins, MH⁺ = 420.0 |
| A-78 | 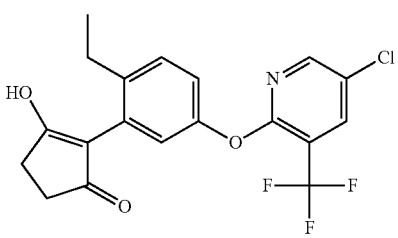 [SMILES: CCc1ccc(Oc2ncc(Cl)cc2C(F)(F)F)cc1C1=C(O)CCC1=O] | LCMS (Method B): $t_r$ = 1.56 mins, MH⁺ = 398.1 |
| A-79 | 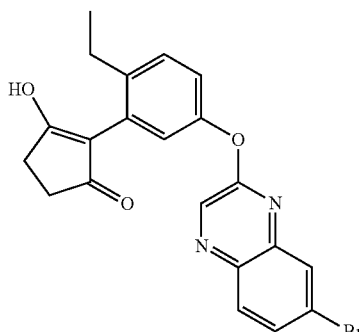 | LCMS (Method B): $t_r$ = 1.47 mins, MH⁺ = 427.0 |
| A-80 | 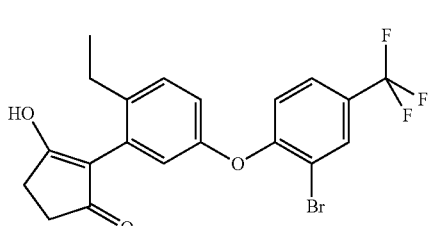 | LCMS (Method B): $t_r$ = 1.64 mins, MH⁺ = 441.0 |
| A-81 | 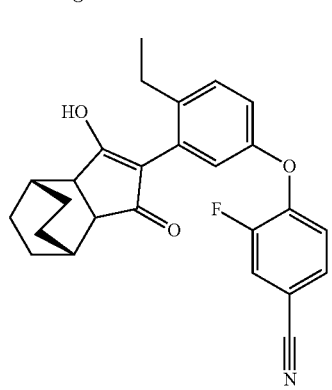 | LCMS (Method B): $t_r$ = 1.78 mins, MH⁺ = 418.2 |

TABLE T1-continued

| Compound Number | Structure | $^1$H NMR (CDCl$_3$ unless stated) or other physical data |
| --- | --- | --- |
| A-82 | 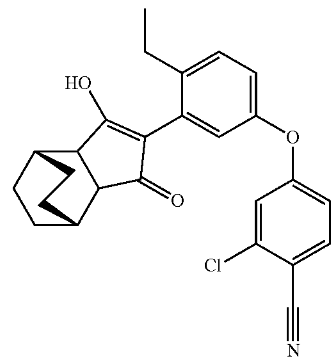 [SMILES: CCc1ccc(Oc2ccc(C#N)c(Cl)c2)cc1C1=C(O)C2C(C1=O)[C@H]1CC[C@@H]2CC1] | LCMS (Method B): t$_r$ = 1.71 mins, MH$^+$ = 434.1 |
| A-83 | 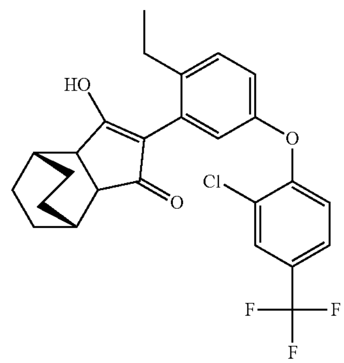 [SMILES: CCc1ccc(Oc2ccc(C(F)(F)F)cc2Cl)cc1C1=C(O)C2C(C1=O)[C@H]1CC[C@@H]2CC1] | LCMS (Method B): t$_r$ = 1.87 mins, MH$^+$ = 477.1 |
| A-84 | 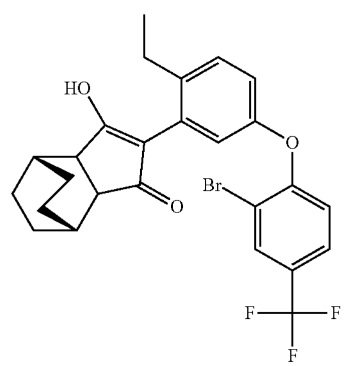 [SMILES: CCc1ccc(Oc2ccc(C(F)(F)F)cc2Br)cc1C1=C(O)C2C(C1=O)[C@H]1CC[C@@H]2CC1] | LCMS (Method B): t$_r$ = 1.89 mins, MH$^+$ = 521.1 |
| A-85 | 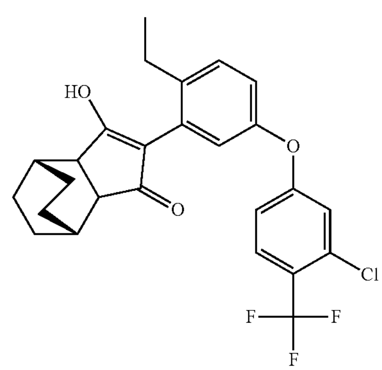 [SMILES: CCc1ccc(Oc2ccc(C(F)(F)F)c(Cl)c2)cc1C1=C(O)C2C(C1=O)[C@H]1CC[C@@H]2CC1] | LCMS (Method B): t$_r$ = 1.89 mins, MH$^+$ = 477.1 |

TABLE T1-continued
| Compound Number | Structure | $^1$H NMR (CDCl$_3$ unless stated) or other physical data |
|---|---|---|
| A-86 | 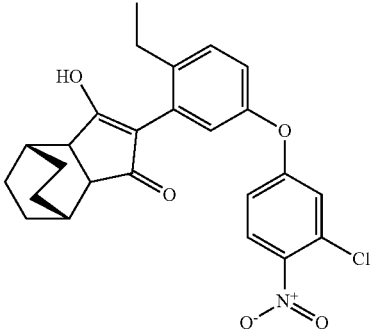 [SMILES: CCc1ccc(Oc2ccc([N+](=O)[O-])c(Cl)c2)cc1C1=C(O)C2C(C1=O)[C@H]1CC[C@@H]2CC1] | LCMS (Method B): t$_r$ = 1.74 mins, MH$^+$ = 454.1 |
| A-87 | 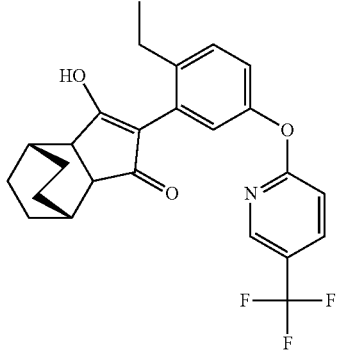 [SMILES: CCc1ccc(Oc2ccc(C(F)(F)F)cn2)cc1C1=C(O)C2C(C1=O)[C@H]1CC[C@@H]2CC1] | LCMS (Method B): t$_r$ = 1.69 mins, MH$^+$ = 444.2 |
| A-88 | 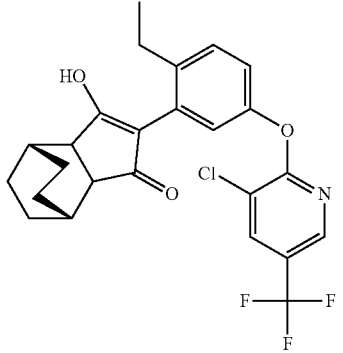 [SMILES: CCc1ccc(Oc2ncc(C(F)(F)F)cc2Cl)cc1C1=C(O)C2C(C1=O)[C@H]1CC[C@@H]2CC1] | LCMS (Method B): t$_r$ = 1.73 mins, MH$^+$ = 478.1 |
| A-89 | 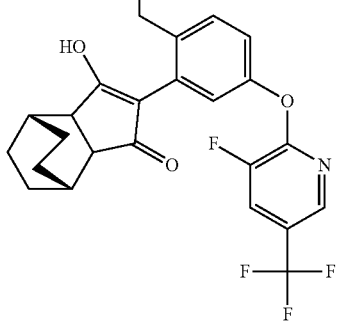 | LCMS (Method B): t$_r$ = 1.72 mins, MH$^+$ = 462.2 |

TABLE T1-continued

| Compound Number | Structure | $^1$H NMR (CDCl$_3$ unless stated) or other physical data |
|---|---|---|
| A-90 | 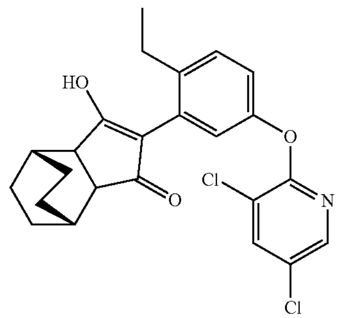 [SMILES: CCc1ccc(Oc2ncc(Cl)cc2Cl)cc1C1=C(O)C2C(C1=O)[C@H]1CC[C@@H]2CC1] | LCMS (Method B): t$_r$ = 1.74 mins, MH$^+$ = 444.1 |
| A-91 | 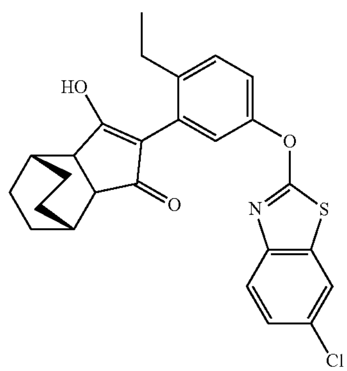 [SMILES: CCc1ccc(Oc2nc3ccc(Cl)cc3s2)cc1C1=C(O)C2C(C1=O)[C@H]1CC[C@@H]2CC1] | LCMS (Method B): t$_r$ = 1.82 mins, MH$^+$ = 466.1 |
| A-92 | 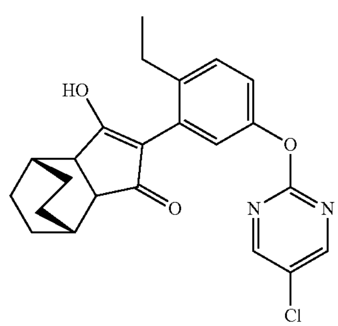 [SMILES: CCc1ccc(Oc2ncc(Cl)cn2)cc1C1=C(O)C2C(C1=O)[C@H]1CC[C@@H]2CC1] | LCMS (Method B): t$_r$ = 1.51 mins, MH$^+$ = 411.1 |
| A-93 | 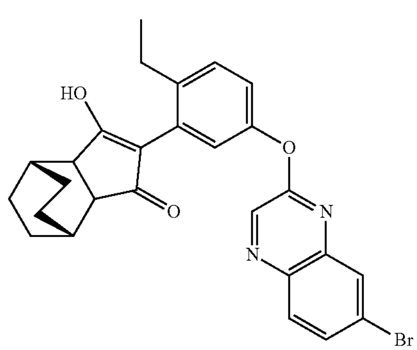 [SMILES: CCc1ccc(Oc2cnc3ccc(Br)cc3n2)cc1C1=C(O)C2C(C1=O)[C@H]1CC[C@@H]2CC1] | LCMS (Method B): t$_r$ = 1.76 mins, MH$^+$ = 505.1 |

TABLE T1-continued

| Compound Number | Structure | $^1$H NMR (CDCl$_3$ unless stated) or other physical data |
|---|---|---|
| A-94 | 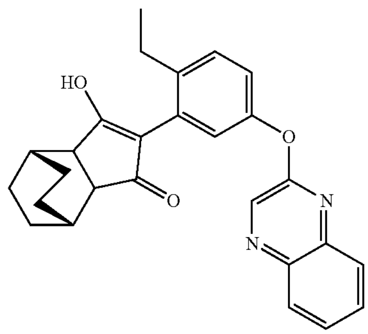 | LCMS (Method B): t$_r$ = 1.72 mins, MH$^+$ = 468.2 |
| A-95 | 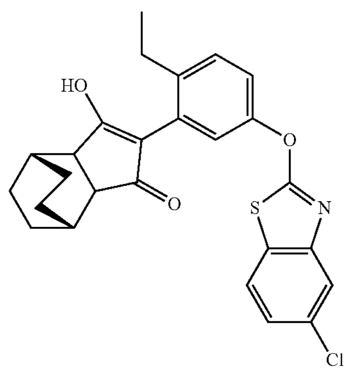 | LCMS (Method B): t$_r$ = 1.61 mins, MH$^+$ = 427.2 |
| A-96 | 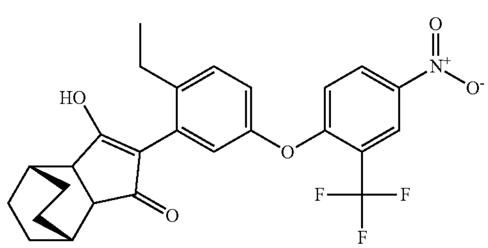 | LCMS (Method B): t$_r$ = 1.82 mins, MH$^+$ = 466.1 |
| A-97 | 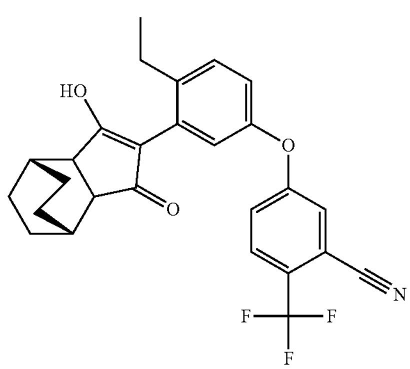 | LCMS (Method B): t$_r$ = 1.77 mins, MH$^+$ = 488.2 |
| A-98 | 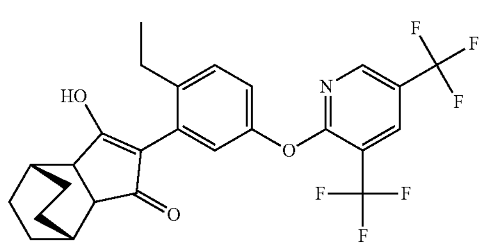 | LCMS (Method B): t$_r$ = 1.76 mins, MH$^+$ = 468.2 |

TABLE T1-continued

| Compound Number | Structure | $^1$H NMR (CDCl$_3$ unless stated) or other physical data |
|---|---|---|
| A-99 | 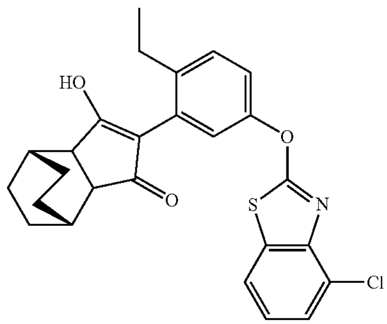 | LCMS (Method B): $t_r$ = 1.81 mins, MH$^+$ = 512.2 |
| A-100 | 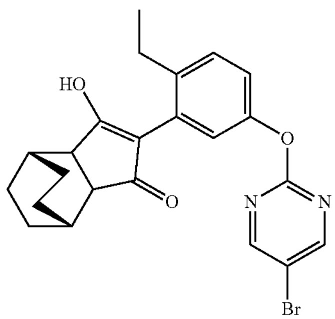 | LCMS (Method B): $t_r$ = 1.76 mins, MH$^+$ = 466.1 |
| A-101 | 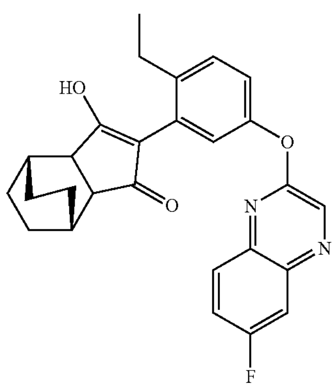 | LCMS (Method B): $t_r$ = 1.52 mins, MH$^+$ = 455.1 |
| A-102 | 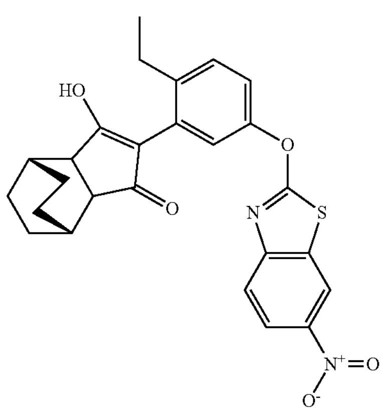 | LCMS (Method B): $t_r$ = 1.66 mins, MH$^+$ = 445.2 |

TABLE T1-continued

| Compound Number | Structure | ¹H NMR (CDCl₃ unless stated) or other physical data |
|---|---|---|
| A-103 | 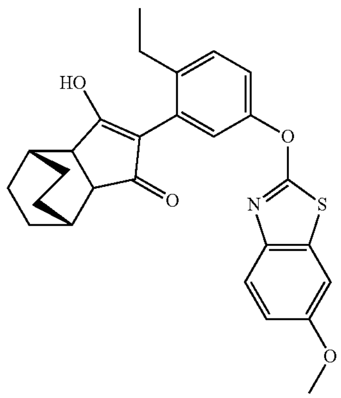 | LCMS (Method B): $t_r$ = 1.72 mins, MH⁺ = 477.1 |
| A-104 | 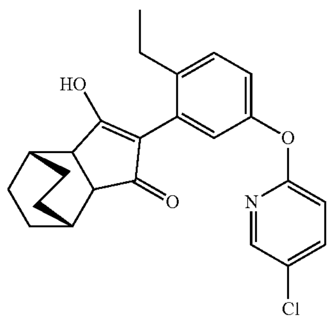 | LCMS (Method B): $t_r$ = 1.71 mins, MH⁺ = 462.2 |
| A-105 | 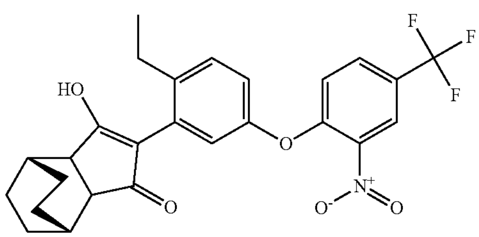 [SMILES: CCc1ccc(Oc2ccc(C(F)(F)F)cc2[N+](=O)[O-])cc1C1=C(O)C2C(C1=O)[C@H]1CC[C@@H]2CC1] | LCMS (Method B): $t_r$ = 1.77 mins, MH⁺ = 488.2 |
| A-106 | 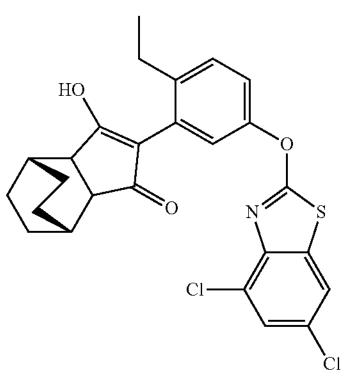 [SMILES: CCc1ccc(Oc2nc3c(Cl)cc(Cl)cc3s2)cc1C1=C(O)C2C(C1=O)[C@H]1CC[C@@H]2CC1] | LCMS (Method B): $t_r$ = 1.91 mins, MH⁺ = 500.1 |
| A-107 | 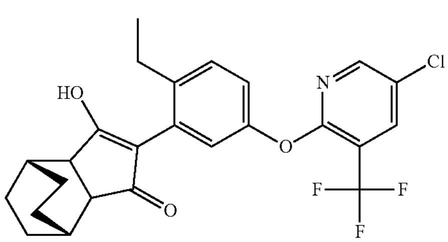 [SMILES: CCc1ccc(Oc2ncc(Cl)cc2C(F)(F)F)cc1C1=C(O)C2C(C1=O)[C@H]1CC[C@@H]2CC1] | LCMS (Method B): $t_r$ = 1.77 mins, MH⁺ = 478.1 |

TABLE T1-continued

| Compound Number | Structure | ¹H NMR (CDCl₃ unless stated) or other physical data |
|---|---|---|
| A-108 | 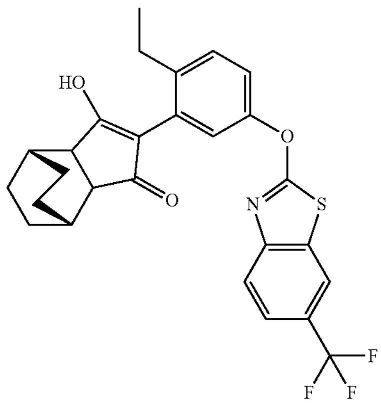 [SMILES: CCc1ccc(Oc2nc3ccc(C(F)(F)F)cc3s2)cc1C1=C(O)C2C(C1=O)[C@H]1CC[C@@H]2CC1] | LCMS (Method B): t$_r$ = 1.84 mins, MH⁺ = 500.1 |
| A-109 | 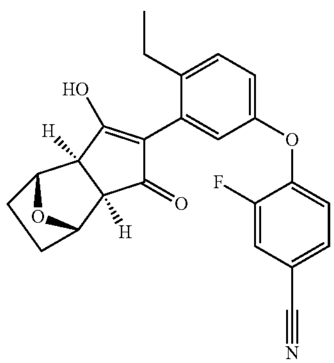 [SMILES: CCc1ccc(Oc2ccc(C#N)cc2F)cc1C1=C(O)[C@H]2[C@@H](C1=O)[C@@H]1CC[C@H]2O1] | LCMS (Method B): t$_r$ = 1.31 mins, MH⁺ = 406.1 |
| A-110 | 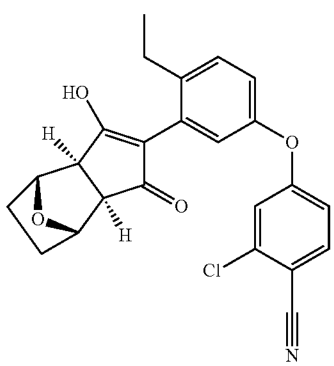 [SMILES: CCc1ccc(Oc2ccc(C#N)c(Cl)c2)cc1C1=C(O)[C@H]2[C@@H](C1=O)[C@@H]1CC[C@H]2O1] | LCMS (Method B): t$_r$ = 1.37 mins, MH⁺ = 422.1 |
| A-111 | 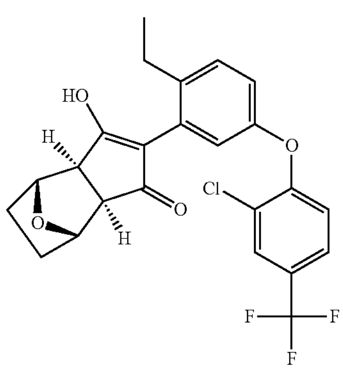 [SMILES: CCc1ccc(Oc2ccc(C(F)(F)F)cc2Cl)cc1C1=C(O)[C@H]2[C@@H](C1=O)[C@@H]1CC[C@H]2O1] | LCMS (Method B): t$_r$ = 1.52 mins, MH⁺ = 465.1 |

TABLE T1-continued

| Compound Number | Structure | ¹H NMR (CDCl₃ unless stated) or other physical data |
|---|---|---|
| A-112 | 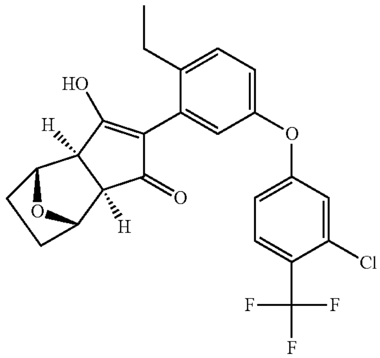 [SMILES: CCc1ccc(Oc2ccc(C(F)(F)F)c(Cl)c2)cc1C1=C(O)[C@H]2[C@@H](C1=O)[C@@H]1CC[C@H]2O1] | LCMS (Method B): $t_r$ = 1.54 mins, MH⁺ = 465.1 |
| A-113 | 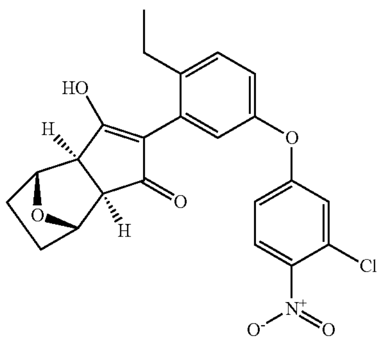 [SMILES: CCc1ccc(Oc2ccc([N+](=O)[O-])c(Cl)c2)cc1C1=C(O)[C@H]2[C@@H](C1=O)[C@@H]1CC[C@H]2O1] | LCMS (Method B): $t_r$ = 1.41 mins, MH⁺ = 442.1 |
| A-114 | 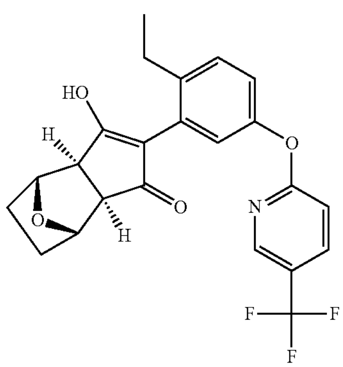 [SMILES: CCc1ccc(Oc2ccc(C(F)(F)F)cn2)cc1C1=C(O)[C@H]2[C@@H](C1=O)[C@@H]1CC[C@H]2O1] | LCMS (Method B): $t_r$ = 1.34 mins, MH⁺ = 432.1 |
| A-115 | 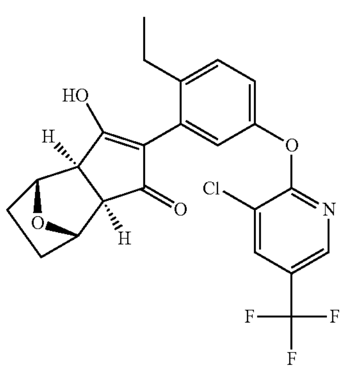 [SMILES: CCc1ccc(Oc2ncc(C(F)(F)F)cc2Cl)cc1C1=C(O)[C@H]2[C@@H](C1=O)[C@@H]1CC[C@H]2O1] | LCMS (Method B): $t_r$ = 1.44 mins, MH⁺ = 466.1 |

TABLE T1-continued

| Compound Number | Structure | $^1$H NMR (CDCl$_3$ unless stated) or other physical data |
|---|---|---|
| A-116 | 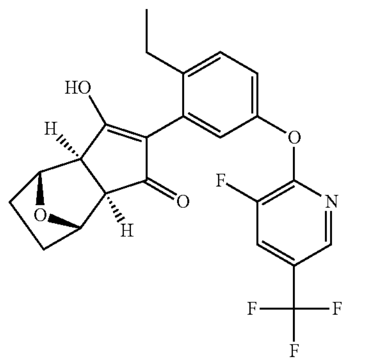 [SMILES: CCc1ccc(Oc2ncc(C(F)(F)F)cc2F)cc1C1=C(O)[C@H]2[C@@H](C1=O)[C@@H]1CC[C@H]2O1] | LCMS (Method B): t$_r$ = 1.37 mins, MH$^+$ = 450.1 |
| A-117 | 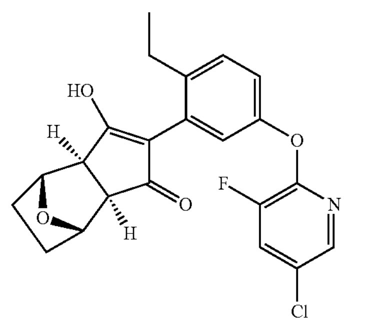 [SMILES: CCc1ccc(Oc2ncc(Cl)cc2F)cc1C1=C(O)[C@H]2[C@@H](C1=O)[C@@H]1CC[C@H]2O1] | LCMS (Method B): t$_r$ = 1.32 mins, MH$^+$ = 416.1 |
| A-118 | 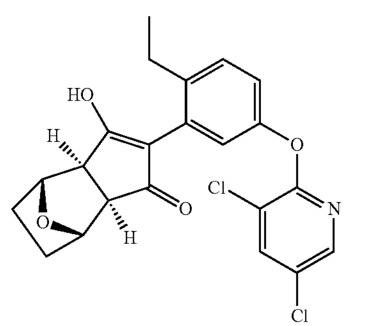 [SMILES: CCc1ccc(Oc2ncc(Cl)cc2Cl)cc1C1=C(O)[C@H]2[C@@H](C1=O)[C@@H]1CC[C@H]2O1] | LCMS (Method B): t$_r$ = 1.39 mins, MH$^+$ = 432.1 |
| A-119 | 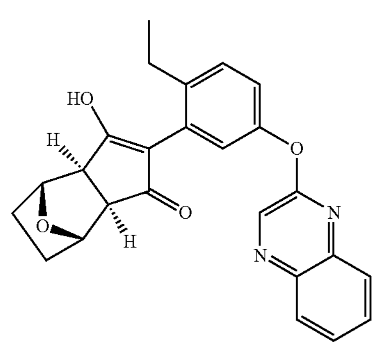 [SMILES: CCc1ccc(Oc2cnc3ccccc3n2)cc1C1=C(O)[C@H]2[C@@H](C1=O)[C@@H]1CC[C@H]2O1] | LCMS (Method B): t$_r$ = 1.24 mins, MH$^+$ = 415.2 |

TABLE T1-continued

| Compound Number | Structure | $^1$H NMR (CDCl$_3$ unless stated) or other physical data |
|---|---|---|
| A-120 | 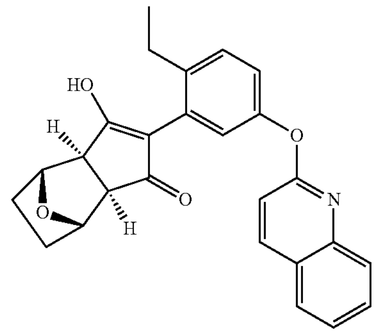 [SMILES: CCc1ccc(Oc2ccc3ccccc3n2)cc1C1=C(O)[C@H]2[C@@H](C1=O)[C@@H]1CC[C@H]2O1] | LCMS (Method B): t$_r$ = 1.31 mins, MH$^+$ = 414.2 |
| A-121 | 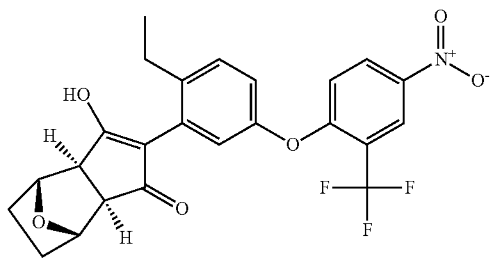 [SMILES: CCc1ccc(Oc2ccc([N+](=O)[O-])cc2C(F)(F)F)cc1C1=C(O)[C@H]2[C@@H](C1=O)[C@@H]1CC[C@H]2O1] | LCMS (Method B): t$_r$ = 1.46 mins, MH$^+$ = 476.1 |
| A-122 | 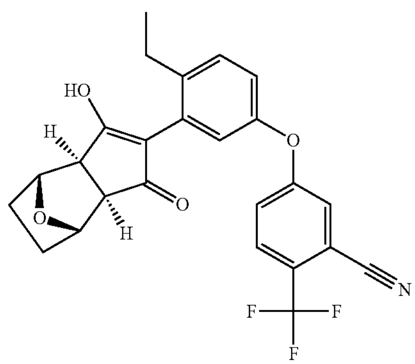 [SMILES: CCc1ccc(Oc2ccc(C(F)(F)F)c(C#N)c2)cc1C1=C(O)[C@H]2[C@@H](C1=O)[C@@H]1CC[C@H]2O1] | LCMS (Method B): t$_r$ = 1.42 mins, MH$^+$ = 456.1 |
| A-123 | 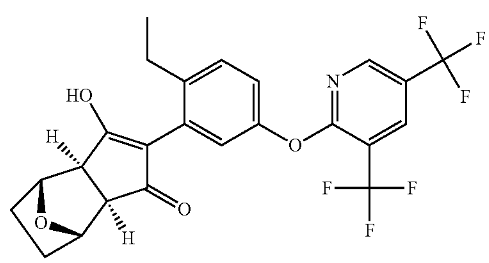 [SMILES: CCc1ccc(Oc2ncc(C(F)(F)F)cc2C(F)(F)F)cc1C1=C(O)[C@H]2[C@@H](C1=O)[C@@H]1CC[C@H]2O1] | LCMS (Method B): t$_r$ = 1.49 mins, MH$^+$ = 500.1 |
| A-124 | 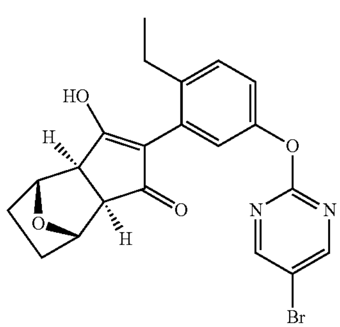 [SMILES: CCc1ccc(Oc2ncc(Br)cn2)cc1C1=C(O)[C@H]2[C@@H](C1=O)[C@@H]1CC[C@H]2O1] | LCMS (Method B): t$_r$ = 1.16 mins, MH$^+$ = 443.1 |

It should be noted that certain compounds of the invention exist as a mixture in any ratio of isomers, including atropisomers, noted above, under the conditions used to obtain the $^1$H NMR data. Where this has occurred, the characterising data are reported for all isomers present at ambient temperature in the specified solvent. Unless otherwise stated, proton NMR spectra were recorded at ambient temperature. Compounds characterised by HPLC-MS were analysed using one of two methods described below.

Method A

Compounds characterised by HPLC-MS were analysed using a Waters 2795 HPLC equipped with a Waters Atlantis dC18 column (column length 20 mm, internal diameter of column 3 mm, particle size 3 micron, temperature 40° C.), Waters photodiode array and Micromass ZQ2000. The analysis was conducted using a three minute run time, according to the following gradient table:

| Time (mins) | Solvent A (%) | Solvent B (%) | Flow (ml/mn) |
|---|---|---|---|
| 0.00 | 90.0 | 10.0 | 2.00 |
| 0.25 | 90.0 | 100 | 2.00 |
| 2.00 | 10.0 | 90.0 | 2.00 |
| 2.50 | 10.0 | 90.0 | 2.00 |
| 2.60 | 90.0 | 10.0 | 2.00 |
| 3.0 | 90.0 | 10.0 | 2.00 |

Solvent A: H$_2$O containing 0.1% HCOOH
Solvent B: CH$_3$CN containing 0.1% HCOOH Method B Compounds characterised by HPLC-MS were analysed using an Waters 2777 injector with a 1525 micro pump HPLC equipped with a Waters Atlantis dC18 IS column (column length 20 mm, internal diameter of column 3 mm, particle size 3 micron), Waters 2996 photodiode array, Waters 2420 ELSD and Micromass ZQ2000. The analysis was conducted using a three minute run time, according to the following gradient table:

| Time (mins) | Solvent A (%) | Solvent B (%) | Flow (ml/mn) |
|---|---|---|---|
| 0.00 | 95.0 | 5 | 1.300 |
| 2.50 | 0.0 | 100 | 1.300 |
| 2.80 | 0.00 | 100 | 1.300 |
| 2.90 | 95.0 | 5 | 1.300 |

Solvent A: H$_2$O with 0.05% TFA
Solvent B: CH$_3$CN with 0.05% TFA

The characteristic values obtained for each compound were the retention time (rt, recorded in minutes) and the molecular ion (typically the cation MH$^+$), as listed in Table T1.

The compounds of the following Tables 1 to 39 can be obtained in an analogous manner.

Table 1 covers compounds of the following type

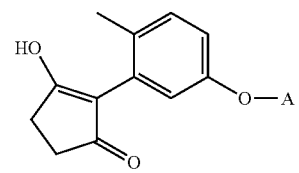

wherein A is as defined in Table 1.

TABLE 1

| Compound Number | A | Compound Number | A |
|---|---|---|---|
| 1.001 | phenyl | 1.002 | 2-bromophenyl |
| 1.003 | 2-chlorophenyl | 1.004 | 2-cyanophenyl |
| 1.005 | 2-difluoromethoxyphenyl | 1.006 | 2-fluorophenyl |
| 1.007 | 2-methoxyphenyl | 1.008 | 2-methylphenyl |
| 1.009 | 2-nitrophenyl | 1.010 | 2-trifluoromethoxyphenyl |
| 1.011 | 2-trifluoromethylphenyl | 1.012 | 3-bromophenyl |
| 1.013 | 3-chlorophenyl | 1.014 | 3-cyanophenyl |
| 1.015 | 3-difluoromethoxyphenyl | 1.016 | 3-fluorophenyl |
| 1.017 | 3-methoxyphenyl | 1.018 | 3-methylphenyl |
| 1.019 | 3-nitrophenyl | 1.020 | 3-trifluoromethoxyphenyl |
| 1.021 | 3-trifluoromethylphenyl | 1.022 | 4-bromophenyl |
| 1.023 | 4-chlorophenyl | 1.024 | 4-cyanophenyl |
| 1.025 | 4-difluoromethoxyphenyl | 1.026 | 4-fluorophenyl |
| 1.027 | 4-methanesulfonyl | 1.028 | 4-methoxyphenyl |
| 1.029 | 4-methylphenyl | 1.030 | 4-nitrophenyl |
| 1.031 | 4-trifluoromethoxyphenyl | 1.032 | 4-trifluoromethylphenyl |
| 1.033 | 4-bromo-2-chlorophenyl | 1.034 | 2,4-dichlorophenyl |
| 1.035 | 2-chloro-4-cyanophenyl | 1.036 | 2-chloro-4-difluoromethoxyphenyl |
| 1.037 | 2-chloro-4-fluorophenyl | 1.038 | 2-chloro-4-methoxyphenyl |
| 1.039 | 2-chloro-4-methylphenyl | 1.040 | 2-chloro-4-nitrophenyl |
| 1.041 | 2-chloro-4-trifluoromethoxyphenyl | 1.042 | 2-chloro-4-trifluoromethylphenyl |
| 1.043 | 4-bromo-3-chlorophenyl | 1.044 | 3,4-dichlorophenyl |
| 1.045 | 3-chloro-4-cyanophenyl | 1.046 | 3-chloro-4-difluoromethoxyphenyl |
| 1.047 | 3-chloro-4-fluorophenyl | 1.048 | 3-chloro-4-methoxyphenyl |
| 1.049 | 3-chloro-4-methylphenyl | 1.050 | 3-chloro-4-nitrophenyl |
| 1.051 | 3-chloro-4-trifluoromethoxyphenyl | 1.052 | 3-chloro-4-trifluoromethylphenyl |
| 1.053 | 2-bromo-4-chlorophenyl | 1.054 | 4-chloro-2-difluoromethoxyphenyl |
| 1.055 | 4-chloro-2-cyanophenyl | 1.056 | 4-chloro-2-methoxyphenyl |
| 1.057 | 4-chloro-2-fluorophenyl | 1.058 | 4-chloro-2-nitrophenyl |
| 1.059 | 4-chloro-2-methylphenyl | 1.060 | 4-chloro-2-trifluoromethylphenyl |
| 1.061 | 4-chloro-2-trifluoromethoxyphenyl | 1.062 | 4-chloro-3-trifluoromethoxyphenyl |
| 1.063 | 3-bromo-4-chlorophenyl | 1.064 | 4-chloro-3-difluoromethoxyphenyl |
| 1.065 | 4-chloro-3-cyanophenyl | 1.066 | 4-chloro-3-methoxyphenyl |
| 1.067 | 4-chloro-3-fluorophenyl | 1.068 | 4-chloro-3-nitrophenyl |
| 1.069 | 4-chloro-3-methylphenyl | 1.070 | 4-chloro-3-trifluoromethylphenyl |

TABLE 1-continued

| Compound Number | A | Compound Number | A |
|---|---|---|---|
| 1.071 | 4-bromo-2-fluorophenyl | 1.072 | 2-difluoro-4-difluoromethoxyphenyl |
| 1.073 | 4-cyano-2-fluorophenyl | 1.074 | 2-fluoro-4-methoxyphenyl |
| 1.075 | 2,4-fluorophenyl | 1.076 | 2-fluoro-4-nitrophenyl |
| 1.077 | 2-fluoro-4-methylphenyl | 1.078 | 2-fluoro-4-trifluoromethylphenyl |
| 1.079 | 2-fluoro-4-trifluoromethoxyphenyl | 1.080 | 4-bromo-3-fluorophenyl |
| 1.081 | 4-cyano-3-fluorophenyl | 1.082 | 3-difluoro-4-difluoromethoxyphenyl |
| 1.083 | 3,4-fluorophenyl | 1.084 | 3-fluoro-4-methoxyphenyl |
| 1.085 | 3-fluoro-4-methylphenyl | 1.086 | 3-fluoro-4-nitrophenyl |
| 1.087 | 3-fluoro-4-trifluoromethoxyphenyl | 1.088 | 3-fluoro-4-trifluoromethylphenyl |
| 1.089 | 4-chloro-2,3-difluorophenyl | 1.090 | 4-chloro-2,5-difluorophenyl |
| 1.091 | 4-chloro-2,6-difluorophenyl | 1.092 | 4-chloro-3,5-difluorophenyl |
| 1.093 | 2,4-dichloro-3-fluorophenyl | 1.094 | 2,4-dichloro-5-fluorophenyl |
| 1.095 | 2,4-dichloro-6-fluorophenyl | 1.096 | 2,3,4-trifluorophenyl |
| 1.097 | 2,4,6-trifluorophenyl | 1.098 | 2,4,5-trifluorophenyl |
| 1.099 | 3,4,5-trifluorophenyl | 1.100 | pentafluorophenyl |
| 1.101 | 2-bromo-4-cyanophenyl | 1.102 | 3-bromo-4-cyanophenyl |
| 1.103 | 4-bromo-2-cyanophenyl | 1.104 | 4-bromo-3-cyanophenyl |
| 1.105 | 2-cyano-4-nitrophenyl | 1.106 | 3-cyano-4-nitrophenyl |
| 1.107 | 2-cyano-4-trifluoromethylphenyl | 1.108 | 3-cyano-4-trifluoromethylphenyl |
| 1.109 | 2,4-dicyanophenyl | 1.110 | 3,4-dicyanophenyl |
| 1.111 | 3-chloropyridin-2-yl | 1.112 | 4-chloropyridin-2-yl |
| 1.113 | 5-chloropyridin-2-yl | 1.114 | 6-chloropyridin-2-yl |
| 1.115 | 2-chloropyridin-3-yl | 1.116 | 4-chloropyridin-3-yl |
| 1.117 | 5-chloropyridin-3-yl | 1.118 | 6-chloropyridin-3-yl |
| 1.119 | 2-chloropyridin-4-yl | 1.120 | 3-chloropyridin-4-yl |
| 1.121 | 3,4-dichloropyridin-2-yl | 1.122 | 3,5-dichloropyridin-2-yl |
| 1.123 | 3,6-dichloropyridin-2-yl | 1.124 | 2,5-dichloropyridin-3-yl |
| 1.125 | 2,6-dichloropyridin-3-yl | 1.126 | 2,3-dichloropyridin-4-yl |
| 1.127 | 2,5-dichloropyridin-4-yl | 1.128 | 3,5,6-trichloropyridin-2-yl |
| 1.129 | 3-fluoropyridin-2-yl | 1.130 | 4-fluoropyridin-2-yl |
| 1.131 | 5-fluoropyridin-2-yl | 1.132 | 6-fluoropyridin-2-yl |
| 1.133 | 2-fluoropyridin-3-yl | 1.134 | 4-fluoropyridin-3-yl |
| 1.135 | 5-fluoropyridin-3-yl | 1.136 | 6-fluoropyridin-3-yl |
| 1.137 | 2-fluoropyridin-4-yl | 1.138 | 3-fluoropyridin-4-yl |
| 1.139 | 3,4-difluoropyridin-2-yl | 1.140 | 3,5-difluoropyridin-2-yl |
| 1.141 | 3,6-difluoropyridin-2-yl | 1.142 | 2,5-difluoropyridin-3-yl |
| 1.143 | 2,6-difluoropyridin-3-yl | 1.144 | 2,3-difluoropyridin-4-yl |
| 1.145 | 2,5-difluoropyridin-4-yl | 1.146 | 3,5,6-trifluoropyridin-2-yl |
| 1.147 | 3-trifluoromethylpyridin-2-yl | 1.148 | 4-trifluoromethylpyridin-2-yl |
| 1.149 | 5-trifluoromethylpyridin-2-yl | 1.150 | 6-trifluoromethylpyridin-2-yl |
| 1.151 | 2-trifluoromethylpyridin-3-yl | 1.152 | 4-trifluoromethylpyridin-3-yl |
| 1.153 | 5-trifluoromethylpyridin-3-yl | 1.154 | 6-trifluoromethylpyridin-3-yl |
| 1.155 | 2-trifluoromethylpyridin-4-yl | 1.156 | 3-trifluoromethylpyridin-4-yl |
| 1.157 | 4-chloro-3-fluoropyridin-2-yl | 1.158 | 5-chloro-3-fluoropyridin-2-yl |
| 1.159 | 6-chloro-3-fluoropyridin-2-yl | 1.160 | 3-chloro-4-fluoropyridin-2-yl |
| 1.161 | 3-chloro-5-fluoropyridin-2-yl | 1.162 | 3-chloro-6-fluoropyridin-2-yl |
| 1.163 | 3-chloro-5-trifluoromethylpyridin-2-yl | 1.164 | 3-fluoro-5-trifluoromethylpyridin-2-yl |
| 1.165 | 6-fluoro-3,4,5-trichloropyridin-2-yl | 1.166 | 4-methyl-3,5,6-trifluoropyridin-2-yl |
| 1.167 | pyrimidin-2-yl | 1.168 | 5-fluoropyrimidin-2-yl |
| 1.169 | 5-chloropyrimidin-2-yl | 1.170 | 5-bromopyrimidin-2-yl |
| 1.171 | 6-chloropyridazin-3-yl | 1.172 | 6-bromopyridazin-3-yl |
| 1.173 | quinoline-2-yl | 1.174 | 6-fluoroquinolin-2-yl |
| 1.175 | 7-fluoroquinolin-2-yl | 1.176 | 6-chloroquinolin-2-yl |
| 1.177 | 7-chloroquinolin-2-yl | 1.178 | 6-bromoquinolin-2-yl |
| 1.179 | 7-bromoquinolin-2-yl | 1.180 | 6-trifluoromethylquinolin-2-yl |
| 1.181 | 7-trifluoromethylquinolin-2-yl | 1.182 | quinoxalin-2-yl |
| 1.183 | 6-fluoroquinoxazin-2-yl | 1.184 | 7-fluoroquinoxalin-2-yl |
| 1.185 | 6-chloroquinoxalin-2-yl | 1.186 | 7-chloroquinoxalin-2-yl |
| 1.187 | 6-bromoquinoxalin-2-yl | 1.188 | 7-bromoquinoxalin-2-yl |
| 1.189 | 6-trifluoromethylquinoxalin-2-yl | 1.190 | 7-trifluoromethylquinoxalin-2-yl |
| 1.191 | quinazolin-2-yl | 1.192 | 6-fluoroquinazolin-2-yl |
| 1.193 | 7-fluoroquinazolin-2-yl | 1.194 | 6-chloroquinazolin-2-yl |
| 1.195 | 7-chloroquinazolin-2-yl | 1.196 | 6-bromoquinazolin-2-y |
| 1.197 | 7-bromoquinazolin-2-yl | 1.198 | 6-trifluoromethylquinazolin-2-yl |
| 1.199 | 7-trifluoromethylquinazolin-2-yl | 1.200 | benzoxazol-2-yl |
| 1.201 | 5-fluorobenzoxazol-2-yl | 1.202 | 6-fluorobenzoxazol-2-yl |
| 1.203 | 5-chlorobenzoxazol-2-yl | 1.204 | 6-chlorobenzoxazol-2-yl |
| 1.205 | 5-bromobenzoxazol-2-yl | 1.206 | 6-bromobenzoxazol-2-yl |
| 1.207 | 5-trifluoromethylbenzoxazol-2-yl | 1.208 | 6-trifluoromethylbenzoxazol-2-yl |
| 1.209 | benzothiazol-2-yl | 1.210 | 5-fluorobenzothiazol-2-yl |
| 1.211 | 6-fluorobenzothiazol-2-yl | 1.212 | 5-chlorobenzothiazol-2-yl |
| 1.213 | 6-chlorobenzothiazol-2-yl | 1.214 | 5-bromobenzothiazol-2-yl |
| 1.215 | 6-bromobenzothiazol-2-yl | 1.216 | 5-trifluoromethylbenzothiazol-2-yl |
| 1.217 | 6-trifluoromethylbenzothiazol-2-yl | 1.218 | benzo[1,2,4]triazin-3-yl |
| 1.219 | 6-fluorobenzo[1,2,4]triazin-3-yl | 1.220 | 7-fluorobenzo[1,2,4]triazin-3-yl |
| 1.221 | 6-chlorobenzo[1,2,4]triazin-3-yl | 1.222 | 7-chlorobenzo[1,2,4]triazin-3-yl |
| 1.223 | 6-bromobenzo[1,2,4]triazin-3-yl | 1.224 | 7-bromo benzo[1,2,4]triazin-3-yl |

TABLE 1-continued

| Compound Number | A | Compound Number | A |
|---|---|---|---|
| 1.225 | 6-trifluoromethylbenzo[1,2,4]-triazin-3-yl | 1.226 | 7-trifluoromethylbenzo-[1,2,4]triazin-3-yl |

Table 2 covers compounds of the following type

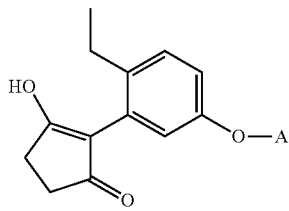

wherein A is as defined in Table 1.

Table 3 covers compounds of the following type

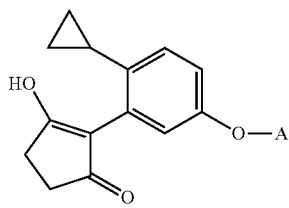

wherein A is as defined in Table 1.

Table 4 covers compounds of the following type

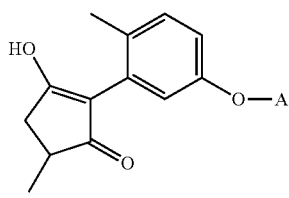

wherein A is as defined in Table 1.

Table 5 covers compounds of the following type

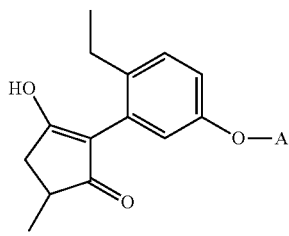

wherein A is as defined in Table 1.

Table 6 covers compounds of the following type

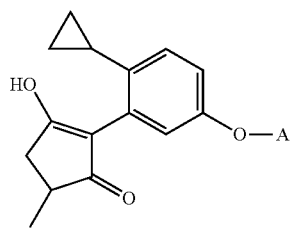

wherein A is as defined in Table 1.

Table 7 covers compounds of the following type

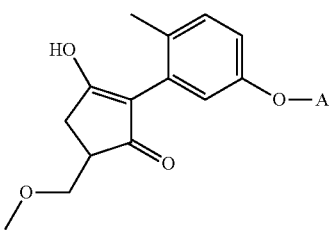

wherein A is as defined in Table 1.

Table 8 covers compounds of the following type

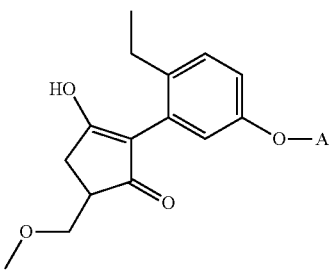

wherein A is as defined in Table 1.

Table 9 covers compounds of the following type

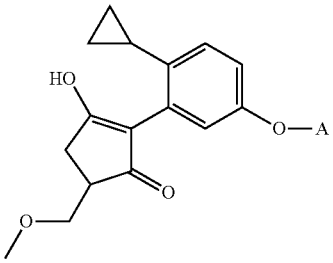

wherein A is as defined in Table 1.

Table 10 covers compounds of the following type

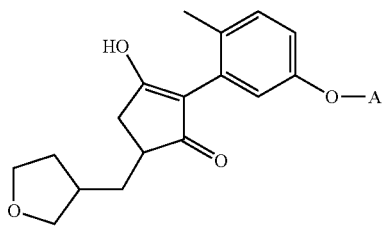

wherein A is as defined in Table 1.
Table 11 covers compounds of the following type

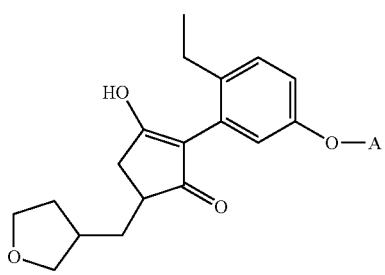

wherein A is as defined in Table 1.
Table 12 covers compounds of the following type

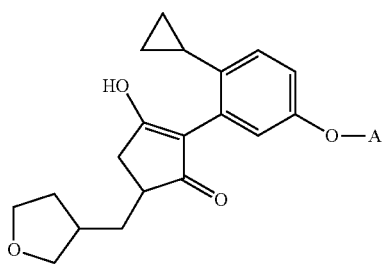

wherein A is as defined in Table 1.
Table 13 covers compounds of the following type

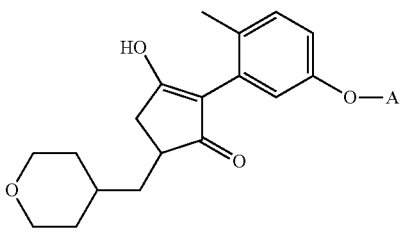

wherein A is as defined in Table 1.

Table 14 covers compounds of the following type

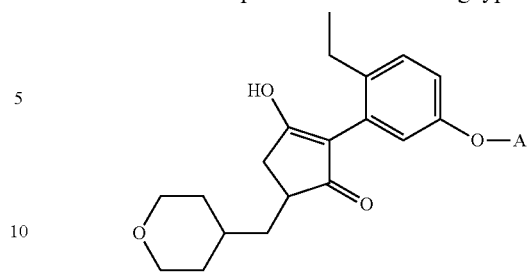

wherein A is as defined in Table 1.
Table 15 covers compounds of the following type

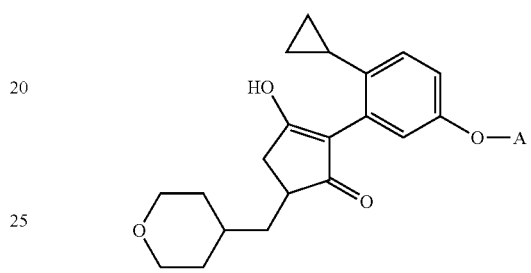

wherein A is as defined in Table 1.
Table 16 covers compounds of the following type

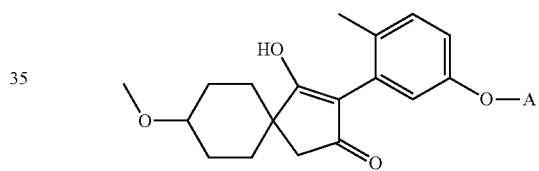

wherein A is as defined in Table 1.
Table 17 covers compounds of the following type

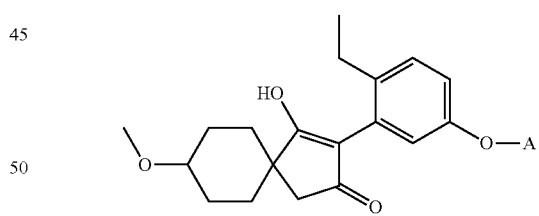

wherein A is as defined in Table 1.
Table 18 covers compounds of the following type

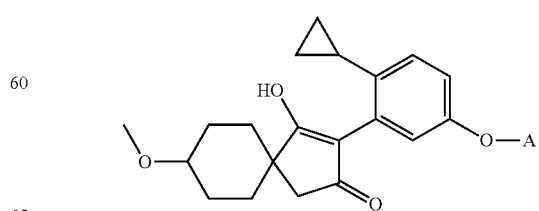

wherein A is as defined in Table 1.

Table 19 covers compounds of the following type

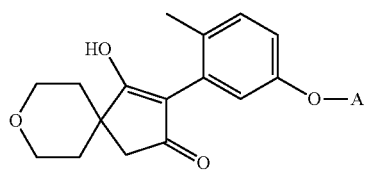

wherein A is as defined in Table 1.

Table 20 covers compounds of the following type

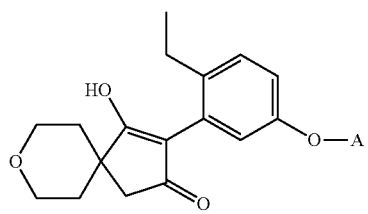

wherein A is as defined in Table 1.

Table 21 covers compounds of the following type

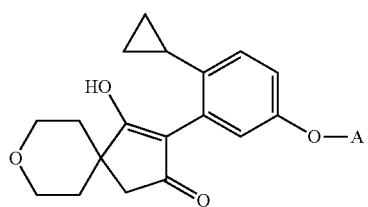

wherein A is as defined in Table 1.

Table 22 covers compounds of the following type

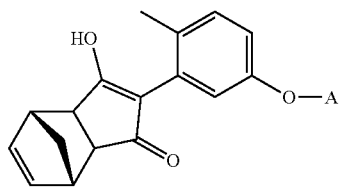

wherein A is as defined in Table 1.

Table 23 covers compounds of the following type

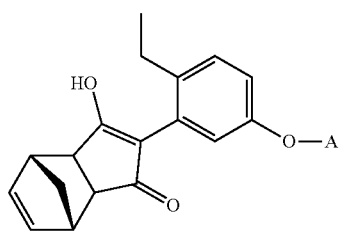

wherein A is as defined in Table 1.

Table 24 covers compounds of the following type

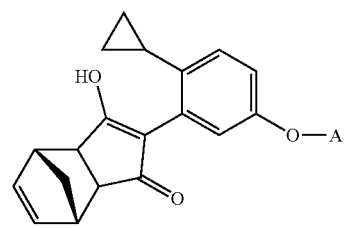

wherein A is as defined in Table 1.

Table 25 covers compounds of the following type

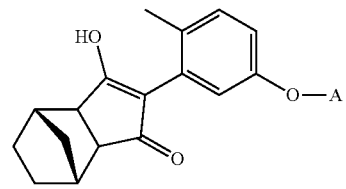

wherein A is as defined in Table 1.

Table 26 covers compounds of the following type

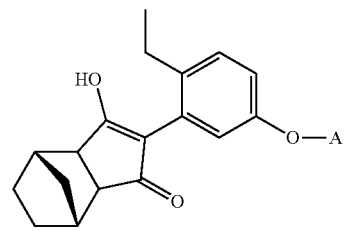

wherein A is as defined in Table 1.

Table 27 covers compounds of the following type

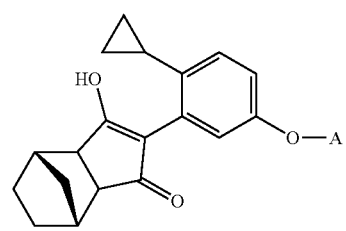

wherein A is as defined in Table 1.

Table 28 covers compounds of the following type

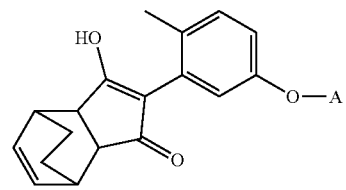

wherein A is as defined in Table 1.

Table 29 covers compounds of the following type

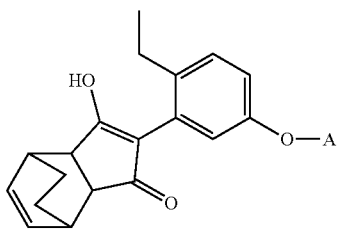

wherein A is as defined in Table 1.
Table 30 covers compounds of the following type

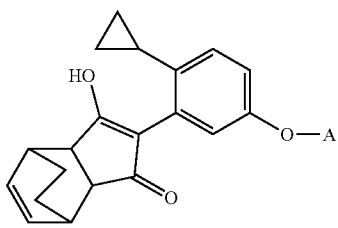

wherein A is as defined in Table 1.
Table 31 covers compounds of the following type

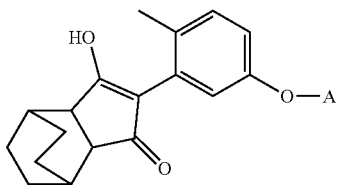

wherein A is as defined in Table 1.
Table 32 covers compounds of the following type

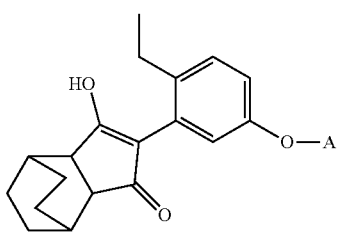

wherein A is as defined in Table 1.
Table 33 covers compounds of the following type

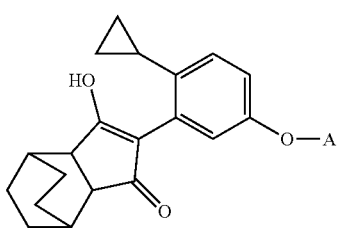

wherein A is as defined in Table 1.

Table 34 covers compounds of the following type

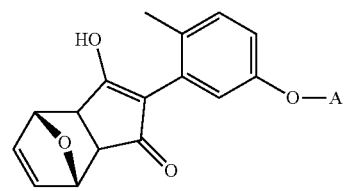

wherein A is as defined in Table 1.
Table 35 covers compounds of the following type

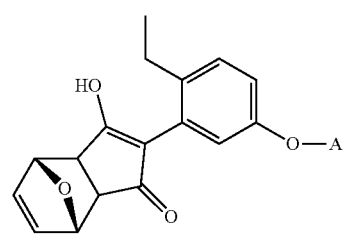

wherein A is as defined in Table 1.
Table 36 covers compounds of the following type

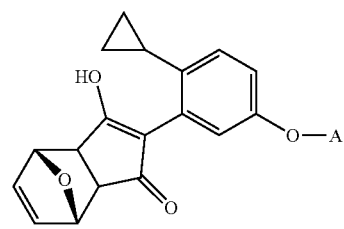

wherein A is as defined in Table 1.
Table 37 covers compounds of the following type

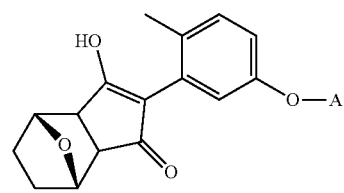

wherein A is as defined in Table 1.
Table 38 covers compounds of the following type

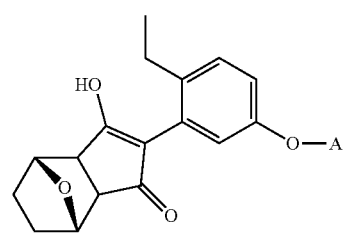

wherein A is as defined in Table 1.

Table 39 covers compounds of the following type

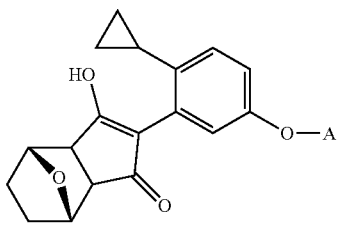

wherein A is as defined in Table 1.

Biological Examples

Seeds of a variety of test species were sown in standard soil in pots. After cultivation for one day (pre-emergence) or after 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown in a glasshouse under controlled conditions in a glasshouse (at 24/16° C., day/night; 14 hours light; 65% humidity) and watered twice daily. After 13 days for pre and post-emergence, the test was evaluated (100=total damage to plant; 0=no damage to plant).

Test Plants:

*Lolium perenne* (LOLPE), *Alopecurus myosuroides* (ALOMY), *Echinochloa crus-galli* (ECHCG), and *Avena fatua* (AVEFA).

Pre-Emergence Activity

| Compound Number | Rate g/ha | LOLPE | ALOMY | ECHCG | AVEFA |
|---|---|---|---|---|---|
| A-1 | 250 | 70 | 70 | 70 | 70 |
| A-2 | 250 | 60 | 60 | 60 | 30 |
| A-3 | 250 | 70 | 60 | 90 | 30 |
| A-4 | 250 | 90 | 80 | 100 | 90 |
| A-5 | 250 | 40 | 30 | 80 | 0 |
| A-6 | 250 | 100 | 100 | 100 | 90 |
| A-7 | 250 | 60 | 60 | 70 | 50 |
| A-8 | 250 | 40 | 0 | 40 | 0 |
| A-9 | 250 | 100 | 80 | 70 | 90 |
| A-10 | 250 | 30 | 40 | 60 | 20 |
| A-11 | 250 | 80 | 30 | 100 | 50 |
| A-12 | 250 | 70 | 60 | 70 | 30 |
| A-13 | 250 | 60 | 50 | 80 | 20 |
| A-14 | 250 | 90 | 60 | 100 | 60 |
| A-15 | 250 | 10 | 30 | 100 | 0 |
| A-16 | 250 | 70 | 40 | 90 | 30 |
| A-17 | 250 | 10 | 10 | 30 | 20 |
| A-18 | 250 | 70 | 50 | 80 | 50 |
| A-19 | 250 | 90 | 90 | 90 | 80 |
| A-20 | 250 | 50 | 50 | 60 | 10 |
| A-21 | 250 | 30 | 20 | 40 | 0 |
| A-22 | 250 | 80 | 40 | 90 | 30 |
| A-23 | 250 | 30 | 0 | 80 | 0 |
| A-24 | 250 | 40 | 10 | 50 | 30 |
| A-25 | 250 | 70 | 20 | 70 | 30 |
| A-26 | 250 | 20 | 0 | 80 | 0 |
| A-27 | 250 | 40 | 20 | 60 | 0 |
| A-28 | 250 | 0 | 0 | 20 | 0 |
| A-29 | 250 | 0 | 0 | 50 | 0 |
| A-30 | 250 | 70 | 30 | 80 | 20 |
| A-31 | 250 | 50 | 20 | 90 | 0 |
| A-32 | 250 | 40 | 0 | 60 | 0 |
| A-33 | 250 | 50 | 20 | 50 | 0 |
| A-34 | 250 | 50 | 20 | 70 | 30 |
| A-35 | 250 | 60 | 30 | 20 | 10 |
| A-37 | 250 | 10 | 10 | 20 | 0 |
| A-39 | 250 | 0 | 20 | 40 | 30 |
| A-40 | 250 | 10 | 0 | 40 | 0 |
| A-41 | 250 | 0 | 0 | 30 | 0 |
| A-42 | 250 | 0 | 0 | 30 | 0 |
| A-43 | 250 | 50 | 40 | 60 | 10 |
| A-44 | 250 | 90 | 80 | 80 | 80 |
| A-45 | 250 | 90 | 90 | 100 | 90 |
| A-46 | 250 | 80 | 80 | 100 | 60 |
| A-47 | 250 | 70 | 60 | 90 | 30 |
| A-48 | 250 | 80 | 80 | 90 | 80 |
| A-49 | 250 | 100 | 90 | 100 | 90 |
| A-50 | 250 | 100 | 100 | 100 | 100 |
| A-51 | 250 | 100 | 100 | 90 | 90 |
| A-52 | 250 | 0 | 0 | 0 | 0 |
| A-53 | 250 | 80 | 80 | 100 | 0 |
| A-54 | 250 | 0 | 0 | 0 | 0 |
| A-56 | 250 | 50 | 30 | 60 | 20 |
| A-60 | 250 | 80 | 80 | 100 | 70 |
| A-67 | 250 | 100 | 60 | 100 | 40 |
| A-70 | 250 | 20 | 0 | 60 | 10 |
| A-71 | 250 | 100 | 90 | 100 | 80 |
| A-72 | 250 | 70 | 40 | 100 | 30 |
| A-75 | 250 | 80 | 30 | 100 | 20 |
| A-76 | 250 | 50 | 20 | 100 | 0 |
| A-77 | 250 | 20 | 20 | 90 | 0 |
| A-78 | 250 | 100 | 70 | 100 | 70 |
| A-79 | 250 | 70 | 40 | 90 | 20 |
| A-80 | 250 | 50 | 0 | 80 | 10 |
| A-86 | 250 | 20 | 0 | 20 | 0 |
| A-87 | 250 | 90 | 80 | 100 | 30 |
| A-88 | 250 | 100 | 90 | 100 | 40 |
| A-89 | 250 | 100 | 50 | 100 | 70 |
| A-90 | 250 | 100 | 70 | 100 | 70 |
| A-93 | 250 | 60 | 10 | 100 | 0 |
| A-94 | 250 | 20 | 0 | 50 | 0 |
| A-95 | 250 | 100 | 70 | 100 | 30 |
| A-96 | 250 | 90 | 30 | 90 | 0 |
| A-97 | 250 | 30 | 0 | 70 | 0 |
| A-98 | 250 | 40 | 0 | 40 | 0 |
| A-99 | 250 | 90 | 70 | 100 | 50 |
| A-100 | 250 | 40 | 10 | 80 | 0 |
| A-104 | 250 | 60 | 0 | 90 | 0 |
| A-105 | 250 | 40 | 10 | 60 | 0 |
| A-108 | 250 | 50 | 30 | 80 | 10 |

Post-Emergence Activity

| Compound Number | Rate g/ha | LOLPE | ALOMY | ECHCG | AVEFA |
|---|---|---|---|---|---|
| A-1 | 250 | 80 | 100 | 100 | 80 |
| A-2 | 250 | 100 | 100 | 100 | 100 |
| A-3 | 250 | 70 | 90 | 100 | 90 |
| A-4 | 250 | 90 | 100 | 100 | 100 |
| A-5 | 250 | 30 | 30 | 80 | 10 |
| A-6 | 250 | 90 | 80 | 100 | 90 |
| A-7 | 250 | 60 | 60 | 100 | 80 |
| A-8 | 250 | 20 | 20 | 70 | 20 |
| A-9 | 250 | 70 | 90 | 90 | 100 |
| A-10 | 250 | 90 | 90 | 90 | 100 |
| A-11 | 250 | 70 | 80 | 100 | 90 |
| A-12 | 250 | 70 | 100 | 100 | 50 |
| A-13 | 250 | 90 | 90 | 100 | 100 |
| A-14 | 250 | 90 | 100 | 100 | 100 |
| A-15 | 250 | 30 | 30 | 80 | 30 |
| A-16 | 250 | 70 | 70 | 100 | 90 |

-continued

| Compound Number | Rate g/ha | LOLPE | ALOMY | ECHCG | AVEFA |
|---|---|---|---|---|---|
| A-17 | 250 | 30 | 10 | 70 | 10 |
| A-18 | 250 | 70 | 90 | 100 | 90 |
| A-19 | 250 | 50 | 80 | 100 | 60 |
| A-20 | 250 | 20 | 30 | 70 | 0 |
| A-21 | 250 | 20 | 40 | 70 | 0 |
| A-22 | 250 | 40 | 50 | 100 | 80 |
| A-23 | 250 | 20 | 50 | 60 | 0 |
| A-24 | 250 | 60 | 60 | 100 | 70 |
| A-25 | 250 | 60 | 50 | 90 | 40 |
| A-26 | 250 | 30 | 60 | 80 | 80 |
| A-27 | 250 | 80 | 60 | 80 | 70 |
| A-28 | 250 | 0 | 0 | 80 | 0 |
| A-29 | 250 | 0 | 60 | 100 | 0 |
| A-30 | 250 | 10 | 60 | 100 | 20 |
| A-31 | 250 | 40 | 100 | 100 | 80 |
| A-32 | 250 | 30 | 90 | 100 | 90 |
| A-33 | 250 | 0 | 90 | 100 | 90 |
| A-34 | 250 | 40 | 80 | 90 | 90 |
| A-35 | 250 | 20 | 10 | 30 | 20 |
| A-37 | 250 | 30 | 20 | 80 | 20 |
| A-39 | 250 | 10 | 10 | 60 | 0 |
| A-40 | 250 | 10 | 10 | 30 | 10 |
| A-41 | 250 | 20 | 0 | 70 | 10 |
| A-42 | 250 | 10 | 0 | 70 | 0 |
| A-43 | 250 | 30 | 60 | 100 | 30 |
| A-44 | 250 | 90 | 80 | 80 | 80 |
| A-45 | 250 | 90 | 90 | 100 | 90 |
| A-46 | 250 | 80 | 80 | 100 | 60 |
| A-47 | 250 | 70 | 60 | 90 | 30 |
| A-48 | 250 | 80 | 80 | 90 | 80 |
| A-49 | 250 | 100 | 90 | 100 | 90 |
| A-50 | 250 | 100 | 100 | 100 | 100 |
| A-51 | 250 | 100 | 100 | 90 | 90 |
| A-52 | 250 | 0 | 0 | 50 | 0 |
| A-53 | 250 | 90 | 80 | 90 | 80 |
| A-54 | 250 | 0 | 0 | 80 | 10 |
| A-56 | 250 | 20 | 20 | 70 | 0 |
| A-60 | 250 | 80 | 90 | 100 | 80 |
| A-67 | 250 | 80 | 70 | 100 | 20 |
| A-70 | 250 | 10 | 0 | 60 | 0 |
| A-71 | 250 | 100 | 100 | 100 | 100 |
| A-72 | 250 | 30 | 50 | 100 | 30 |
| A-75 | 250 | 20 | 10 | 40 | 0 |
| A-76 | 250 | 30 | 50 | 80 | 80 |
| A-77 | 250 | 30 | 20 | 80 | 0 |
| A-78 | 250 | 90 | 100 | 100 | 90 |
| A-79 | 250 | 20 | 0 | 50 | 0 |
| A-80 | 250 | 30 | 40 | 80 | 50 |
| A-86 | 250 | 10 | 10 | 100 | 10 |
| A-87 | 250 | 90 | 90 | 100 | 100 |
| A-88 | 250 | 90 | 90 | 100 | 100 |
| A-89 | 250 | 100 | 100 | 100 | 100 |
| A-90 | 250 | 100 | 90 | 100 | 100 |
| A-93 | 250 | 50 | 60 | 100 | 60 |
| A-94 | 250 | 20 | 30 | 80 | 0 |
| A-95 | 250 | 90 | 80 | 100 | 90 |
| A-96 | 250 | 50 | 90 | 100 | 90 |
| A-97 | 250 | 10 | 10 | 60 | 10 |
| A-98 | 250 | 30 | 30 | 90 | 20 |
| A-99 | 250 | 80 | 100 | 100 | 100 |
| A-100 | 250 | 30 | 30 | 90 | 10 |
| A-104 | 250 | 40 | 30 | 100 | 30 |
| A-105 | 250 | 30 | 40 | 90 | 40 |
| A-108 | 250 | 70 | 90 | 100 | 90 |

What is claimed is:

1. A compound of formula I

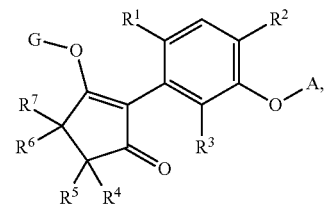

wherein

A is a monocyclic or bicyclic aryl or heteroaryl which contains a heteroatom selected from nitrogen, oxygen and sulfur, and which is unsubstituted or substituted; and wherein, when A is substituted, then A is substituted by halogen, $C_1$-$C_4$alkyl, $C_1$-$C_4$haloalkyl, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, nitro, cyano, $C_3$-$C_6$cycloalkyl, $C_1$-$C_3$alkylcarbonyl, $C_1$-$C_4$alkoxycarbonyl, aminocarbonyl, $C_1$-$C_3$alkylaminocarbonyl, di($C_1$-$C_3$)alkylaminocarbonyl, $C_1$-$C_3$alkylaminocarbonyloxy, di($C_1$-$C_3$)alkylaminocarbonyloxy, aminothiocarbonyl, $C_1$-$C_3$alkylaminothiocarbonyl, di($C_1$-$C_3$)alkylaminothiocarbonyl, $C_1$-$C_4$alkylcarbonylamino, $C_3$-$C_6$cycloalkylcarbonylamino, $C_1$-$C_4$alkoxycarbonylamino, $C_1$-$C_4$alkylthiocarbonylamino, $C_1$-$C_3$alkoxy($C_1$-$C_3$)alkyl, $C_1$alkylthio($C_1$)alkyl, $C_1$alkylsulfinyl($C_1$)alkyl, $C_1$alkylsulfonyl($C_1$)alkyl, $C_1$-$C_3$alkylsulfonyloxy, $C_1$-$C_3$haloalkylsulfonyloxy or di($C_1$)alkylaminosulfonyl;

$R^1$ is methyl, ethyl, n-propyl, isopropyl, cyclopropyl, halomethyl, haloethyl, vinyl, propenyl, ethynyl, propynyl, halogen, methoxy, ethoxy, halomethoxy or haloethoxy;

$R^2$ and $R^3$ are hydrogen; and $R^4$, $R^5$, $R^6$, and $R^7$ are independently of each other hydrogen, halogen, optionally substituted $C_1$-$C_6$alkyl, optionally substituted $C_3$-$C_7$cycloalkyl, optionally substituted $C_2$-$C_6$alkenyl, optionally substituted $C_5$-$C_7$cycloalkenyl, optionally substituted $C_2$-$C_6$alkynyl, optionally substituted $C_1$-$C_6$alkoxy, optionally substituted $C_3$-$C_7$cycloalkyloxy, optionally substituted $C_1$-$C_6$alkylthio, optionally substituted $C_1$-$C_6$alkylsulfinyl, optionally substituted $C_1$-$C_6$alkylsulfonyl, optionally substituted aryl, optionally substituted aryloxy, optionally substituted arylthio, optionally substituted arylsulfinyl, optionally substituted arylsulfonyl, optionally substituted heterocyclyl, optionally substituted heterocyclyloxy, optionally substituted heterocyclylthio, optionally substituted heterocyclylsulfinyl, optionally substituted heterocyclylsulfonyl, optionally substituted heteroaryl, optionally substituted heteroaryloxy, optionally substituted heteroarylthio, optionally substituted heteroarylsulfinyl, optionally substituted heteroarylsulfonyl, cyano or amino;

or $R^4$ and $R^5$, or $R^6$ and $R^7$, together with the atoms to which they are bonded, form an optionally substituted saturated or unsaturated carbocyclyl or heterocyclyl which contains one or two heteroatoms selected from nitrogen, oxygen and sulfur;

or $R^5$ and $R^6$, together with the atoms to which they are bonded, form an optionally substituted saturated or unsaturated carbocyclyl or heterocyclyl which contains one or two heteroatoms selected from nitrogen, oxygen and sulfur, and wherein the carbocyclyl is optionally bridged by $C_1$-$C_2$alkyldiyl or by oxygen; and G is hydrogen or an agriculturally acceptable metal, sulfonium, ammonium or latentiating group;

wherein, when G is a latentiating group, then G is phenyl($C_1$)alkyl, heteroaryl($C_1$)alkyl, $C_3$alkenyl, $C_3$haloalkenyl, $C_3$alkynyl, $C(X^a)$—$R^a$, $C(X^b)$—$X^c$—$R^b$, $C(X^d)$—$N(R^c)$—$R^d$, —$SO_2$—$R^e$, —$P(X^e)(R^f)$—$R^g$ or $CH_2$—$X^f$—$R^h$;

wherein, for the latentiating group within G, the phenyl in the phenyl($C_1$)alkyl and the heteroaryl in the heteroaryl($C_1$)alkyl are independently of each other optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano by nitro;

wherein $X^a$, $X^b$, $X^c$, $X^d$, $X^e$ and $X^f$ are independently of each other oxygen or sulfur; and wherein $R^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$-trialkylsilyl($C_1$-$C_5$)alkyl, phenyl($C_1$-$C_5$)alkyl wherein the phenyl is optionally substituted, heteroaryl($C_1$-$C_5$)alkyl wherein the heteroaryl is optionally substituted, $C_2$-$C_5$haloalkenyl, $C_3$-$C_8$cycloalkyl, phenyl, substituted phenyl, heteroaryl, or substituted heteroaryl;

wherein in $R^a$, the phenyl in the phenyl($C_1$-$C_5$)alkyl and the heteroaryl in the heteroaryl($C_1$-$C_5$)alkyl are independently of each other optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro;

and wherein, in $R^a$, the substituted phenyl and the substituted heteroaryl are independently of each other substituted by $C_1$-$C_3$alkyl, $C_1$-$C_3$haloalkyl, $C_1$-$C_3$alkoxy, $C_1$-$C_3$haloalkoxy, halogen, cyano or nitro; and $R^b$ is $C_1$-$C_{18}$alkyl, $C_3$-$C_{18}$alkenyl, $C_3$-$C_{18}$alkynyl, $C_2$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$-trialkylsilyl($C_1$-$C_5$)alkyl, phenyl($C_1$-$C_5$)alkyl wherein the phenyl is optionally substituted heteroaryl ($C_1$-$C_5$)alkyl wherein the heteroaryl is optionally substituted, $C_3$-$C_5$haloalkenyl, $C_3$-$C_8$cycloalkyl, phenyl, substituted phenyl, heteroaryl, or substituted heteroaryl;

wherein, in $R^b$, the phenyl in the phenyl($C_1$-$C_5$)alkyl and the heteroaryl in the heteroaryl($C_1$-$C_5$)alkyl are independently of each other optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro;

and wherein, in $R^b$, the substituted phenyl and the substituted heteroaryl are independently of each other substituted by $C_1$-$C_3$alkyl, $C_1$-$C_3$haloalkyl, $C_1$-$C_3$alkoxy, $C_1$-$C_3$haloalkoxy, halogen, cyano or nitro; and $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_5$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$-trialkylsilyl($C_1$-$C_5$)alkyl, phenyl($C_1$-$C_5$)alkyl wherein the phenyl is optionally substituted, heteroaryl($C_1$-$C_5$)alkyl wherein the heteroaryl is optionally substituted, $C_2$-$C_5$haloalkenyl, $C_3$-$C_8$cycloalkyl, phenyl, substituted phenyl, heteroaryl, substituted heteroaryl, heteroarylamino, substituted heteroarylamino, diheteroarylamino, substituted diheteroarylamino, phenylamino, substituted phenylamino, diphenylamino, substituted diphenylamino, $C_3$-$C_7$cycloalkylamino, di($C_3$-$C_7$)cycloalkylamino or $C_3$-$C_7$cycloalkoxy;

or $R^c$ and $R^d$ are joined together to form a 3-7 membered ring, optionally containing one heteroatom selected from O or S;

wherein, in $R^c$ and $R^d$, the phenyl in the phenyl($C_1$-$C_5$)alkyl and the heteroaryl in the heteroaryl($C_1$-$C_5$)alkyl are independently of each other optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro;

and wherein, in $R^c$ and $R^d$, the substituted phenyl, the substituted heteroaryl, the substituted heteroarylamino, the substituted diheteroarylamino, the substituted phenylamino, and the substituted diphenylamino are independently of each other substituted by $C_1$-$C_3$alkyl, $C_1$-$C_3$haloalkoxy, $C_1$-$C_3$alkoxy, $C_1$-$C_3$haloalkoxy, halogen, cyano or nitro; and $R^e$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-

$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$-trialkylsilyl($C_1$-$C_5$)alkyl, phenyl($C_1$-$C_5$)alkyl wherein the phenyl is optionally substituted, heteroaryl($C_1$-$C_5$)alkyl wherein the heteroaryl is optionally substituted, $C_2$-$C_5$haloalkenyl, $C_3$-$C_8$cycloalkyl, phenyl, substituted phenyl, heteroaryl, substituted heteroaryl, heteroarylamino, substituted heteroarylamino, diheteroarylamino, substituted diheteroarylamino, phenylamino, substituted phenylamino, diphenylamino, substituted diphenylamino, $C_3$-$C_7$cycloalkylamino, di($C_3$-$C_7$)cycloalkylamino, $C_3$-$C_7$cycloalkoxy, $C_1$-$C_{10}$alkoxy, $C_1$-$C_{10}$haloalkoxy, $C_1$-$C_5$alkylamino or $C_2$-$C_8$dialkylamino;

wherein, in $R^e$, the phenyl in the phenyl($C_1$-$C_5$)alkyl and the heteroaryl in the heteroaryl($C_1$-$C_5$)alkyl are independently of each other optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro;

and wherein, in $R^e$, the substituted phenyl, the substituted heteroaryl, the substituted heteroarylamino, the substituted diheteroarylamino, the substituted phenylamino, and the substituted diphenylamino are independently of each other substituted by $C_1$-$C_3$alkyl, $C_1$-$C_3$haloalkyl, $C_1$-$C_3$alkoxy, $C_1$-$C_3$haloalkoxy, halogen, cyano or nitro;

$R^f$ and $R^g$ are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$haloalkyl, $C_1$-$C_{10}$cyanoalkyl, $C_1$-$C_{10}$-nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$-trialkylsilyl($C_1$-$C_5$)alkyl, phenyl($C_1$-$C_5$)alkyl wherein the phenyl is optionally substituted, heteroaryl($C_1$-$C_5$)alkyl wherein the heteroaryl is optionally substituted, $C_2$-$C_5$haloalkenyl, $C_3$-$C_8$cycloalkyl, phenyl, substituted phenyl, heteroaryl, substituted heteroaryl, heteroarylamino, substituted heteroarylamino, diheteroarylamino, substituted diheteroarylamino, phenylamino, substituted phenylamino, diphenylamino, substituted diphenylamino, $C_3$-$C_7$cycloalkylamino, di($C_3$-$C_7$)cycloalkylamino, $C_3$-$C_7$cycloalkoxy, $C_1$-$C_{10}$haloalkoxy, $C_1$-$C_5$alkylamino, $C_2$-$C_8$dialkylamino, optionally substituted benzyloxy or optionally substituted phenoxy;

wherein in $R^f$ and $R^g$ the phenyl in the phenyl($C_1$-$C_5$)alkyl and the heteroaryl in the heteroaryl($C_1$-$C_5$)alkyl are independently of each other optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro;

and wherein, in $R^f$ and $R^g$, the substituted phenyl, the substituted heteroaryl, the substituted heteroarylamino, the substituted diheteroarylamino, the substituted phenylamino, and the substituted diphenylamino are independently of each other substituted by $C_1$-$C_3$alkyl, $C_1$-$C_3$haloalkyl, $C_1$-$C_3$alkoxy, $C_1$-$C_3$haloalkoxy, halogen, cyano or nitro;

and wherein, in $R^f$ and $R^g$, the benzyl group in the benzyloxy and the phenyl group is the phenoxy are optionally substituted by $C_1$-$C_3$alkyl, $C_1$-$C_3$haloalkyl, $C_1$-$C_3$alkoxy, $C_1$-$C_3$haloalkoxy, halogen, cyano or nitro; and $R^h$ is $C_1$-$C_{10}$alkyl, $C_3$-$C_{10}$alkenyl, $C_3$-$C_{10}$alkynyl, $C_1$-$C_{10}$haloalkyl, $C_1$-$C_{10}$cyanoalkyl, $C_1$-$C_{10}$nitroalkyl, $C_2$-$C_{10}$-aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$-trialkylsilyl($C_1$-$C_5$)alkyl, phenyl($C_1$-$C_5$)alkyl wherein the phenyl is optionally substituted, heteroaryl($C_1$-$C_5$)alkyl wherein the heteroaryl is optionally substituted, phenoxy($C_1$-$C_5$)alkyl wherein the phenyl is optionally substituted, heteroaryloxy($C_1$-$C_5$)alkyl wherein the heteroaryl is optionally substituted, $C_3$-$C_5$haloalkenyl, $C_3$-$C_8$cycloalkyl, phenyl, substituted phenyl, heteroaryl or substituted heteroaryl;

wherein, in $R^h$, the phenyl in the phenyl($C_1$-$C_5$)alkyl, the heteroaryl in the heteroaryl($C_1$-$C_5$)alkyl, the phenyl in the phenoxy($C_1$-$C_5$)alkyl and the heteroaryl in the heteroaryloxy($C_1$-$C_5$)alkyl are independently of each other optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro;

and wherein, in $R^h$, the substituted phenyl and the substituted heteroaryl are independently of each other substituted by $C_1$-$C_3$alkyl, $C_1$-$C_3$haloalkyl, $C_1$-$C_3$alkoxy, $C_1$-$C_3$haloalkoxy, halogen, cyano or by nitro;

and wherein:

"aryl" means phenyl or naphthyl;

"heteroaryl" means an aromatic ring system containing at least one heteroatom and consisting either of a single ring or of two fused rings; and "heterocyclyl" means a non-aromatic monocyclic or bicyclic ring system containing up to 7 atoms including one or two heteroatoms selected from O, S and N;

and wherein:

when present, the optional substituents on an alkyl moiety, or an alkyl-containing group larger than the corresponding alkyl, are one or more of halogen, nitro, cyano, $C_3$-$C_7$cyloalkyl, $C_5$-$C_7$cycloalkenyl, hydroxyl, $C_1$-$C_{10}$alkoxy, $C_1$-$C_{10}$alkoxy($C_1$-$C_{10}$)alkoxy, tri($C_1$-$C_4$)alkylsilyl($C_1$-$C_6$)alkoxy, $C_1$-$C_6$alkoxycarbonyl($C_1$-$C_{10}$)alkoxy, $C_1$-$C_6$alkoxycarbonyl($C_1$-$C_{10}$)alkoxy, $C_1$-$C_{10}$haloalkoxy, aryl($C_1$-$C_4$)alkoxy wherein the aryl is optionally substituted, $C_3$-$C_7$cycloalkyloxy, $C_3$-$C_{10}$alkenyloxy, $C_3$-$C_{10}$alkynyloxy, mercapto, $C_1$-$C_{10}$alkylthio, $C_1$-$C_{10}$haloalkylthio, aryl($C_1$-$C_4$)alkylthio wherein the aryl group is optionally substituted, $C_3$-$C_7$cycloalkylthio, tri($C_1$-$C_4$)alkylsilyl($C_1$-$C_6$)alkylthio, arylthio wherein the aryl group is optionally substituted, $C_1$-$C_6$alkylsulfonyl, $C_1$-$C_6$haloalkylsulfonyl, $C_1$-$C_6$alkylsulfinyl, $C_1$-$C_6$haloalkylsulfinyl, arylsulfonyl wherein the aryl group is optionally substituted, tri($C_1$-$C_4$)alkylsilyl, aryldi($C_1$-$C_4$)alkylsilyl, $C_1$-$C_4$alkyldiarylsilyl, triarylsilyl, aryl($C_1$-$C_4$)alkylthio ($C_1$-$C_4$)alkyl, aryloxy($C_1$-$C_4$)alkyl, formyl, $C_1$-$C_{10}$alkylcarbonyl, $HO_2C$, $C_1$-$C_{10}$alkoxycarbonyl, aminocarbonyl, $C_1$-$C_6$alkylaminocarbonyl, di($C_1$-$C_6$)alkylaminocarbonyl, N—($C_1$-$C_3$)alkyl-N—($C_1$-$C_3$)alkoxyaminocarbonyl, $C_1$-$C_6$alkylcarbonyloxy, arylcarbonyloxy wherein the aryl group is optionally substituted, di($C_1$-$C_6$)alkylaminocarbonyloxy, $C_1$-$C_6$alkyliminooxy, $C_3$-$C_6$alkenyloxyimino, aryloxyimino, optionally substituted aryl, optionally substituted heteroaryl, heterocyclyl, aryloxy wherein the aryl group is optionally substituted, heteroaryloxy wherein the heteroaryl group is optionally substituted, heterocyclyloxy, amino, $C_1$-$C_6$alkylamino, di($C_1$-$C_6$)alkylamino, $C_1$-$C_6$alkylcarbonylamino, N—($C_1$-$C_6$)alkylcarbonyl-N—($C_1$-$C_6$)alkylamino, $C_2$-$C_6$alkenylcarbonyl, $C_2$-$C_6$alkynylcarbonyl, $C_3$-$C_6$alkenyloxycarbonyl, $C_3$-$C_6$alkynyloxycarbonyl, aryloxycarbonyl wherein the aryl group is optionally substituted, or arylcarbonyl wherein the aryl group is optionally substituted;

wherein, in the optional substituents on the alkyl moiety, $C_3$-$C_7$cyloalkyl, heterocyclyl, the heterocyclyl group in heterocyclyloxy, the cycloalkyl group in $C_3$-$C_7$cycloalkyloxy, and the cycloalkyl group in $C_3$-$C_7$cycloalkylthio are independently of each other optionally substituted with $C_1$-$C_6$alkyl or halogen, and wherein $C_5$-$C_7$cycloalkenyl is optionally substituted with $C_1$-$C_4$alkyl or halogen when present, the optional substituents on alkenyl or alkynyl are the optional substituents as defined for an alkyl moiety;

when present, the optional substituents on heterocyclyl are $C_1$-$C_6$alkyl or $C_1$-$C_6$haloalkyl or are the optional substituents as defined for an alkyl moiety;

when present, the optional substituents on cycloalkyl or cycloalkenyl are $C_1$-$C_3$alkyl or are the optional substituents as defined for an alkyl moiety;

and when present, the optional substituents on aryl, heteroaryl and carbocycles, unless otherwise indicated, are selected, independently, from halogen, nitro, cyano, isothiocyanato, $C_1$-$C_6$alkyl, $C_1$-$C_6$haloalkyl, $C_1$alkoxy ($C_1$)alkyl, $C_2$-$C_6$alkenyl, $C_2$-$C_6$haloalkenyl, $C_2$-$C_6$alkynyl, $C_3$cycloalkyl optionally substituted with $C_1$-$C_6$alkyl or halogen, hydroxy, $C_1$-$C_{10}$alkoxy, $C_1$alkoxy($C_1$)alkoxy, $C_1$alkoxycarbonyl($C_1$)alkoxy, $C_1$-$C_{10}$haloalkoxy, $C_3$alkenyloxy, $C_3$alkynyloxy, mercapto, $C_1$alkylthio, $C_1$haloalkylthio, $C_1$alkylsulfonyl, $C_1$haloalkylsulfonyl, $C_1$alkylsulfinyl, $C_1$haloalkylsulfinyl, $C_1$alkylcarbonyl, $HO_2C$, $C_1$alkoxycarbonyl, aminocarbonyl, $C_1$alkylaminocarbonyl, di($C_1$)alkylaminocarbonyl N—($C_1$)alkyl-N—($C_1$)alkoxyaminocarbonyl, $C_1$alkylcarbonyloxy, di($C_1$)alkylaminocarbonyloxy, amino, $C_1$alkylamino, di($C_1$)alkylamino, $C_1$alkylcarbonylamino, and N—($C_1$)alkylcarbonyl-N—($C_1$)alkylamino.

2. A compound according to claim 1, wherein A is phenyl, naphthyl, a 5- or a 6-membered heteroaryl or a bicyclic 8- to 10-membered heteroaryl.

3. A compound according to claim 1, wherein A is substituted by halogen, $C_1$-$C_4$alkyl, $C_1$-$C_4$haloalkyl, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, nitro, cyano, $C_3$-$C_6$cycloalkyl, $C_1$-$C_3$alkylcarbonyl, $C_1$-$C_4$alkoxycarbonyl, aminocarbonyl, $C_1$-$C_3$alkylaminocarbonyl, di($C_1$-$C_3$)alkylaminocarbonyl, $C_1$-$C_3$alkylaminocarbonyloxy, di($C_1$-$C_3$)alkylaminocarbonyloxy, aminothiocarbonyl, $C_1$-$C_3$alkylaminothiocarbonyl, di($C_1$-$C_3$)alkylaminothiocarbonyl, $C_1$-$C_4$alkylcarbonylamino, $C_3$-$C_6$cycloalkylcarbonylamino, $C_1$-$C_4$alkoxycarbonylamino, $C_1$-$C_4$alkylthiocarbonylamino, $C_1$-$C_3$alkoxy($C_1$-$C_3$)alkyl, $C_1$alkylthio($C_1$)alkyl, $C_1$alkylsulfinyl($C_1$)alkyl, $C_1$alkylsulfonyl($C_1$)alkyl, $C_1$-$C_3$alkylsulfonyloxy, $C_1$-$C_3$haloalkylsulfonyloxy or di($C_1$)alkylaminosulfonyl.

4. A compound according to claim 2, wherein A is phenyl, naphthyl, pyridyl, pyrazinyl, pyrimidinyl, pyridazinyl, benzothiazolyl, benzoxazolyl, cinnolinyl, quinolinyl, quinazolinyl, quinoxalinyl or benzotriazinyl, in each case substituted by halogen, methyl, ethyl, trifluoromethyl, methoxy, difluoromethoxy, trifluoromethoxy, nitro or cyano.

5. A compound according to claim 1, wherein $R^1$ is methyl, ethyl, n-propyl, cyclopropyl, halogen, halomethoxy or haloethoxy.

6. A compound according to claim 5, wherein $R^1$ is ethyl.

7. A compound according to claim 1, wherein $R^4$, $R^5$, $R^6$ and $R^7$ are independently of each other hydrogen, $C_1$-$C_6$alkyl, $C_1$-$C_4$haloalkyl, $C_1$-$C_4$alkoxy($C_1$-$C_4$)alkyl, optionally substituted five- or six-membered heterocyclyl, or optionally substituted five- or six-membered heterocyclyl($C_1$-$C_2$)alkyl;

or $R^4$ and $R^5$, or $R^6$ and $R^7$, together with the atoms to which they are bonded, form an optionally substituted saturated or unsaturated five- or six-membered carbocyclyl or heterocyclyl which contains one or two oxygen atoms;

or $R^5$ and $R^6$, with the atoms to which they are bonded, form an optionally substituted five- or six-membered saturated or unsaturated carbocyclyl which is optionally bridged by $C_1$-$C_2$alkyldiyl or by oxygen.

8. A compound according to claim 1, wherein $R^4$ and $R^7$ are hydrogen; and $R^5$ and $R^6$, with the atoms to which they are bonded, form a six-membered saturated or unsaturated carbocyclyl which is bridged by $C_1$-$C_2$alkyldiyl or by oxygen.

9. A compound according to any of the preceding claims, wherein "aryl" means phenyl.

10. A compound according to claim 1, wherein, when G is a latentiating group, then G is —C($X^a$)—$R^a$ or —C($X^b$)—$X^c$—$R^b$, and the meanings of $X^a$, $R^a$, $X^b$, $X^c$ and $R^b$ are as defined in claim 1.

11. A compound according to claim 1, wherein G is hydrogen, an alkali metal or an alkaline earth metal.

12. A compound according to claim 1, wherein:

$R^1$ is ethyl or cyclopropyl;

$R^2$ and $R^3$ are hydrogen; and $R^4$, $R^7$, $R^8$ and $R^6$ are hydrogen; or $R^4$ and $R^7$ are hydrogen and $R^5$ and $R^6$, with the atoms to which they are bonded, form a six-membered saturated carbocyclyl which is bridged by $C_1$-$C_2$alkyldiyl or by oxygen; and A is phenyl substituted by fluoro, chloro, bromo, methyl, trifluoromethyl, methoxy, trifluoromethoxy, cyano or nitro; or A is pyridyl, pyrimidinyl, pyrazinyl, benzothiazolyl, quinolinyl or quinoxalinyl, in each case substituted by fluoro, chloro, bromo, trifluoromethyl, methoxy, or nitro; and G is hydrogen.

13. A process for the preparation of a compound of formula I according to claim 1, wherein G is hydrogen, which comprises reacting a compound of formula (BB)

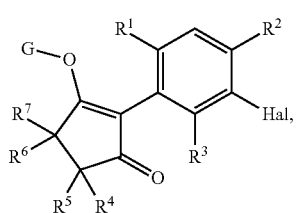
(BB)

wherein Hal is bromine or iodine and $R^1$ to $R^7$ are as defined in claim 1, with a compound A-OH, wherein A is as defined in claim 1, in the presence of a catalyst, a ligand or additive, a base and a solvent.

14. A process for the preparation of a compound of formula I according to claim 1, wherein G is hydrogen, which comprises reacting a compound of formula (CC)

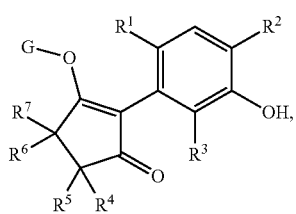
(CC)

wherein and $R^1$ to $R^7$ are as defined in claim 1 with a compound A-Hal, wherein A is as defined in claim 1 and Hal is fluorine, chlorine, bromine or iodine, in the presence of a base and a solvent, and in the presence or absence of a catalyst and a ligand.

15. A process for the preparation of a compound of formula I according to claim 1, wherein G is hydrogen and $R^5$ and $R^6$, together with the atoms to which they are bonded, form an optionally substituted unsaturated carbocyclyl which is further bridged by $C_1$-$C_2$alkyldiyl or oxygen, which comprises reacting a compound of formula (M)

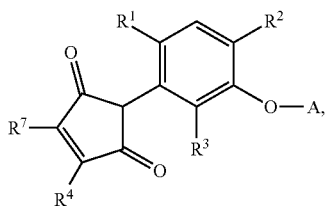
(M)

wherein A, $R^1$ to $R^4$ and $R^7$ are as defined in claim 1, with a compound of formula (O)

(O)

wherein W is $C_1$-$C_2$alkyldiyl or oxygen, and $R_b$ is hydrogen or a substituent suitable for preparing the compound of formula I, in the presence of a catalyst and a solvent.

16. A compound of formula (M)

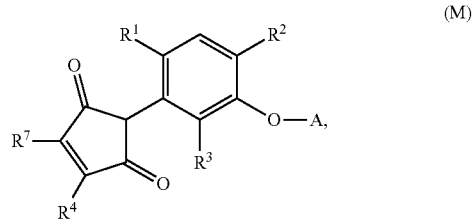
(M)

wherein A, $R^1$ to $R^4$ and $R^7$ are as defined in claim 1.

17. A herbicidal composition, which, in addition to comprising formulation adjuvants, comprises a herbicidally effective amount of a compound of formula I as defined in claim 1.

18. A method of controlling grasses and weeds in crops of useful plants, which comprises applying a herbicidally effective amount of a compound of formula I as defined in claim 1, or of a composition comprising such a compound, to the plants or to the locus thereof.

19. A compound as claimed in claim 1, which is a compound of one of the following:

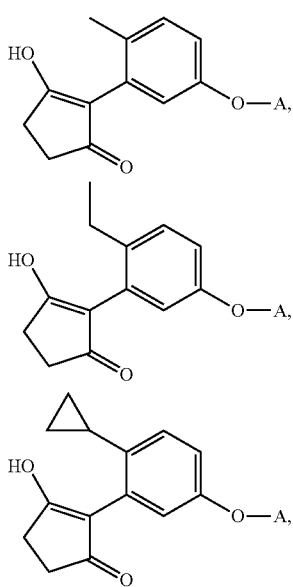

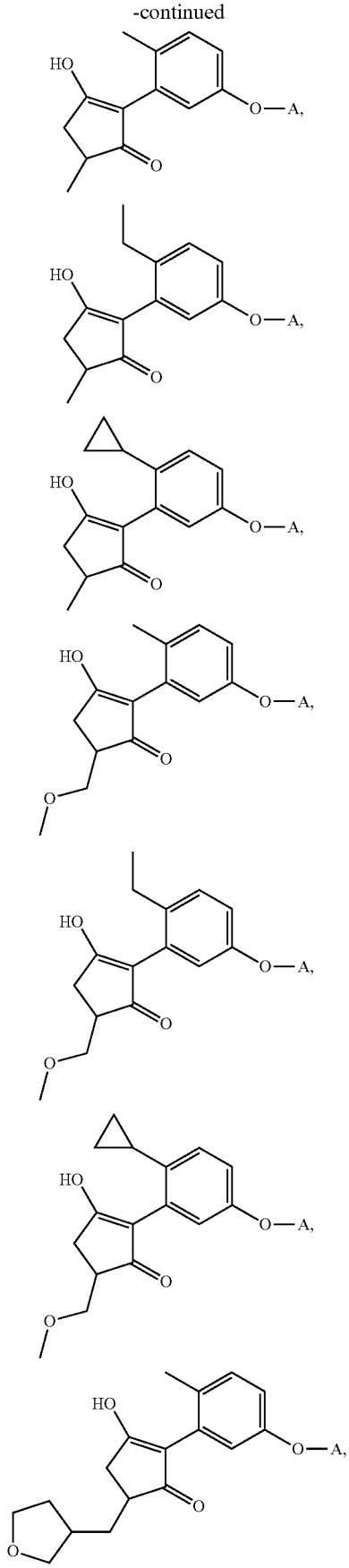

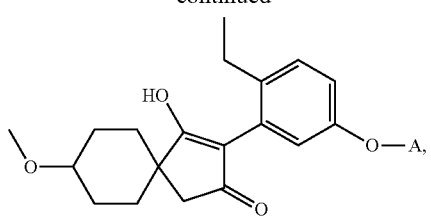
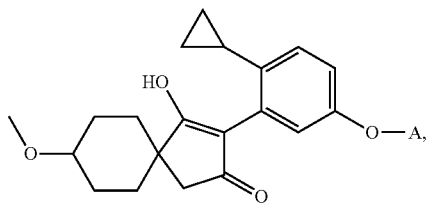
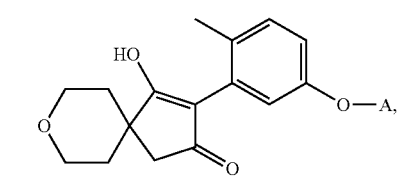
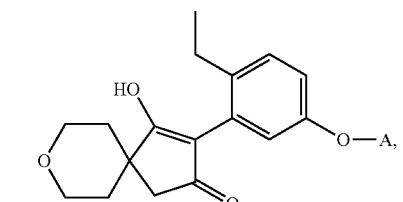
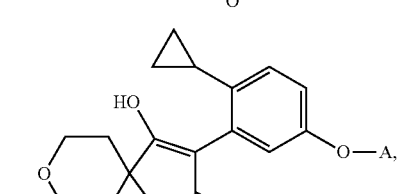
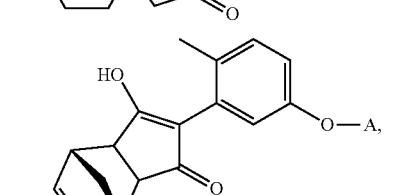
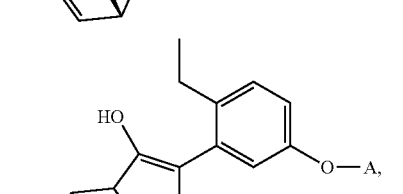
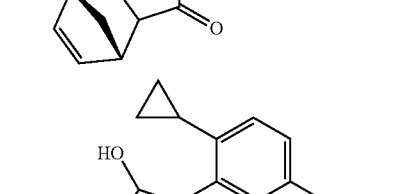
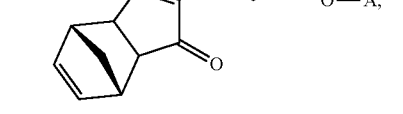
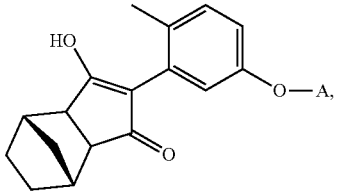
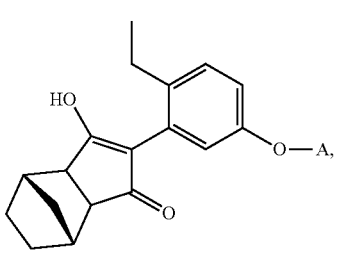
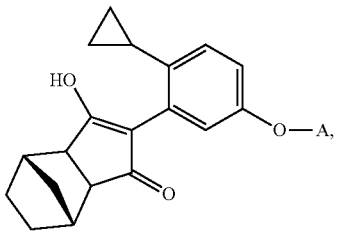
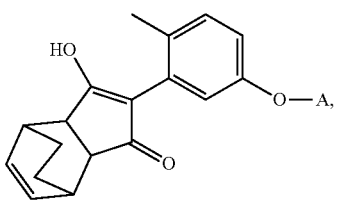
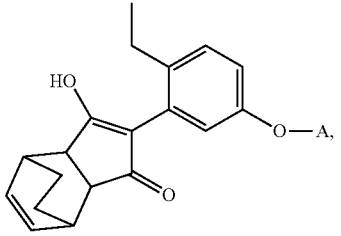
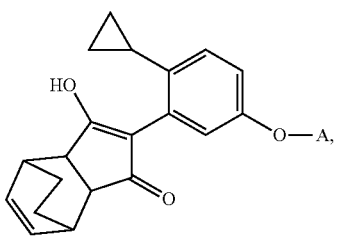
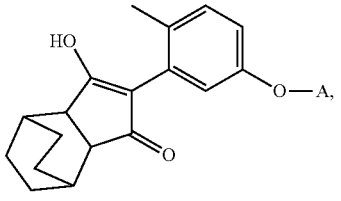

-continued

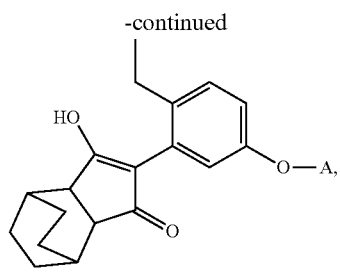
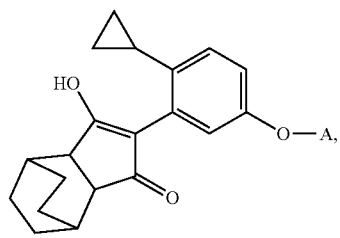
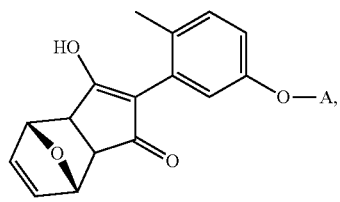
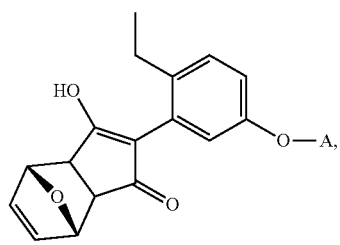
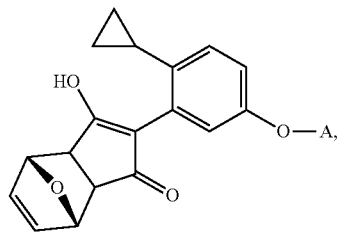
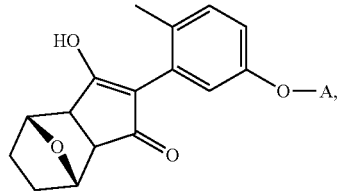
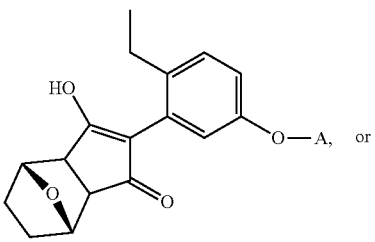 or -continued

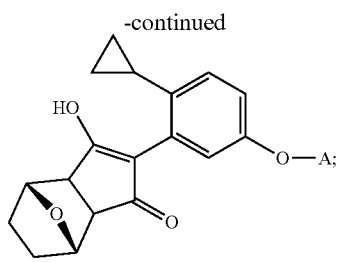

wherein A is phenyl, 2-bromophenyl, 2-chlorophenyl, 2-cyanophenyl, 2-difluoromethoxyphenyl, 2-fluorophenyl, 2-methoxyphenyl, 2-methylphenyl, 2-nitrophenyl, 2-trifluoromethoxyphenyl, 2-trifluoromethylphenyl, 3-bromophenyl, 3-chlorophenyl, 3-cyanophenyl, 3-difluoromethoxyphenyl, 3-fluorophenyl, 3-methoxyphenyl, 3-methylphenyl, 3-nitrophenyl, 3-trifluoromethoxyphenyl, 3-trifluoromethylphenyl, 4-bromophenyl, 4-chlorophenyl, 4-cyanophenyl, 4-difluoromethoxyphenyl, 4-fluorophenyl, 4-methanesulfonyl, 4-methoxyphenyl, 4-methylphenyl, 4-nitrophenyl, 4-trifluoromethoxyphenyl, 4-trifluoromethylphenyl, 4-bromo-2-chlorophenyl, 2,4-dichlorophenyl, 2-chloro-4-cyanophenyl, 2-chloro-4-difluoromethoxyphenyl, 2-chloro-4-fluorophenyl, 2-chloro-4-methoxyphenyl, 2-chloro-4-methylphenyl, 2-chloro-4-nitrophenyl, 2-chloro-4-trifluoromethoxyphenyl, 2-chloro-4-trifluoromethylphenyl, 4-bromo-3-chlorophenyl, 3,4-dichlorophenyl, 3-chloro-4-cyanophenyl, 3-chloro-4-difluoromethoxyphenyl, 3-chloro-4-fluorophenyl, 3-chloro-4-methoxyphenyl, 3-chloro-4-methylphenyl, 3-chloro-4-nitrophenyl, 3-chloro-4-trifluoromethoxyphenyl, 3-chloro-4-trifluoromethylphenyl, 2-bromo-4-chlorophenyl, 4-chloro-2-difluoromethoxyphenyl, 4-chloro-2-cyanophenyl, 4-chloro-2-methoxyphenyl, 4-chloro-2-fluorophenyl, 4-chloro-2-nitrophenyl, 4-chloro-2-methylphenyl, 4-chloro-2-trifluoromethylphenyl, 4-chloro-2-trifluoromethoxyphenyl, 4-chloro-3-trifluoromethoxyphenyl, 3-bromo-4-chlorophenyl, 4-chloro-3-difluoromethoxyphenyl, 4-chloro-3-cyanophenyl, 4-chloro-3-methoxyphenyl, 4-chloro-3-fluorophenyl, 4-chloro-3-nitrophenyl, 4-chloro-3-methylphenyl, 4-chloro-3-trifluoromethylphenyl, 4-bromo-2-fluorophenyl, 2-difluoro-4-difluoromethoxyphenyl, 4-cyano-2-fluorophenyl, 2-fluoro-4-methoxyphenyl, 2,4-fluorophenyl, 2-fluoro-4-nitrophenyl, 2-fluoro-4-methylphenyl, 2-fluoro-4-trifluoromethylphenyl, 2-fluoro-4-trifluoromethoxyphenyl, 4-bromo-3-fluorophenyl, 4-cyano-3-fluorophenyl, 3-difluoro-4-difluoromethoxyphenyl, 3,4-fluorophenyl, 3-fluoro-4-methoxyphenyl, 3-fluoro-4-methylphenyl, 3-fluoro-4-nitrophenyl, 3-fluoro-4-trifluoromethoxyphenyl, 3-fluoro-4-trifluoromethylphenyl, 4-chloro-2,3-difluorophenyl, 4-chloro-2,5-difluorophenyl, 4-chloro-2,6-difluorophenyl, 4-chloro-3,5-difluorophenyl, 2,4-dichloro-3-fluorophenyl, 2,4-dichloro-5-fluorophenyl, 2,4-dichloro-6-fluorophenyl, 2,3,4-trifluorophenyl, 2,4,6-trifluorophenyl, 2,4,5-trifluorophenyl, 3,4,5-trifluorophenyl, pentafluorophenyl, 2-bromo-4-cyanophenyl, 3-bromo-4-cyanophenyl, 4-bromo-2-cyanophenyl, 4-bromo-3-cyanophenyl, 2-cyano-4-nitrophenyl, 3-cyano-4-nitrophenyl, 2-cyano-4-trifluoromethylphenyl, 3-cyano-4-trifluoromethylphenyl, 2,4-dicyanophenyl, 3,4-dicyanophenyl, 3-chloropyridin-2-yl, 4-chloropyridin-2-yl, 5-chloropyridin-2-yl, 6-chloropyridin-2-yl, 2-chloropyridin-3-yl, 4-chloropyridin-3-yl, 5-chloropyridin-3-yl, 6-chloropyridin-3-yl, 2-chloropyridin-4-yl, 3-chloropyridin-4-yl, 3,4-dichloropyridin-2-yl, 3,5-dichloropyridin-2-yl, 3,6-dichloropyridin-2-yl, 2,5-dichloropyridin-3-yl, 2,6-dichloropyridin-3-yl, 2,3-dichloropyridin-4-yl, 2,5-dichloropyridin-4-yl, 3,5,6-trichloropyridin-2-yl, 3-fluoropyridin-2-yl, 4-fluoropyridin-2-yl, 5-fluoropyridin-2-yl, 6-fluoropyridin-2-yl, 2-fluoropyridin-3-yl, 4-fluoropyridin-3-yl, 5-fluoropyridin-3-yl, 6-fluoropyridin-3-yl, 2-fluoropyridin-4-yl, 3-fluoropyridin-4-yl, 3,4-difluoropyridin-2-yl, 3,5-difluoropyridin-2-yl, 3,6-difluoropyridin-2-yl, 2,5-difluoropyridin-3-yl, 2,6-difluoropyridin-3-yl, 2,3-difluoropyridin-4-yl, 2,5-difluoropyridin-4-yl, 3,5,6-trifluoropyridin-2-yl, 3-trifluoromethylpyridin-2-yl, 4-trifluoromethylpyridin-2-yl, 5-trifluoromethylpyridin-2-yl, 6-trifluoromethylpyridin-2-yl, 2-trifluoromethylpyridin-3-yl, 4-trifluoromethylpyridin-3-yl, 5-trifluoromethylpyridin-3-yl, 6-trifluoromethylpyridin-3-yl, 2-trifluoromethylpyridin-4-yl, 3-trifluoromethylpyridin-4-yl, 4-chloro-3-fluoropyridin-2-yl, 5-chloro-3-fluoropyridin-2-yl, 6-chloro-3-fluoropyridin-2-yl, 3-chloro-4-fluoropyridin-2-yl, 3-chloro-5-fluoropyridin-2-yl, 3-chloro-6-fluoropyridin-2-yl, 3-chloro-5-trifluoromethylpyridin-2-yl, 3-fluoro-5-trifluoromethylpyridin-2-yl, 6-fluoro-3,4,5-trichloropyridin-2-yl, 4-methyl-3,5,6-trifluoropyridin-2-yl, pyrimidin-2-yl, 5-fluoropyrimidin-2-yl, 5-chloropyrimidin-2-yl, 5-bromopyrimidin-2-yl, 6-chloropyridazin-3-yl, 6-bromopyridazin-3-yl, quinoline-2-yl, 6-fluoroquinolin-2-yl, 7-fluoroquinolin-2-yl, 6-chloroquinolin-2-yl, 7-chloroquinolin-2-yl, 6-bromoquinolin-2-yl, 7-bromoquinolin-2-yl, 6-trifluoromethylquinolin-2-yl, 7-trifluoromethylquinolin-2-yl, quinoxalin-2-yl, 6-fluoroquinoxazin-2-yl, 7-fluoroquinoxalin-2-yl, 6-chloroquinoxalin-2-yl, 7-chloroquinoxalin-2-yl, 6-bromoquinoxalin-2-yl, 7-bromoquinoxalin-2-yl, 6-trifluoromethylquinoxalin-2-yl, 7-trifluoromethylquinoxalin-2-yl, quinazolin-2-yl, 6-fluoroquinazolin-2-yl, 7-fluoroquinazolin-2-yl, 6-chloroquinazolin-2-yl, 7-chloroquinazolin-2-yl, 6-bromoquinazolin-2-yl, 7-bromoquinazolin-2-yl, 6-trifluoromethylquinazolin-2-yl, 7-trifluoromethylquinazolin-2-yl, benzoxazol-2-yl, 5-fluorobenzoxazol-2-yl, 6-fluorobenzoxazol-2-yl, 5-chlorobenzoxazol-2-yl, 6-chlorobenzoxazol-2-yl, 5-bromobenzoxazol-2-yl, 6-bromobenzoxazol-2-yl, 5-trifluoromethylbenzoxazol-2-yl, 6-trifluoromethylbenzoxazol-2-yl, benzothiazol-2-yl, 5-fluorobenzothiazol-2-yl, 6-fluorobenzothiazol-2-yl, 5-chlorobenzothiazol-2-yl, 6-chlorobenzothiazol-2-yl, 5-bromobenzothiazol-2-yl, 6-bromobenzothiazol-2-yl, 5-trifluoromethylbenzothiazol-2-yl, 6-trifluoromethylbenzothiazol-2-yl, benzo[1,2,4]triazin-3-yl, 6-fluorobenzo[1,2,4]triazin-3-yl, 7-fluorobenzo[1,2,4]triazin-3-yl, 6-chlorobenzo[1,2,4]triazin-3-yl, 7-chlorobenzo[1,2,4]triazin-3-yl, 6-bromobenzo[1,2,4]triazin-3-yl, 7-bromo benzo[1,2,4]triazin-3-yl, 6-trifluoromethylbenzo[1,2,4]-triazin-3-yl, or 7-trifluoromethylbenzo[1,2,4]triazin-3-yl.

\* \* \* \* \*